US007220412B2

(12) United States Patent
Abuljadayel

(10) Patent No.: US 7,220,412 B2
(45) Date of Patent: May 22, 2007

(54) METHOD OF PREPARING AN UNDIFFERENTIATED CELL

(75) Inventor: Ilham Saleh Abuljadayel, London (GB)

(73) Assignee: Ghazi Jaswinder Dhoot, London (GB)

(*) Notice: Subject to any disclaimer, the term of this patent is extended or adjusted under 35 U.S.C. 154(b) by 650 days.

(21) Appl. No.: 10/140,978

(22) Filed: May 8, 2002

(65) Prior Publication Data
US 2003/0138947 A1 Jul. 24, 2003

Related U.S. Application Data

(60) Continuation of application No. 09/568,254, filed on May 10, 2000, which is a continuation-in-part of application No. 08/594,164, filed on Jan. 31, 1996, now Pat. No. 6,090,625, and a continuation-in-part of application No. 09/521,700, filed on Mar. 9, 2000, now abandoned, and a division of application No. 08/594,164, filed on Jan. 31, 1996, now Pat. No. 6,090,625.

(30) Foreign Application Priority Data
Feb. 2, 1995 (GB) ................................. 9502022.8

(51) Int. Cl.
*A61K 39/395* (2006.01)
*C12N 5/08* (2006.01)

(52) U.S. Cl. .................... 424/144.1; 435/373; 435/374; 435/377

(58) Field of Classification Search ............. 424/139.1, 424/152.1, 153.1, 154.1, 155.1, 172.1, 173.1, 424/174.1, 130.1, 141.1, 144.1
See application file for complete search history.

(56) References Cited

U.S. PATENT DOCUMENTS

| 5,004,681 | A | 4/1991 | Boyse et al. |
| 5,843,780 | A | 12/1998 | Thomson |
| 6,200,806 | B1 | 3/2001 | Thomson |
| 6,227,202 | B1 | 5/2001 | Matapurkar |

OTHER PUBLICATIONS

Clark (Protein Engineering of Antibody Molecules for Prophylactic and Therapeutic Applications in Man, 1993, p. 1).*
Reinherz et al (PNAS, 1982, vol. 79, pp. 6047-6051).*
Pettersen et al, (Journal of Immunology, 1998, vol. 160, pp. 4343-4352).*
Genestier et al (Blood, 1997, vol. 90, pp. 3626-3639).*
Genestier et al (Blood, 1997, vol. 90, pp. 726-735).*
Woodle et al, (Journal of Immunology, 1997, vol. 158, pp. 2156-2164).*
Vidovic and Toral (Cancer Letter, 1998, vol. 128, pp. 127-135) t.*
Thibeault et al (Cellular Immunology, 1999, vol. 192, pp. 79-85).*
Berto et al (Journal of Immunology, 2000, vol. 164, pp. 2379-2385).*
Tawara et al (Blood, 2001, vol. 98, pp. 250-B).*
Ulloa-Montoya et al, Journal of Bioscience and Bioengineering, vol. 100, pp. 12-27.*
Miller et al (Biochimica et Biophysica Acta, 2005 vol. 1756, pp. 25-52).*
(Hug, Medicina (Kaunas), 2005, vol. 41, pp. 1002-1010).*
Paul, Fundamental Immunology (textbook), 1993, pp. 15-16.*
Cornwell, J., "A Matter of Your Life and Death," *The Sunday Times Magazine*, Feb. 1, 2004.
Abuljadayel, I.S., "Induction of Stem Cell-Like Plasticity in Mononuclear Cells Derived from Unmobilised Adult Human Peripheral Blood," *Current Medical Research and Opinion*, 19(5): 355-375, 2003.
Abuljadayel, I.S. et al., "SCID Repopulating Cells Derived from Unmobilised Adult Human Peripheral Blood," *Current Medical Research and Opinion*, 20(1): 87-100, 2004.
Scripps Research Institute Press Release, "Regenerative Chemical Turns Muscle Cells into Stem Cells, Say Scientists at the Scripps Research Institute", Dec. 22, 2003.
Boral et al. Blood Preservation in Transfusion Medicine, pp. 938-846. in Henry, J., ed., Clinical Diagnosis and Management by Laboratory Methods, 18th ed., W.B. Saunders Company, Philadelphia, 1991.
Uriel, J., "Cancer, Retrodifferentiation, and the Myth of Faust", Cancer Research 36, 4269-4275, 1976. Sato et al., Blood, 82(12):3600-3609, Dec. 1993.
Nelson et al., "Basic Examination of Blood", pp. 553-603 in Clinical Diagnosis & Management By Laboratory Methods, Henry, J.B. ed., W.B. Saunders Company, Philadelphia, 1991.
Nelson et al., "Hematopoiesis", pp. 604-626, in Clinical Diagnosis & Management By Laboratory Methods, Henry, J.B., ed., W.B. Saunders Company, Philadelphia, 1991.
Ogawa et al., "Renewal and Committment to Differentiation of Hemopoietic Stem Cells (An Interpretive Review)", Blood, vol. 61, No. 5, pp. 823-829, May 1983.
The Molecular Control of Cell Division, Differentiation Committment and Maturation in Haemopoietic Cells, vol. 339, pp. 27-30, May 1989.
Jordan et al., "Cellular and Development Properties of Fetal Hemapoietic Stem Cells", pp. 953-963, Cell, vol. 61, Jun. 1990.
Spangrude et al., "Purification and Characterization of Mouse Hematopoietic Stem Cells", Science, vol. 241, pp. 58-62, Jul. 1988.
Orlic et al., What Defines a Pluripotent Hematopoietic Stem Cell (PHSC): Would the Real PHSC Please Stand Up?, Blood, vol. 84, No. 12, pp. 3991-3994, Dec. 1994.
Moore et al., "Clinical Implications of Positive and Negative Hematopoietic Stem Cell Regulators", Blood, vol. 78, pp. 1-19, Jul. 1991.
Moorehead, P.S., "Human Blood Leukocytes", pp. 58-61, in Tissue Culture, ed. Kruse et al., Academic Press, New York, 1973.

(Continued)

*Primary Examiner*—Karen A. Canella
(74) *Attorney, Agent, or Firm*—Frommer Lawrence & Haug LLP; Thomas J. Kowalski

(57) ABSTRACT

Disclosed is a method of preparing an undifferentiated cell. The method includes contacting a more committed cell with an agent that causes the more committed cell to retrodifferentiate into an undifferentiated cell.

18 Claims, 23 Drawing Sheets

OTHER PUBLICATIONS

Stedman's Medical Dictionary, 24th ed., p. 1352, Williams & Wilkens, Baltimore, 1982.

Nelson et al., "Hematopoiesis", pp. 604-605, in Henry, J., ed., Clinical Diagnosis and Management by Laboratory Methods, 18th ed., W.B. Saunders Company, Philadelphia, 1991.

Hass, R., "Retrodifferentiation—an alternative biological pathway in human leukemia cells", European Journal of Cell Biology, 58:1-11, 1992.

Altomonte, M., et al., "Cross-Linking of HLA Class II Antigens Modulates the Release of Tumor Necrosis Factor-.alpha. by the EBV-B Lymphoblastoid Cell Line JY," The Journal of Immunology (151(10):5115-5122.

Cambier, J.C., et al., "Molecular Mechanisms of Transmembrane Signaling in B Lymphocytes," in Ann Rev Imm. (1987) 5:175-199.

Cambier, J.C., et al., "Ia-Mediated Signal Transduction Leads to Proliferation of Primed B Lymphocytes," J Exp Med (1989) 170:877-886.

Clement, L.T., et al., "Antibodies Reactive with Class II Antigens Encoded for by the Major Histocompatibility Complex inhibit human B Cell Activation," The Journal of Immunology (1986) 136(7):2375-2381.

Deeg, H.J., et al., "Major histocompatibility complex class II molecules, hemopoiesis and the marrow microenvironment," Bone Marrow Transplantation (1993) 12:425-430.

Ghaderi, A.A., et al., "Cross-linking of a sequential epitope within the .alpha.-chain of HLA-DR/DP molecules suppressing B lymphocyte growth and inducing homotypic cell aggregation," Immunology Letters (1994) 39:113-119.

Hajeer, A.H., et al., "Antibodies to major histocompatibility complex class II inhibit proliferation, but increase production of soluble CD23 in lymphoblastoid B-cell lines," Immunology (1993) 80:593-597.

Huss, R., et al., "Major Histocompatibility Complex Class II Expression is Required for Posttransplant Immunological but not for Hemopoietic Reconstitution in Mice," Transplantation (1994) 58(12):1366-1371.

Huss, R., et al., "Differentiation of canine bone marrow cells with hemopoietic characteristics from an adherent stromal cell precursor," Proc Natl Acad Sci USA (1995) 92:748-752.

Mooney, N., et al., "HLA Class-II Antigen-Mediated Induction of a Proliferative Response to Anti-IgM in Human B Lymphocytes," Int J Cancer (1991) Supplement 6:30-33.

Mooney, N.A., et al., "Bacterial Superantigen Signaling via HLA Class II on Human B Lymphocytes," Molecular Immunology (1994) 31(9):675-681.

Morio, T., et al., "Engagement of MHC class II molecules by staphylococcal superantigens activates src-type protein tyrosine kinases," Eur J Immunol (1994) 24:651-658.

Naitoh, K., et al., "Signal Transmission through MHC Class II Molecules in a Human B Lymphoid Progenitor Cell Line: Different Signaling Pathways Depending on the Maturational Stages of B Cells," Microbiol Immunol (1994) 38(12):967-976.

Newell, M.K., et al., "Ligation of major histocompatibility complex class II molecules mediates apoptotic cell death in resting B lymphocytes," Proc Natl Acad Sci USA (1993) 90(Nov.):10459-10463.

Perl, A., et al., "Rearrangement of the T-Cell Receptor Alpha, Beta and Gamma Chain Genes in Chronic Lymphocytic Leukemia," Leukemia Research (1990) 14(2):131-137.

Scholl, P.R., et al., "MHC class II signaling in B-cell activation," Immunology Today (1994) 15(9):418-422.

Takahama, Y., et al., "Disparate functions of I-A and I-E molecules on B cells as evidenced by the inhibition with anti-I-A and anti-I-E antibodies of polyclonal B cell activation," Eur J Immunol (1989) 19:2227-2235.

Truman, J-P., et al., "Lymphocyte programmed cell death is mediated via HLA class II DR," International Immunology (1994) 6(6):887-896.

Wade, W.F., et al., "Structural compartmentalization of MHC class II signaling function," Immunology Today (1993) 14(11):539-546.

J. Uriel; Cancer Research 36, 4269-4275; Nov. 1976; Cancer, Retrodifferentiation, and the Myth of Faust.

M. Fukuda; Cancer Research, 41; 4621-4628; Nov. 1981; Tumor-producing Phorbol Diester-induced specific changes in Cell Surface Glycoprotein Profile of K562 Human Leukemic Cells.

N.J. Curtin, et al.; Br. J. Cancer (1983) 48;495-505; Enzymic retrodifferentiation during hepatocarcinogenesis and liver regeneration in rats in vivo.

E. Chastre, et al.; FEBS Letters; Sep. 1985; vol. 188, No. 2; Vasoactive intestinal peptide receptor activity and specificity during enterocyte-like differentiation and retrodifferentiation of the human colonic cancerous subclone HT29.18.

R. Hass, et al.;Cell Growth & Differentiation; vol. 2, Nov. 1991; pp. 541-548; Protein Kinase C Activation and Protooncogene Expression in Differentiation/Retrodifferentiation of Human U-937 Leukemia Cells.

M. Kobayashi, et al.; Pergamon Leukemia Research, vol. 18, No. 12; pp. 929-933; 1994; Establishment of a retrodifferentiated cell line from a single differentiated rat myelomonocytic leukemia cell:possible roles of retrodifferentiation in relapses of leukemia after diff.-inducing therapy.

Goro Eguchi and Ryuji Kodama, "Transdifferentiation" Cell Biology 1993, 5:1023-1028.

Margaret H. Baron, "Reversibility of the differentiated state in somatic cells" Cell Biology 1993, 5:1050-1056.

Fits and Mage, "Secondary Rearrangements and Post-rearrangement Selection Contribute to Restricted Immunoglobulin DJH Expression in Young Rabbit Bone Marrow," *European Journal of Immunology*, 25: 700-707, 1995.

Frehney, I., Culture of Animal Cells: a Manual of Basic Technique, 3rd Edition, 1994, p. 220-22, 345.

Ayala et al., "Serum Induced Monocyte Differentiation and Monocyte Chemotaxis are Regulated by the p38 MAP Kinase Signal Transduction Pathway," *Journal of Leukocyte Biology*, 67: 869-875, 2000.

Reljic et al., "Suppression of Signal Transducer and Activator of Transcription 3-Dependent B Lymphocyte Terminal Differentiation by BCL-6," *Journal of Experimental Medicine*, 192: 1841-1848, 2000.

Rolink et al., Cold Spring Harbor Symposia on Quantitative Biology, 64: 21-25, 1999.

\* cited by examiner

IgH gene rearrangement b  untreated    24hr CR3/43

5.4 Kb
Germ adherent cells non adherent cells long term culture (buffy coat)

METHOD OF PREPARING AN UNDIFFERENTIATED CELL

This application is a continuation of U.S. application Ser. No. 09/568,254, filed May 10, 2000 which is a continuation-in-part of U.S. application Ser. No. 08/594,164, filed Jan. 31, 1996, now U.S. Pat. No. 6,090,625 which issued on Jul. 18, 2000, and claiming priority from U.K. application No. 9502022.8, filed February 2, 1995, as well as a continuation-in-part of pending U.S. application Ser. No. 09/521,700, filed Mar. 9, 2000 now abandoned as a division of U.S. application Ser. No. 08/594,164 filed Jan. 31, 1996 now U.S. Pat. No. 6,090,625. Each of the foregoing application, and all documents cited in, or during the prosecution of each of the foregoing applications ("appln cited documents") and each document filed by Applicant—either formally or informally—during the prosecution of each of the foregoing applications ("appln prosecution documents"), and each document cited or referenced in each of the appln prosecution documents ("prosecution document references"), and each document cited or referenced in each of the appln cited documents and in each of the prosecution document references, are hereby incorporated herein by reference.

FIELD OF THE INVENTION

The present invention relates to a method of preparing an undifferentiated cell. In particular, the present invention relates to a method of preparing an undifferentiated cell from a more committed cell.

In addition the present invention relates to the use of the undifferentiated cell of the present invention for the preparation of a new more committed cell—i.e. a recommitted cell.

The present invention also relates to the use of the undifferentiated cell of the present invention or the recommitted cell of the present invention to have an effect (directly or indirectly via the use of products obtained therefrom) on the immune system, such as the alleviation of symptoms associated with, or the partial or complete cure from, an immunological condition or disease.

BACKGROUND TO THE INVENTION

Differentiation is a process whereby structures and functions of cells are progressively committed to give rise to more specialised cells, such as the formation of T cells or B cells from immature haemopoietic precursors. Therefore, as the cells become more committed, they become more specialised. In the majority of mammalian cell types, cell differentiation is a one-way process leading ultimately to terminally differentiated cells. However, although some cell types persist throughout life without dividing and without being replaced, many cell types do continue to divide during the lifetime of the organism and undergo renewal. This may be by simple division (e.g. liver cells) or, as in the case of cells such as haemopoietic cells and epidermal cells, by division of relatively undifferentiated stem cells followed by commitment of one of the daughter cells to a programme of subsequent irreversible differentiation. All of these processes, however, have one feature in common: cells either maintain their state of differentiation or become more differentiated. They do not become undifferentiated or even less differentiated.

Retrodifferentiation is a process whereby structures and functions of cells are progressively changed to give rise to less specialised cells. Some cells naturally undergo limited reverse differentiation (retrodifferentiation) in vivo in response to tissue damage. For example, liver cells have been observed to revert to an enzyme expression pattern similar to the foetal enzymic pattern during liver regeneration (Curtin and Snell, 1983, Br. J. Cancer, Vol 48; 495–505).

Jose Uriel (Cancer Research, 1976, vol 36, pp 4269–4275) presented a review on the topic of retrodifferentiation, in which he said:

"retrodifferentiation appears as a common adaptive process for the maintenance of cell integrity against deleterious agents of varied etiology (physical, chemical, and viral). While preserving the entire information encoded on its genome, cells undergoing retrodifferentiation lose morphological and functional complexity by virtue of a process of self-deletion of cytoplasmic structures and the transition to a more juvenile pattern of gene expression. This results in a progressive uniformization of originally distinct cell phenotypes and to a decrease of responsiveness to regulatory signals operational in adult cells. Retrodifferentiation is normally counterbalanced by a process of reontogeny that tends to restore the terminal phenotypes where the reversion started. This explains why retrodifferentiation remains invariably associated to cell regeneration and tissue repair."

Uriel (ibid) then went on to discuss cases of reported retrodifferentiation—such as the work of Gurdon relating to nuclei from gut epithelial cells of Xenopus tadpoles (Advances in Morphogenesis, 1966, vol 4, pp 1–43. New York Academic Press, Eds Abercrombie and Bracher), and the work of Bresnick relating to regeneration of liver (Methods in Cancer Research, 1971, vol 6, pp 347–391).

Uriel (ibid) also reported on work relating to isolated liver parenchymal cells for in vitro cultures. According to Uriel:

"Contrary to the results with fetal or neonatal hepatocytes, with hepatocytes from regenerating liver, or from established hepatomas, it has been difficult to obtain permanent class lines from resting adult hepatocytes."

Uriel (ibid) also reported on apparent retrodifferentiation in cancer, wherein he stated:

"the biochemical phenotypes of many tumours show analogous changes of reversion toward immaturity . . . during the preneoplastic phase of liver carcinogenesis, cells also retrodifferentiate."

More recent findings on retrodifferentiation include the work of Minoru Fukunda (Cancer Research, 1981, vol 41: 4621–4628). Fukunda induced specific changes in the cell surface glycoprotein profile of K562 human leukaemic cells by use of the tumour-promoting phorbol ester, 12-O-tetradecanoyl-phorbol-13-acetate (TPA). According to Fukunda TPA appeared to induce the K562 human leukaemic cells into a retrodifferentiated stage.

Also, Hass et al. (Cell Growth & Differentiation, 1991, vol 2: 541–548) reported that long term culture of TPA-differentiated U-937 leukaemia cells in the absence of phorbol ester for 32–36 days resulted in a process of retrodifferentiation and that the retrodifferentiated cells detached from the substrate and reinitiated proliferation.

As mentioned above, another reported case of retrodifferentiation is the work of Curtin and Snell (Br. J. Cancer, 1983, vol 48: 495–505). These workers compared enzymatic changes occurring during diethylnitrosamine-induced hepatocarcinogenesis and liver regeneration after partial hepatectomy to normal liver differentiation. Theses workers found changes in enzyme activities during carcinogenesis that were similar to a step-wise reversal of differentiation.

According to these workers, their results suggest that an underlying retrodifferentiation process is common to both the process of hepatocarcinogenesis and liver regeneration.

More recently, Chastre et al. (FEBS Letters, 1985, vol 188 (2), pp 2810–2811) reported on the retrodifferentiation of the human colonic cancerous subclone HT29-18.

Even more recently, Kobayashi et al. (Leukaemia Research, 1994, 18 (12): 929–933) have reported on the establishment of a retrodifferentiated cell line (RD-1) from a single rat myelomonocyticleukemia cell which differentiated into a macrophage-like cell by treatment with lipopolysaccharide (LPS).

Much of the above prior art focuses on retrodifferentiation as a stage in carcinogenesis. Several prior art documents refer to experiments where tumour cell lines have apparently been retrodifferentiated. However, these prior art experiments were carried out using tumour cell lines. The situation in genetically aberrant tumour cell lines is not comparable with the normal differentiation pathways. Indeed, it is questionable whether these results indicate true retrodifferentiation in the sense of normal cell lineages. Further, the vast majority of the prior art retrodifferentiated cells were incapable of redifferentiating to a more committed cell, whether of the same lineage, or of any other lineage. One exception is given in Kobayashi et al., 1994, Vol 18; 929–933 where a retrodifferentiated tumour cell line was differentiated into a macrophage-like cell using lipopolysaccharide. However, the retrodifferentiation achieved was very limited and the cells remained committed both before and after treatment.

Similarly, the reverse differentiation seen to occur naturally in liver cells is also very limited and can more accurately be classed as modulations of the differentiated state, that is to say, reversible changes between closely related cell phenotypes.

SUMMARY OF THE INVENTION

Contrary to all earlier teachings, we have now shown that it is possible to treat differentiated cells so that they become undifferentiated cells, including stem cells. These undifferentiated cells are capable of proliferating and giving rise to redifferentiated progeny of the same lineage or any other lineage. We believe that the process responsible for these changes is retrodifferentiation and thus we have now surprisingly found that it is possible to reverse the differentiation process in normal differentiated cells obtained from the human patients to produce a stem cell. Furthermore, in the case of retrodifferentiated haematopoietic cells, these stem cells are pluripotent and can give rise to more than one cell lineage.

The clinical implications of this finding are enormous. Stem cells are extremely difficult to obtain from human patients. They are typically obtained from umbilical tissue, bone marrow or blood where they are present in only very small amounts. However, the present invention provides a method for producing stem cells from more committed cells by the process of retrodifferentiation. Since more committed cells (such as B lymphocytes) are much more abundant in the human body, this technique provides a powerful new method for obtaining stem cells. The haemopoietic stem cells exemplified in the present invention are pluripotent and are therefore capable of redifferentiating along more than one cell lineage Thus, according to a first aspect of the present invention there is provided a method of preparing an undifferentiated cell, the method comprising contacting a more committed cell with an agent that causes the more committed cell to retrodifferentiate into an undifferentiated cell.

In a specific embodiment there is provided a method of increasing the relative number of undifferentiated cells in a cell population including committed cells, which method comprises:

(i) contacting the cell population with an agent that operably engages said committed cells; and (ii) incubating committed cells that are engaged by said agent such that the relative number of undifferentiated cells increases as a result of said engaging.

Preferably, the agent engages a receptor that mediates capture, recognition or presentation of an antigen at the surface of the committed cells. More preferably, the receptor is an MHC class I antigen or an MHC class II antigen, such as a class I antigen selected from Human-Leukocyte-Associated (HLA)-A receptor, an HLA-B receptor, an HLA-C receptor, an HLA-E receptor, an HLA-F receptor or an HLA-G receptor or a class II antigen selected from an HLA-DM receptor, an HLA-DP receptor, an HLA-DQ receptor or an HLA-DR receptor.

Typically, the committed cells are differentiated cells, preferably cells selected from T-cell colony-forming cells (CFC-T cells), B-cell colony-forming cells (CFC-B cells), eosinophil colony-forming cells (CFC-Eosin cells), basophil colony-forming cells (CFC-Bas cells), granulocyte/monocyte colony-forming cells (CFC-GM cells), megakaryocyte colony-forming cells (CFC-MEG cells), erythrocyte burst-forming cells (BFC-E cells), erythrocyte colony-forming cells (CFC-E cells), T cells and B cells.

In one preferred embodiment of the present invention, the more committed cell is not a cancer cell. In another preferred embodiment of the present invention, the agent is neither carcinogenic nor capable of promoting cancer growth.

In a preferred embodiment, the agent is an antibody the receptor, such as a monoclonal antibody to the receptor. Specific examples include CR3/43 and monoclonal antibody TAL.1B5, both of which are commercially available from DakoCytomation A/S, referred to hereafter as "Dako".

Preferably the agent is used in conjunction with a biological response modifier, such as an alkylating agent, for example alkylating agent that is or comprises cyclophosphoamide.

Preferred undifferentiated cells comprises a stem cell antigen. In a preferred embodiment, the undifferentiated cells are selected from an embryonic stem cell, a pluripotent stem cell, a lymphoid stem cell and a myeloid stem cell. Preferably, the undifferentiated cells are characterised by one or more of following cell surface marker designations: $CD34^+$, $HLA-DR^-$, $CD38^-$ and/or CD45low. More preferably the undifferentiated cell is $CD34^+$ and $CD38^-$, even more preferably, $CD34^+$, $CD38^-$, $HLA-DR^-$ and CD45low.

Thus in a preferred embodiment the present invention also provides a method of increasing the relative number of cells having a cell surface marker designation $CD34^+$, $CD38^-$, $HLA-DR^-$ and/or CD45low in a cell population including committed cells, which method comprises:

(i) contacting the cell population with an agent that operably engages said committed cells; and (ii) incubating committed cells that are engaged by said agent such that the relative number of $CD34^+$, $HLA-DR^-$ and/or CD45low cells increases as a result of said engaging.

In another embodiment, the present invention provides a method of inducing committed cells in a cell population to become undifferentiated cells capable of being recommitted into more differentiated cells which method comprises:

(i) contacting the cell population with an agent that operably engages said committed cells; and
(ii) incubating committed cells that are engaged by said agent such that they become undifferentiated cells as a result of said engaging.

In a further embodiment, the present invention provides a method of producing an altered cell population comprising increased numbers undifferentiated cells capable of being recommitted into more differentiated cells, which method comprises:
(i) contacting an initial cell population comprising committed cells with an agent that operably engages said committed cells; and
(ii) incubating committed cells that are engaged by said agent such that they become undifferentiated cells as a result of said engaging, thereby resulting in an altered cell population comprising increased numbers of said undifferentiated cells.

In any of the above methods, an optional step (iii) of enriching said undifferentiated cells or recovering said undifferentiated cells from the altered cell population may be performed. Preferably, step (iii) comprises enriching said undifferentiated cells or recovering said undifferentiated cells from the altered cell population by using a cell surface marker present on the cell surface of the undifferentiated cell or a cell surface marker present on the surface of the committed cells but substantially absent from the cell surface of the undifferentiated cells. Examples of suitable markers include CD34, CD45 and HLA-DR.

In another preferred embodiment, the undifferentiated cell of the invention is CD34$^-$ CD45$^-$ and negative for markers of haemopoeitic lineages.

The undifferentiated cells produced by the methods of the present invention may be subsequently redifferentiated. Accordingly, the present invention provides a method of producing a committed/more differentiated cell which method comprises contacting an undifferentiated cell produced by the methods of the invention with a compound that stimulates differentiation of the undifferentiated cell. Suitable compounds include growth factors, colony stimulating factors and cytokines.

Thus according to a second aspect of the present invention there is provided a method comprising contacting a more committed cell with an agent that causes the more committed cell to retrodifferentiate into an undifferentiated cell; and then committing the undifferentiated cell to a recommitted cell.

The term "recommitted cell" means a cell derived from the undifferentiated cell—i.e. a new more committed cell. "More committed" means more differentiated and can easily be determined by reference to known pathways and stages of cell differentiation.

According to a third aspect of the present invention there is provided an undifferentiated cell produced according to the method of the present invention.

According to a fourth aspect of the present invention there is provided an undifferentiated cell produced according to the method of the present invention as or in the preparation of a medicament.

According to a fifth aspect of the present invention there is provided a recommitted cell produced according to the method of the present invention.

The more differentiated cells may be of the same lineage as the original committed cells or of different lineage.

Thus as well as producing undifferentiated cells, the methods of the present invention can be used to convert cells of one lineage to those of another lineage. Accordingly, in a further aspect the present invention provides a method of inducing in a cell population comprising committed hemopoietic cells of one hemopoietic lineage to become cells of another hemopoietic lineage which method comprises:
(i) contacting the cell population with an agent that engages a receptor that mediates capture, recognition or presentation of an antigen at the surface of said committed hemopoietic cells; and
(ii) incubating committed hemopoietic cells that are engaged by said agent such that they become cells of another hemopoietic lineage as a result of said engaging.

Preferably said committed cells are of a B cell lineage and become cells of another hemopoietic lineage selected from a T cell lineage and a myeloid lineage.

Undifferentiated cells produced according to the methods of the present invention may be used to manufacture a medicaments for the treatment of an immunological disorder or disease. Similarly, recommitted cells produced according to the methods of the present invention may be used to manufacture a medicaments for the treatment of an immunological disorder or disease.

Thus, in its broadest sense, the present invention is based on the highly surprising finding that it is possible to form an undifferentiated cell from a more committed cell.

The present invention is highly advantageous as it is now possible to prepare undifferentiated cells from more committed cells and then use those undifferentiated cells as, or to prepare, medicaments either in vitro or in vivo or combinations thereof for the treatments of disorders.

The present invention is also advantageous as it is possible to commit the undifferentiated cell prepared by retrodifferentiation to a recommitted cell, such as a new differentiated cell, with a view to correcting or removing the original more committed cell or for correcting or removing a product thereof.

Preferably, the more committed cell is capable of retrodifferentiating into an MHC Class I$^+$ and/or an MHC Class II$^+$ undifferentiated cell.

Preferably, the more committed cell is capable of retrodifferentiating into an undifferentiated cell comprising a stem cell antigen.

Preferably, the more committed cell is capable of retrodifferentiating into a CD34$^+$ undifferentiated cell.

Preferably, the more committed cell is capable of retrodifferentiating into a lymphohaematopoietic progenitor cell.

Preferably, the more committed cell is capable of retrodifferentiating into a pluripotent stem cell.

The findings presented herein may also be used to identify further agents that are capable of effecting retrodifferentiation of committed cells to undifferentiated cells. Accordingly, the present invention provides a method for identifying a substance capable of retrodifferentiating a committed/differentiated cell to an undifferentiated cell, which method comprises contacting a population of cells comprising committed cells with a candidate substance and determining whether there is an increase in the relative numbers of undifferentiated cells in said cell population.

Preferably, said increase occurs within 24 hours, preferably 4 to 8 hours (such that any changes cannot be solely accounted for by cell proliferation).

Typically, the determination of changes in the numbers of undifferentiated cells is performed by monitoring changes in the numbers of cell having cell surface markers characteristic of undifferentiated cells. Examples of suitable cell surface markers include CD34$^+$. Alternatively, or in addition, decreases in the numbers of cells having cell surface markers typical of differentiated cells and not undifferentiated cells may be monitored.

Preferably the committed cells used in the assay are committed hemopoietic cells such as cells selected from CFC-T cells, CFC-B cells, CFC-Eosin cells, CFC-Bas cells, CFC-GM cells, CFC-MEG cells, BFC-E cells, CFC-E cells, T cells and B cells, more preferably B cells.

The present invention also provides an agent identified by the assay method of the invention and its use in a retrodifferentiation method of the invention.

DETAILED DESCRIPTION OF THE INVENTION

I. Undifferentiated Cells and Differentiated Cell

Figure 1:
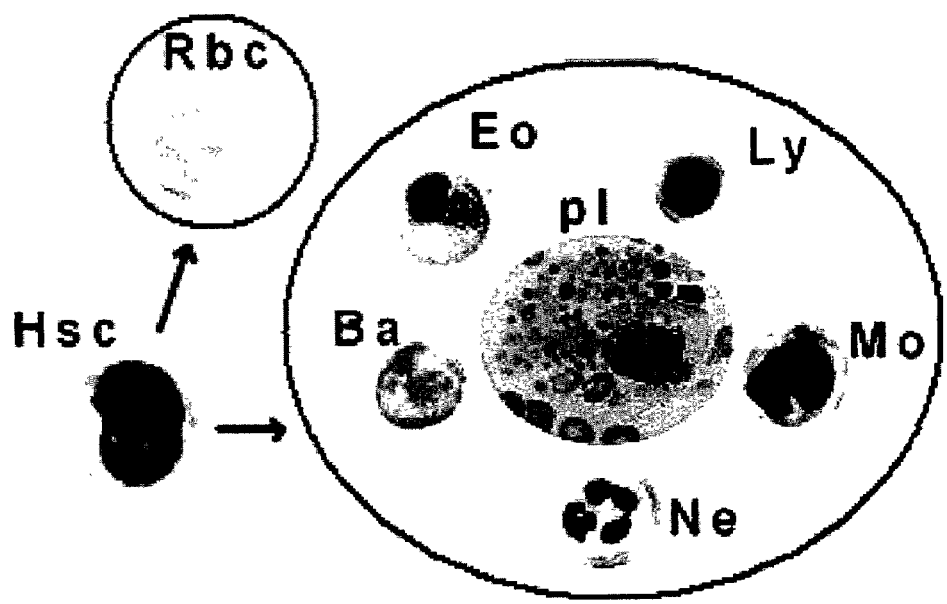
FIG. 1 depicts various haemopoietic cells

There are many undifferentiated cells and differentiated cells found in vivo and the general art is replete with general teachings on them.

By way of example, with respect to cells of the haempoietic cell lineages, reference may be made to inter alia Levitt and Mertelsman 1995 (Haematopoietic Stem Cells, published by Marcel Dekker Inc—especially pages 45–59) and Roitt et al. (Immunology, 4th Edition, Eds. Roitt, Brostoff and Male 1996, Publ. Mosby—especially Chapter 10).

An undifferentiated cell is an immature cell that does not display a mature differentiated character but is capable of yielding progeny that do. A well-known example of an undifferentiated cell is a stem cell.

Stem cells are undifferentiated immature cells, capable of self renewal (division without limit) and differentiation (specialisation). These juvenile cells are abundant in a developing embryo, however, their numbers decrease as development progresses. By contrast, an adult organism contain limited number of stem cells which are confined to certain body compartments.

It is generally believed that stem cells are either monopotent, bipotent or pluripotent. Monopotent and bipotent stem cells are more restricted in development and give rise to one or two types of specialised cells, respectively. In contrast, the pluripotent stem cells (PSCs) can differentiate into many different types of cells, giving rise to tissue (which constitute organs) or in the case of totipotent stem cells, the whole organism.

Pluripotent stem cells, unlike monopotent or bipotent, are capable of multilineage differentiation, giving rise to a tissue which would consist of a collection of cells of different types or lineages.

According to the current understanding, as borne out by the teachings found on page 911 of Molecular Biology of the Cell (pub. Garland Publishers Inc. 1983) and more recently Levitt and Mertelsman (ibid), a stem cell, such as a pluripotent stem cell, has the following four characteristics:

i. it is an undifferentiated cell—i.e. it is not terminally differentiated;

ii. it has the ability to divide without limit;

iii. it has the ability to give rise to differentiated progeny; and iv. when it divides each daughter has a choice: it can either remain as stem cell like its parent or it can embark on a course leading irreversibly to terminal differentiation.

Note should be made of the last qualification, namely that according to the general teachings in the art once an undifferentiated cell has differentiated to a more committed cell it can not then retrodifferentiate. This understanding was even supported by the teachings of Uriel (ibid), Fukunda (ibid), Hass et al (ibid), Curtin and Snell (ibid), Chastre et al (ibid), and Kobayashi et al (ibid) as these workers retrodifferentiated certain types of differentiated cells but wherein those cells remained committed to the same lineage and they did not retrodifferentiate into undifferentiated cells.

Therefore, according to the state of the art before the present invention, it was believed that it was not possible to form undifferentiated cells, such as stem cells, from more committed cells. However, the present invention shows that this belief is inaccurate and that it is possible to form undifferentiated cells from more committed cells.

The Haematopoietic Stem Cell is an example of a pluripotent stem cell which is found among marrow cells and gives rise to all the various blood cells (including leucocytes and erythrocytes).

Blood is a fluid tissue, consisting of Lymphocyte (Ly), Monocytes (Mo), Neutrophils (Ne), Basophils (Ba), Eosinophils (Eso), Platelets (Pl) and Red Blood Cells (Rbc)—see FIG. 1. This specialised tissue is produced by the differentiation of Haematopoietic Stem Cells (Hsc). In general, the white blood cells (inside blue circle) fight infections while red blood cells (inside green circle) transport nutrients, oxygen and waste product around the body.

Previously, haemopoietic stem cells were extracted by isolation from (i) bone marrow, (ii) growth factor mobilised peripheral blood or (iii) cord blood (placenta). Recently, haemopoietic stem cells have been prepared from Embryonic Stem Cells, which are extracted from embryos obtained using in vitro fertilisation techniques. These undifferentiated cells are capable of multi-lineage differentiation and reconstitution of all body tissue i.e. are totipotent.

The above mentioned extraction methods are cumbersome, sometime hazardous and in certain instances can be argued unethical, especially, in the case of the Embryonic Stem Cells extraction method.

There are a number of undifferentiated stem cells of the haemopoietic lineage. These include pluripotent stem cells (PSCs), lymphoid stem cells (LSCs) and myeloid stem cells (MSCs), known collectively as lymphohaematopoietic progenitor cells (LPCs). LSCs and MSCs are each formed by the differentiation of PSCs. Hence, LSCs and MSCs are more committed than PSCs.

Examples of differentiated cells of the haemopoietic lineage include T cells, B cells, eosinophils, basophils, neutrophils, megakaryocytes, monocytes, erythrocytes, granulocytes, mast cells, and lymphocytes.

Figure 2:
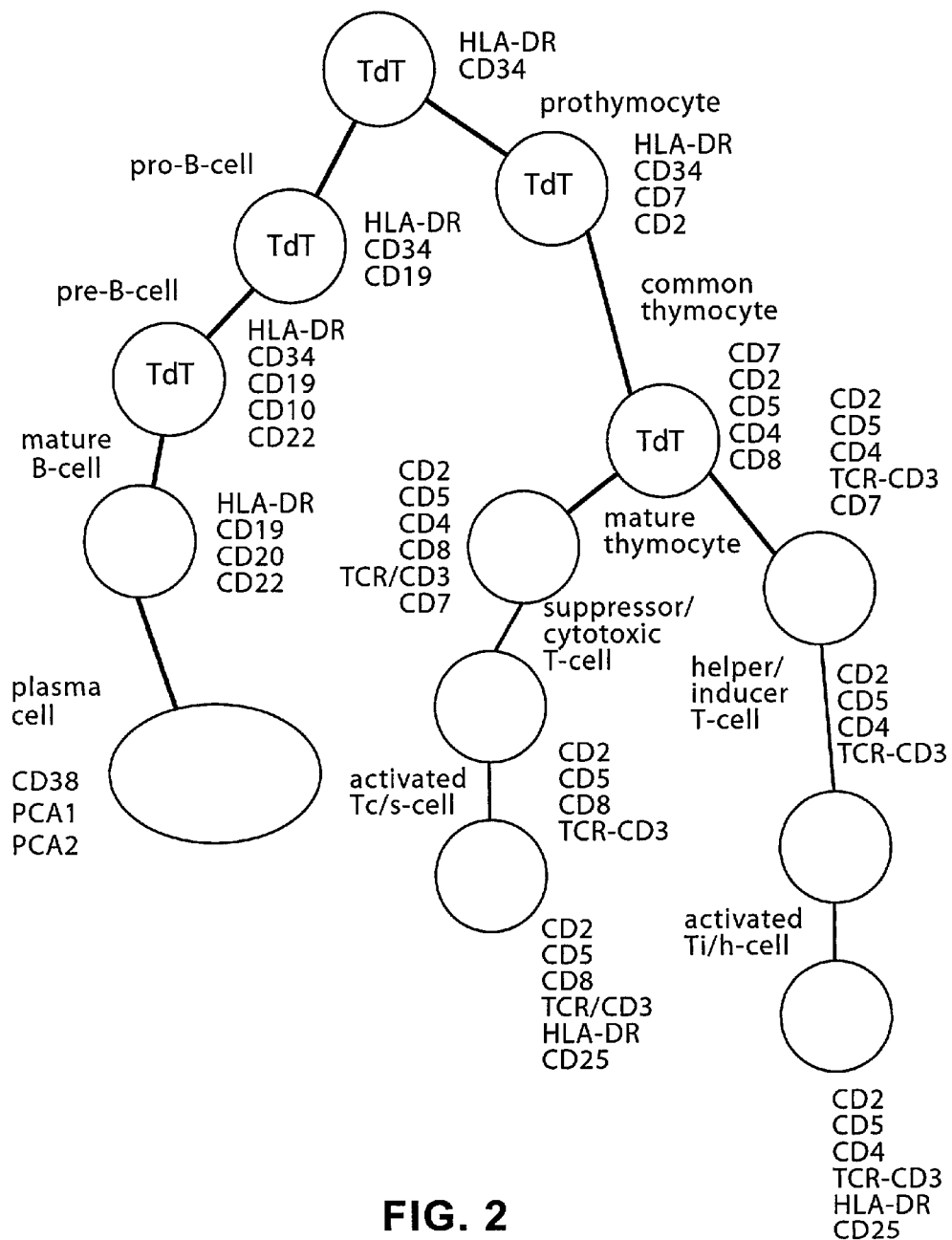
FIG. 2 is a scheme depicting differentiation pathways from lymphoid stem cells.

T cells and B cells are formed by the differentiation of LSCs. Hence, T cells and B cells are more committed than LSCs. In more detail, the chain of differentiation is LSC→pro-B-cell or prothymocyte. Pro-B-cell→pre-B-cell→mature B-cell→plasma cell. Prothymocyte→common thymocyte→mature thymocytes (helper/inducer or cytotoxic/suppressor lineages)—see FIG. 2.

Figure 3:
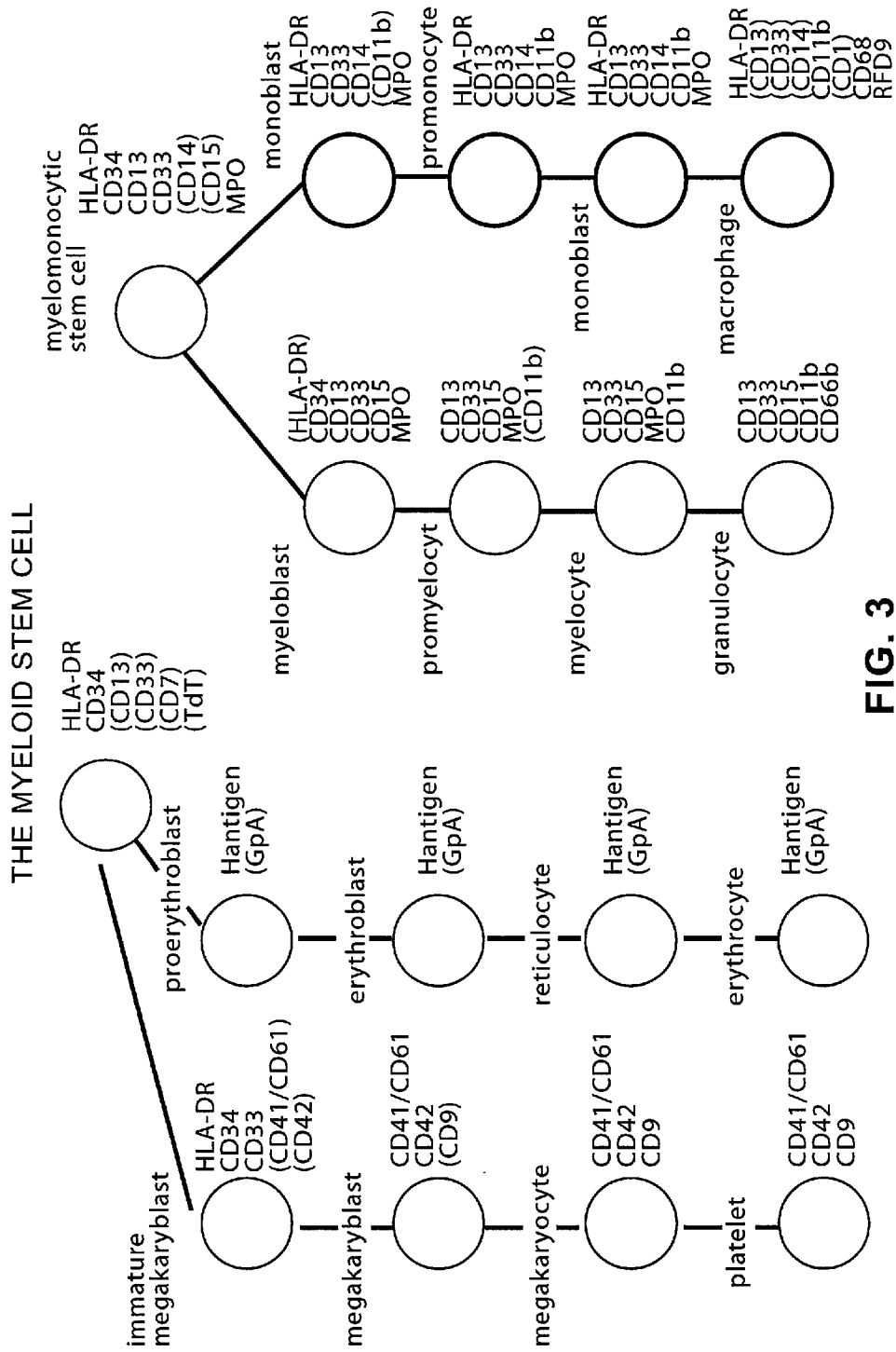
FIG. 3 is a scheme depicting differentiation pathways from myeloid stem cells.
Figure 4:
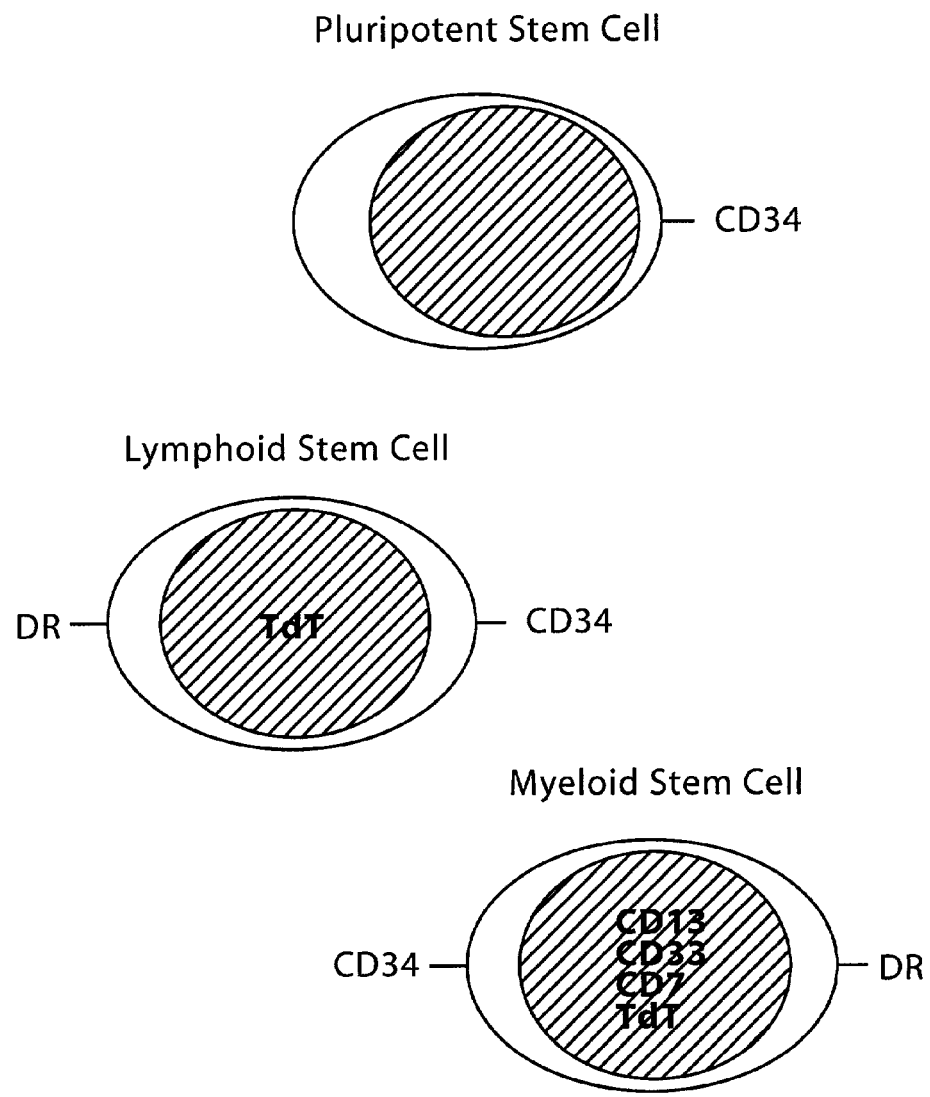
FIG. 4 is a diagram of lymphohaemopoietic progenitor cells.

Eosinophils, basophils, neutrophils, megakaryocytes, monocytes, erythrocytes, granulocytes, mast cells, NKs, and lymphocytes are formed by the differentiation of MSCs. Hence, each of these cells are more committed than MSCs. In more detail, the chain of differentiation is MSC→immature megakaryoblast (→megakaryoblast→megakaryocyte→platelet) or proerythroblast (→erythroblast→reticulocyte→erythrocyte) or myelomonocytic stem cell, a bipotent stem cell that differentiates to either a myeloblast (→promyelocyt→myelocyt→granulocyte) or a monoblast (→promonocyte→monocyte→macrophage)—see FIG. 3.

The pathways of differentiation of haemotopoiesis have thus been extensively characterised and the various cell stages are readily identifiable according to morphology and lineage-specific cell surface markers (see below).

Other stem cells include neural stem cells, multipotent stem cells that can generate neurons, atrocytes and oligodendrocytes (Nakafuku and Nakamura, 1995, J. Neurosci Res., vol 41(2): 153–68; Anderson, 1994, FASEB J., vol 8(10): 707–13; Morshead et al., 1994, Neuron, Vol 13(5): 1071–82). Skeletal muscle satellite cells are another type of stem cell, more specifically a distinct class of myogenic cells that are maintained as quiescent stem cells in the adult and can give rise to new muscle cells when needed (Bischoff, 1986, Dev Biol., vol 115(1): 129–39). Other types of stem cells are epithelial stem cells, a subset of basal cells, and mesenchymal stem cells.

A very important type of stem cells are embryonic stem (ES) cells. These cells have been extensively studied and characterised. Indeed, ES cells are routinely used in the production of transgenic animals. ES cells have been shown to differentiate in vitro into several cell types including lymphoid precursors (Potocnik et al., 1994, EMBO J., vol 13(22): 5274–83) and neural cells. ES cells are characterised by a number of stage-specific markers such as stage-specific embryonic markers 3 and 4 (SSEA-3 and SSEA-4), high molecular weight glycoproteins TRA-1-60 and TRA-1-81 and alkaline phosphatase (Andrews et al., 1984, Hybridoma, vol 3: 347–361; Kannagi et al., 1983, EMBO J., vol 2: 2355–2361; Fox et al., 1984, Dev. Biol., vol 103: 263–266; Ozawa et al., 1985, Cell. Differ., vol 16: 169–173).

Various antigens are associated with undifferentiated and differentiated cells. The term "associated" here means the cells expressing or capable of expressing, or presenting or capable of being induced to present, or comprising, the respective antigen(s).

Most undifferentiated cells and differentiated cells comprise Major Histocompatability Complex (MHC) Class I antigens and/or Class II antigens. If these antigens are associated with those cells then they are called Class I$^+$ and/or Class II$^+$ cells.

Each specific antigen associated with an undifferentiated cell or a differentiated cell can act as a marker. Hence, different types of cells can be distinguished from each other on the basis of their associated particular antigen(s) or on the basis of a particular combination of associated antigens.

Examples of these marker antigens include the antigens CD34, CD19 and CD3. If these antigens are present then these particular cells are called CD34$^+$, CD19$^+$ and CD3$^+$ cells respectively. If these antigens are not present then these cells are called CD34$^-$, CD19$^-$ and CD3$^-$ cells respectively.

In more detail, PSCs are CD34$^+$ DR$^-$ TdT$^-$ cells (other useful markers being CD38$^-$ and CD36$^+$). LSCs are DR$^+$, CD34$^+$ and TdT$^+$ cells (also CD38$^+$). MSCs are CD34$^+$, DR$^+$, CD13$^+$, CD33$^+$, CD7$^+$ and TdT$^+$ cells. B cells are CD19$^+$, CD21$^+$, CD22$^+$ and DR$^+$ cells. T cells are CD2$^+$, CD3$^+$, and either CD4$^+$ or CD8$^+$ cells. Immature lymphocytes are CD4$^+$ and CD8$^+$ cells. Activated T cells are DR$^+$ cells. Natural killer cells (NKs) are CD56$^+$ and CD16$^+$ cells. T lymphocytes are CD7$^+$ cells. Leukocytes are CD45$^+$ cells. Granulocytes are CD13$^+$ and CD33$^+$ cells. Monocyte macrophage cells are CD14$^+$ and DR$^+$ cells. Additional details are provided in FIGS. 2 and 3.

Embryonic stem cells express SSEA-3 and SSEA-4, high molecular weight glycoproteins TRA-1-60 and TRA-1-81 and alkaline phosphatase. They also do not express SSEA-1, the presence of which is an indicator of differentiation. Other markers are known for other types of stem cells, such as Nestein for neuroepithelial stem cells (J. Neurosci, 1985, Vol 5: 3310). Mesenchymal stem cells are positive for SH2, SH3, CD29, CD44, CD71, CD90, CD106, CD120a and CD124, for example, and negative for CD34, CD45 and CD14.

Alternatively, or in addition, many cells can be identified by morphological characteristics. The identification of cells using microscopy, optionally with staining techniques is an extremely well developed branch of science termed histology and the relevant skills are widely possessed in the art. Clearly staining of cells will only be carried out on aliquots of cells to confirm identity since stains in general cause cell death.

Hence, by looking for the presence of the above-listed antigen markers it is possible to identify certain cell types (e.g. whether or not a cell is an undifferentiated cell or a differentiated cell) and the specialisation of that cell type (e.g. whether that cell is a T cell or a B cell).

Undifferentiated cells may comprise any components that are concerned with antigen presentation, capture or recognition. Preferably, the undifferentiated cell is an MHC Class I$^+$ and/or an MHC Class II$^+$ cell.

The more committed cell may comprise any components that are concerned with antigen presentation, capture or recognition. Preferably, the more committed cell is an MHC Class I$^+$ and/or an MHC Class II$^+$ cell.

The more committed cell is any cell derived or derivable from an undifferentiated cell. Thus, in one preferred embodiment, the more committed cell is also an undifferentiated cell. By way of example therefore the more committed undifferentiated cell can be a lymphoid stem cell or a myeloid stem cell, and the undifferentiated cell is a pluripotent stem cell.

In another preferred embodiment, the more committed cell is a differentiated cell, such as a CFC-T cell, a CFC-B cell, a CFC-Eosin cell, a CFC-Bas cell, a CFC-Bas cell, a CFC-GM cell, a CFC-MEG cell, a BFC-E cell, a CFC-E cell, a T cell, a B cell, an eosinophil, a basophil, a neutrophil, a monocyte, a megakaryocyte or an erythrocyte; and the undifferentiated cell is a myeloid stem cell, a lymphoid stem cell or a pluripotent stem cell.

If the more committed cell is a differentiated cell then preferably the differentiated cell is a B lymphocyte (activated or non-activated), a T lymphocyte (activated or non-activated), a cell from the macrophage monocyte lineage, a nucleated cell capable of expressing class I or class II antigens, a cell that can be induced to express class I or class II antigens or an enucleated cell (i.e. a cell that does not contain a nucleus—such as a red blood cell).

In alternative preferred embodiments, the differentiated cell is selected from any one of a group of cells comprising large granular lymphocytes, null lymphocytes and natural killer cells, each expressing the CD56 and/or CD16 cell surface receptors.

The differentiated cell may even be formed by the nucleation of an enucleated cell.

II. Agents

The agent operably engages the more committed cell in order to retrodifferentiate that cell into an undifferentiated cell. In this regard, the agent for the retrodifferentiation of the more committed cell into the undifferentiated cell may act in direct engagement or in indirect engagement with the more committed cell.

The agent may act intracellularly within the more committed cell. However, preferably, the agent acts extracellularly of the more committed cell.

An example of direct engagement is when the more committed cell has at least one cell surface receptor on its cell surface, such as a β-chain having homologous regions (regions that are commonly found having the same or a similar sequence) such as those that may be found on B cells, and wherein the agent directly engages the cell surface receptor. Another example, is when the more committed cell has a cell surface receptor on its cell surface such as an α-chain having homologous regions such as those that may be found on T cells, and wherein the agent directly engages the cell surface receptor.

An example of indirect engagement is when the more committed cell has at least two cell surface receptors on its cell surface and engagement of the agent with one of the receptors affects the other receptor which then induces retrodifferentiation of the more committed cell.

The agent for the retrodifferentiation of the more committed cell into an undifferentiated cell may be a chemical compound or composition. Preferably, however, the agent is capable of engaging a cell surface receptor on the surface of the more committed cell. Thus, in a preferred embodiment, the agent operably engages a receptor present on the surface of the more committed cell—which receptor may be expressed by the more committed cell, such as a receptor that is capable of being expressed by the more committed cell.

For example, preferred agents include any one or more of cyclic adenosine monophosphate (cAMP), a CD4 molecule, a CD8 molecule, a part or all of a T-cell receptor, a ligand (fixed or free), a peptide, a T-cell receptor (TCR), an antibody, a cross-reactive antibody, a monoclonal antibody, or a polyclonal antibody. Growth factors may also be used, such as haemopoietic growth factors, for example erythropoietin and granulocyte-monocyte colony stimulating factor (GM-CSF).

If the agent is an antibody, a cross-reactive antibody, a monoclonal antibody, or a polyclonal antibody, then preferably the agent is any one or more of an antibody, a cross-reactive antibody, a monoclonal antibody, or a polyclonal antibody to any one or more of: the β chain of a MHC class II antigen, the β chain of a MHC HLA-DR antigen, the α chain of a MHC class I or class II antigen, the α chain of HLA-DR antigen, the α and the β chain of MHC class II antigen or of a MHC class I antigen. An example of a suitable antibody is CR3/43 (supplied by Dako).

The term "antibody" includes the various fragments (whether derived by proteolytic cleavage or recombinant technology) and derivatives that retain binding activity, such as Fab, F(ab')$_2$ and scFv antibodies, as well as mimetics or bioisosteres thereof. Also included as antibodies are genetically engineered variants where some of the amino acid sequences have been modified, for example by replacement of amino acid residues to enhance binding or, where the antibodies have been made in a different species to the organism whose cells it is desired to treat according to the methods of the invention, to decrease the possibility of adverse immune reactions (an example of this is 'humanised' mouse monoclonal antibodies).

Agents used to effect the conversion of a more committed cell to an undifferentiated cell preferably act extracellularly of the more committed cell. In particular, it is preferred that the more committed cell comprises a receptor that is operably engageable by the agent and the agent operably engages the receptor.

For example the receptor may be a cell surface receptor. Specific examples of cell surface receptors include MHC class I and class II receptors. Preferably, the receptor comprises an α-component and/or a β-component, as is the case for MHC class I and class II receptors.

More preferably, the receptor comprises a β-chain having homologous regions, for example at least the homologous regions of the β-chain of HLA-DR.

Alternatively, or in addition, the receptor comprises an α-chain having homologous regions, for example at least the homologous regions of the α-chain of HLA-DR.

Preferably, the receptor is a Class I or a Class II antigen of the major histocompatibility complex (MHC). In preferred embodiments the cell surface receptor is any one of: an HLA-DR receptor, a DM receptor, a DP receptor, a DQ receptor, an HLA-A receptor, an HLA-B receptor, an HLA-C receptor, an HLA-E receptor, an HLA-F receptor, or an HLA-G receptor. In more preferred embodiments the cell surface receptor is an HLA-DR receptor.

Preferably, the agent is an antibody to the receptor, more preferably the agent is a monoclonal antibody to the receptor.

Another preferred example of an agent is one that modulates MHC gene expression such as MHC Class I$^+$ and/or MHC Class II$^+$ expression.

In a preferred embodiment, the agent is used in conjunction with a biological response modifier. Examples of biological response modifiers include an alkylating agent, an immunomodulator, a growth factor, a cytokine, a cell surface receptor, a hormone, a nucleic acid, a nucleotide sequence, an antigen or a peptide. A preferred alkylating agent is or comprises cyclophosphoamide.

Other preferred biological response modifiers include compounds capable of upregulating MHC class I and/or class II antigen expression. In a preferred embodiment, this is so as to allow an agent that binds to an MHC receptor to work more effectively. Since any cell type can be made to express MHC class I and/or class II antigens, this should provide a method for retrodifferentiation a wide variety of cell types whether they constitutively express class I and/or class II MHC antigens or not.

III. Methods for Retrodifferentiating Cells

In the methods of the invention, a population of cells comprising committed cells is contacted with an agent that operably engages one or more committed cell in the population. The cell population is then incubated so as to allow those cells that have been operably engaged by the agent to progress through the retrodifferentiation process and ultimately become undifferentiated.

Preferably the contacting step comprises the agent engaging with any one or more of the following: homologous regions of the α-chain of class I antigens, homologous regions of the α-chain of class II antigens, a CD4 cell surface receptor, a CD8 cell surface receptor, homologous regions of the β-chain of class II antigens in the presence of lymphocytes, homologous regions of the α-chain of class I antigens in the presence of lymphocytes, or homologous regions of the α-chain of class II antigens in the presence of lymphocytes. Preferably the contacting step occurs in the presence of the biological response modifier (see above).

Typically, the population of cells is derived from a biological sample, such as blood or related tissues including bone marrow, neuronal tissue from the central nervous system or peripheral nervous system, or muscle tissue. Preferably biological material is of post-natal origin. It is preferred to use whole blood or processed products thereof, such as plasma, since their removal from subjects can be carried out with the minimum of medical supervision. Blood samples are typically treated with anticoagulents such as heparin or citrate. Cells in the biological sample may be treated to enrich certain cell types, remove certain cell types or dissociate cells from a tissue mass. Useful methods for purifying and separating cells include centrifugation (such as density gradient centrifugation), flow cytometry and affinity chromatography (such as the use of magnetic beads comprising monoclonal antibodies to cell surface markers or panning). By way of example, Ficoll-Hypaque separation is useful for removing erythrocytes and granulocytes to leave mononuclear cells such as lymphocytes and monocytes.

Since the cells are essentially primary cultures, it may necessary to supplement populations of cells with suitable nutrients to maintain viability. Suitable culture conditions are known by the skilled person in the art. Nonetheless, treatment of cell populations is preferably initiated as soon as possible after removal of biological samples from patients, typically within 12 hours, preferably within 2 to 4 hours. Cell viability can be checked using well known techniques such as trypan blue exclusion.

Cell populations are generally incubated with an agent for at least two hours, typically between 2 and 24 hours, preferably between 2 and 12 hours. Incubations are typically performed at from about room temperature, for example about 22° C., up to about 37° C. including 33° C. The progress of the retrodifferentiation procedure can be checked periodically by removing a small aliquot of the sample and examining cells using microscopy and/or flow cytometry.

Once the relative numbers of the desired cell type have increased to a suitable level, which may for example be as low as 0.1% or as high as 5%, the resulting altered cell populations may be used in a number of ways. With respect to the numbers of undifferentiated cells formed, it is important to appreciate the proliferative ability of stem cells. Although under some circumstance, the numbers of stem cells or other undifferentiated cells formed may appear to be low, studies have shown that only 50 pluripotent haemopoietic stem cells can reconstitute an entire haemopoietic system in a donor mouse. Thus therapeutic utility does not require the formation of a large number of cells by the methods of the invention.

Conversion of more committed cells to undifferentiated cells may also be carried out in vivo by administration of the agent, admixed with a pharmaceutically carrier or diluent, to a patient. However it is preferred in many cases that retrodifferentiation is performed in vitro/ex vivo.

Treated populations of cells obtained in vitro may be used subsequently with minimal processing. For example they may be simply combined with a pharmaceutically acceptable carrier or diluent and administered to a patient in need of stem cells.

It may however be desirable to enrich the cell population for the undifferentiated cells or purify the cells from the cell population. This can conveniently be performed using a number of methods. For example cells may be purified on the basis of cell surface markers using chromatography and/or flow cytometry. Nonetheless, it will often be neither necessary nor desirable to extensively purify undifferentiated cells from the cell population since other cells present in the population (for example stromal cells) may maintain stem cell viability and function.

Flow cytometry is a well-established, reliable and powerful technique for characterizing cells within mixed populations as well as for sorting cells. Flow cytometry operates on the basis of physical characteristics of particles in liquid suspension, which can be distinguished when interrogated with a beam of light. Such particles may of course be cells. Physical characteristics include cell size and structure or, as has become very popular in recent years, cell surface markers bound by monoclonal antibodies conjugated to fluorescent molecules.

Kreisseg et al., 1994, J. Hematother 3(4): 263–89, state, "Because of the availability of anti-CD34 monoclonal antibodies, multiparameter flow cytometry has become the tool of choice for determination of haemapoietic stem and progenitor cells" and goes on to describe general techniques for quantitation and characterisation of CD34-expressing cells by flow cytometry. Further, Korbling et al., 1994, Bone Marrow Transplant. 13: 649–54, teaches purification of CD34$^+$ cells by immunoadsorption followed by flow cytometry based on HLA-DR expression. As discussed above, CD34$^+$ is a useful marker in connection with stem cells/progenitor cells.

Flow cytometry techniques for sorting stem cells based on other physical characteristics are also available. For example, Visser et al., 1980, Blood Cells 6:391–407 teach that stem cells may be isolated on the basis of their size and degree of structuredness. Grogan et al., 1980, Blood Cells, 6: 625–44 also teach that "viable stem cells may be sorted from simple haemapoietic tissues in high and verifiable purity".

As well as selecting for cells on the basis of the presence of a cell surface marker or other physical property (positive selection), cell populations may be enriched, purified using negative criteria. For example, cells that possess lineage specific markers such as CD4, CD8, CD42 and CD3 may be removed from the cell population by flow cytometry or affinity chromatography.

A very useful technique for purifying cells involves the use of antibodies or other affinity ligands linked to magnetic beads. The beads are incubated with the cell population and cells that have a cell surface marker, such as CD34, to which the affinity ligand binds are captured. The sample tube containing the cells is placed in a magnetic sample concentrator where the beads are attracted to the sides of the tube. After one or more wash stages, the cells of interest have been partially or substantially completely purified from other cells. When used in a negative selection format, instead of washing cells bound to the beads by discarding the liquid phase, the liquid phase is kept and consequently, the cells bound to the beads are effectively removed from the cell population.

These affinity ligand-based purification methods can be used with any cell type for which suitable markers have been characterized or may be characterized.

Urbankova et al., 1996. (J. Chromatogr B Biomed Appl. 687: 449–52) teaches the micropreparation of hemopoietic stem cells from a mouse bone marrow suspension by gravitational field-flow fractionation. Urbankova et al., 1996, further comments that the method was used for the chacterization of stem cells from mouse bone marrow because these cells are bigger than the other cells in bone marrow and it is therefore possible to separate them from the mixture. Thus physical parameters other than cell surface markers may be used to purify/enrich for stem cells.

Cell populations comprising undifferentiated cells and purified undifferentiated cells produced by the methods of the invention may be maintained in vitro using known techniques. Typically, minimal growth media such as Hanks, RPMI 1640, Dulbecco's Miminal Essential Media (DMEM) or Iscove's Modified Dulbecco Medium are used, supplemented with mammalian serum such as FBS, and optionally autologous plasma, to provide a suitable growth environment for the cells. In a preferred embodiment, stem cells are cultured on feeder layers such as layers of stromal cells (see Deryugina et al., 1993, Crit Rev. Immunology, vol 13: 115–150). Stromal cells are believed to secrete factors that maintain progenitor cells in an undifferentiated state. A long term culture system for stem cells is described by Dexter et al., 1977 (J. Cell Physiol, vol 91: 335) and Dexter et al., 1979 (Acta. Haematol., vol 62: 299).

For instance, Lebkowski et al., 1992 (Transplantation 53(5): 1011–9) teaches that human CD34$^+$ haemopoietic cells can be purified using a technology based on the use of monoclonal antibodies that are covalently immobilised on polystyrene surfaces and that the CD34$^+$ cells purified by this process can be maintained with greater than 85% viability. Lebkowski et al., 1993 (J. Hematother, 2(3): 339–42) also teaches how to isolate and culture human CD34$^+$ cells. See also Haylock et al., 1994 (Immunomethods, vol 5(3): 217–25) for a review of various methods.

Confirmation of stem cell identity can be performed using a number of in vitro assays such as CFC assays (see also, the examples). Very primitive haemopoietic stem cells are often measured using the long-term culture initiating cell (LTC-IC) assay (Eaves et al, 1991, J. Tiss. Cult. Meth. Vol 13: 55–62). LTC-ICs sustain haemopoiesis for 5 to 12 weeks.

Cell populations comprising undifferentiated cells and purified preparations of comprising undifferentiated cells may be frozen for future use. Suitable techniques for freezing cells and subsequently reviving them are known in the art.

IV. Methods for Recommitting Undifferentiated Cells

One important application of undifferentiated cells of the present invention is in the reconstitution of tissues, for example nervous tissue or haemopoietic cells. This involves differentiating the undifferentiated cells produced by the methods of the invention. This may be carried out by simply administering the undifferentiated cells to a patient, typically at a specific site of interest such as the bone marrow or spinal cord, and allowing the natural physiological conditions within the patient to effect differentiation. A specific example of this is the reconstitution or supplementation of the haemopoietic system, for example in the case of AIDS patients with reduced number of CD4$^+$ lymphocytes.

Alternatively, differentiation (also termed "recommitting", herein) can be effected in vitro and expanded cells then, for example, administered therapeutically. This is generally performed by administering growth factors. For example, retinoic acid has been used to differentiate ES cells into neuronal cells. Methylcellulose followed by co-culture with a bone marrow stromal line and IL-7 has been used to differentiate ES cells into lymphocyte precursors (Nisitani et al., 1994, Int. Immuno., vol 6(6): 909–916). Bischoff, 1986 (Dev. Biol., vol 115(1): 129–39) teaches how to differentiate muscle satellite cells into mature muscle fibres. Neural precursor cells can be expanded with basic fibroblast growth factor and epidermal growth factor (Nakafuku and Nakamura, 1995, J. Neurosci. Res., vol 41(2): 153–168). Haemopoietic stem cells can be expanded using a number of growth factors including GM-CSF, erythropoeitin, stem cell factor and interleukins (IL-1, IL-3, IL-6)—see Metcalf, 1989 (Nature, vol 339: 27–30) for a review of these various factors.

Potocnik et al., 1994 (EMBO J., vol 13(22): 5274–83) even demonstrated the differentiation of ES cells to haemopoietic cells using low oxygen (5%) conditions.

Thus, in a preferred embodiment of the present invention the undifferentiated cell is then committed into a recommitted cell, such as a differentiated cell. The recommitted cell may be of the same lineage to the more committed cell from which the undifferentiated cell was derived. Alternatively, the recommitted cell may be of a different lineage to the more committed cell from which the undifferentiated cell was derived. For example, a B lymphocyte may be retrodifferentiated to a CD34$^+$ CD38$^-$ HLA-DR$^-$ stem cell. The stem cell may be subsequently recommitted along a B cell lineage (the same lineage) or a lymphoid lineage (different lineage).

V. Assays for Identifying Retrodifferentiating Agents

In addition to the agents mentioned above, further suitable agents may be identified using assay methods of the invention. Thus, the present invention provides a method for identifying a substance capable of retrodifferentiating a committed/differentiated cell to an undifferentiated cell, which method comprises contacting a population of cells comprising committed cells with a candidate substance and determining whether there is an increase in the relative numbers of undifferentiated cells in said cell population.

Suitable candidate substances include ligands that bind to cell surface receptors such as antibody products (for example, monoclonal and polyclonal antibodies, single chain antibodies, chimeric antibodies and CDR-grafted antibodies), such as antibodies that bind to cell surface receptors. Cell surface receptors of particular interest are described above and include MHC receptors and surface proteins of with CD designations, such as CD4 and CD8. Other ligands that bind to cell surface receptors include growth factors.

Furthermore, combinatorial libraries, peptide and peptide mimetics, defined chemical entities, oligonucleotides, and natural product libraries may be screened for activity as retrodifferentiation agents. The candidate substances may be used in an initial screen in batches of, for example 10 substances per reaction, and the substances of those batches which show inhibition tested individually.

A typical assay comprises placing an aliquot of cells comprising committed cells in a suitable vessel such as a multiwell plate. A candidate substance is added to the well and the cells incubated in the well. Incubations are typically performed at from about room temperature, for example about 22° C., up to about 37° C. including 33° C.

Retrodifferentiation may be measured by removing a small aliquot of cells and examining the cells by microscopy and/or flow cytometry to determine whether there has been a change in the numbers of undifferentiated cells. Typically, the determination of changes in the numbers of undifferentiated cells is performed by monitoring changes in the numbers of cell having cell surface markers characteristic of undifferentiated cells, although morphological changes may also be used as a guide. Examples of suitable cell surface markers include $CD34^+$. Alternatively, or in addition, decreases in the numbers of cells having cell surface markers typical of differentiated cells and not undifferentiated cells may be monitored, for example a reduction in the relative numbers of cells possessing lineage specific markers such as CD3, CD4 and CD8

Preferably, any increase in the numbers of cells having characteristics typical of undifferentiated cells occurs within 24 hours, preferably 4 to 8 hours, such that any changes cannot be solely accounted for by cell proliferation.

It may be desirable to prescreen for agents that bind to, for example, cell surface receptors, such as MHC class I or class II receptors. Any agents identified as binding to target cell surface receptors may then be used in the above assay to determine their effect on retrodifferentiation. As a particular example, phage display libraries which express antibody binding domains may be used to identify antibody fragments (typically scFvs) that bind to a target cell surface marker, such as the homologous region of the β-chain of MHC class II receptors. Suitable binding assays are known in the art, as is the generation and screening of phage display libraries. Assays may also be used to identify optimised antibodies or antibody fragments, for example to screen a mutagenised library of derivatives of an antibody already shown to effect retrodifferentiation.

VI. Uses

The present invention provides methods of retrodifferentiating committed cells to undifferentiated cells. In particular, the present invention provides a method for preparing a stem cell from a more differentiated cell. The clinical implications of this are enormous since stem cells are being used in a wide variety of therapeutic applications but up until now were difficult, cumbersome and sometimes ethically controversial to obtain.

Stem cells produced according to the present invention may be used to repopulate specific cell populations in a patient, such as a haemopoietic cell population or a subpopulation thereof, such as CD4 T-lymphocytes. The more committed cells used to produce the stem cells may be from the same patient or a matched donor. Thus stem cells produced according to the present invention may be used to heal and reconstitute specialised cell tissue and organs.

Thus, the present invention also encompasses a medicament comprising an undifferentiated cell prepared by any one of these processes admixed with a suitable diluent, carrier or excipient.

In one embodiment, the medicament comprising the undifferentiated cell may be used produce a beneficial more committed cell, such as one having a correct genomic structure, in order to alleviate any symptoms or conditions brought on by or associated with a more committed cell having an incorrect genomic structure. Thus, the present invention also provides a process of removing an acquired mutation from a more committed cell wherein the method comprises forming an undifferentiated cell by the method according to the present invention, committing the undifferentiated cell into a recommitted cell, whereby arrangement or rearrangement of the genome and/or nucleus of the cell causes the mutation to be removed.

Preferably the gene is inserted into the immunoglobulin region or TCR region of the genome.

The present invention also provides a method of treating a patient suffering from a disease or a disorder resulting from a defective cell or an unwanted cell, the method comprising preparing an undifferentiated cell by contacting a more committed cell with an agent that causes the more committed cell to retrodifferentiate into the undifferentiated cell, and then optionally committing the undifferentiated cell into a recommitted cell; wherein the undifferentiated cell, or the recommitted cell, affects the defective cell or the unwanted cell to alleviate the symptoms of the disease or disorder or to cure the patient of the disease or condition.

Alternatively, the undifferentiated cell could be used to produce a more committed cell that produces an entity that cures any symptoms or conditions brought on by or associated with a more committed cell having an incorrect genomic structure.

For example, the present invention may be used to prepare antibodies or T cell receptors to an antigen that is expressed by the more committed cell which has retrodifferentiated into the undifferentiated cell. In this regard, the antigen may be a fetospecific antigen or a cross-reactive fetospecific antigen.

The present invention also includes a process of controlling the levels of undifferentiated cells and more committed cells. For example, the present invention includes a method comprising forming an undifferentiated cell by the method according to the present invention and then activating an apoptosis gene to affect the undifferentiated cell, such as bring about the death thereof.

In a preferred embodiment the present invention relates to a process of introducing a gene into the genome of an undifferentiated cell, wherein the process comprises introducing the gene into a more committed cell, and then preparing an undifferentiated cell by the method according to the present invention, whereby the gene is present in the undifferentiated cell.

In a more preferred embodiment the present invention relates to a process of introducing a gene into the genome of an undifferentiated cell, wherein the process comprises inserting the gene into the genome of a more committed cell, and then preparing an undifferentiated cell by the method according to the present invention, whereby the gene is present in the undifferentiated cell.

The gene may be a gene that renders the undifferentiated cell and more differentiated cells obtained therefrom more resistant to pathogenic infections such as a viral infection. In particular, by way of example, B lymphocytes from AIDS patients may be used to produce stem cells that are then engineered to be resistant to HIV infection. When expanded and introduced into the patients, the resulting helper T lymphocytes may also be resistant to HIV infection.

In an alternative embodiment the present invention relates to a process of introducing a gene into an undifferentiated cell, wherein the process comprises inserting the gene into the genome of a more committed cell, and then preparing an undifferentiated cell by the method according to the present invention, whereby the gene is present in the genome of the undifferentiated cell.

In addition, the present invention also encompasses the method of the present invention for preparing an undifferentiated cell, wherein the method includes committing the undifferentiated cell into a recommitted cell and then fusing the recommitted cell to a myeloma. This allows the expression in vitro of large amounts of the desired product, such as an antibody or an antigen or a hormone etc.

The present invention encompasses an undifferentiated cell prepared by any one of these processes of the present invention.

Other aspects of the present invention include:

The use of any one of the agents of the present invention for preparing an undifferentiated cell from a more committed cell.

The use of an undifferentiated cell produced according to the method of the present invention for producing any one of a monoclonal or a polyclonal or a specific antibody from a B-lymphocyte or a T-lymphocyte; a cell from the macrophage monocyte lineage; a nucleated cell capable of expressing class I or class II antigens; a cell capable of being induced to express class I or class II antigens; an enucleated cell; a fragmented cell; or an apoptic cell.

The use of an undifferentiated cell produced according to the method of the present invention for producing effector T-lymphocytes from B-lymphocytes and/or vice versa.

The use of an undifferentiated cell produced according to the method of the present invention for producing any one or more of: a medicament, such as a medicament comprising or made from a B-lymphocyte, a T-lymphocyte, a cell from the macrophage monocyte lineage, a nucleated cell capable of expressing a class I or a class II antigen, a cell capable of being induced to express a class I or a class II antigen, or an enucleated cell.

The present invention also encompasses processes utilising the afore-mentioned uses and products or compositions prepared from such processes.

The present invention also encompasses a medicament comprising an undifferentiated cell according to the present invention or a product obtained therefrom admixed with a suitable diluent, carrier or excipient.

In one preferred embodiment the medicament comprises an antibody or antigen obtained from an undifferentiated cell according to the present invention admixed with a suitable diluent, carrier or excipient.

Preferably the medicament is for the treatment of any one of: cancer, autoimmune diseases, blood disorders, cellular or tissue regeneration, organ regeneration, the treatment of organ or tissue transplants, or congenital metabolic disorders.

The methods of the invention and products obtained by those methods, such as undifferentiated cells, may be used in research, for example to study retrodifferentiation, differentiation and identify and study new developmental antigens and cluster differentiation antigens.

VII. Administration

Stem cells and recommitted cells of the present invention, as well as agents shown to retrodifferentiate cells, may be used in therapeutic methods. Preferably the cells or agents of the invention are combined with various components to produce compositions of the invention. More preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The composition of the invention may be administered by direct injection. The composition may be formulated for parenteral, intramuscular, intravenous, subcutaneous, intraocular, oral or transdermal administration.

Compositions comprising cells are typically delivered by injection or implantation. Cells may be delivered in suspension or embedded in a support matrix such as natural and/or synthetic biodegradable matrices. Natural matrices include collagen matrices. Synthetic biodegradable matrices include polyanhydrides and polylactic acid. These matrices provide support for fragile cells in vivo and are preferred for non-haemopoetic cells.

Delivery may also be by controlled delivery i.e. over a period of time which may be from several minutes to several hours or days. Delivery may be systemic (for example by intravenous injection) or directed to a particular site of interest.

Cells are typically administered in doses of from $1 \times 10^5$ to $1 \times 10^7$ cells per kg. For example a 70 kg patient may be administered $14 \times 10^6$ CD34$^+$ cells for reconstitution of haemopoietic tissues.

The routes of administration and dosages described are intended only as a guide since a skilled practitioner will be able to determine readily the optimum route of administration and dosage for any particular patient and condition.

The present invention will now be described by way of examples, which are illustrative only and non-limiting.

A. Materials and Methods

Patients

Blood samples were obtained in lavender top tubes containing EDTA from patients with B-cell chronic lymphocytic leukaemias, patients with antibody deficiency (including IgA deficiency and X-linked infantile hypogammaglobulinaemias), patients with HIV infections and AIDS syndrome, a patient with CMV infection, a patient with Hodgkin's lymphomas, a patient with acute T-cell leukaemia, a 6-days old baby with blastcytosis, various patients with various infections and clinical conditions, cord blood, bone marrow's, and enriched B-lymphocyte preparations of healthy blood donors.

Clinical and Experimental Conditions

The clinical and experimental treatment conditions of patients, including various types of treatment applied to their blood samples, are described in Table 1. Differential white blood cell (WBC) counts were obtained using a Coulter Counter and these are included in the same Table.

Treatment of Blood

Blood samples, once obtained, were treated with pure monoclonal antibody to the homologous region of the β-chain of the HLA-DR antigen (DAKO) and left to mix on a head to head roller at room temperature for a maximum of 24 hours. Some samples were mixed first on a head to head roller for 15 minutes after which they were left to incubate in an incubator at 22° C. The concentration of monoclonal antibody added to blood samples varied from 10–50 μl/ml of blood.

In addition, other treatments treatments were applied at the same concentrations and these included addition of a monoclonal antibody to the homologous of the α-chain of the HLA-DR antigen, a monoclonal antibody to the homologous region of class I antigens, a monoclonal antibody to CD4, a monoclonal antibody to CD8, and a PE conjugated monoclonal antibody to the homologous region of the β-chain of the HLA-DR antigen.

Other treatments included the simultaneous addition of monoclonal antibodies to the homologous regions of the α and β-chains of the HLA-DR antigen to blood samples.

Furthermore, alkylating agents such as cyclophosphoamide were added to blood samples in combination with pure monoclonal antibody to the homologous region of the β-chain of the HLA-DR antigen.

Following these treatments blood samples were stained with panels of labelled monoclonal antibodies as instructed by the manufacturer's instructions and then analyzed using flow cytometry.

Incubation periods with monoclonal antibodies ranged from 2 hour, 4 hour, 6 hour, 12 hour to 24 hour intervals.

Labelled Antibodies

The following monoclonal antibodies were used to detect the following markers on cells by flow cytometry: CD19 and CD3, CD4 and CD8, DR and CD3, CD56 & 16 and CD3, CD45 and CD14, CD8 and CD3, CD8 and CD28, simultest control (IgG1 FITC+IgG2a PE), CD34 and CD2, CD7 and CD13 & 33, CD10 and CD25, CD5 and CD10, CD5 and CD21, CD7 and CD5, CD13 and CD20, CD23 and CD57 and CD25 and CD45 RA (Becton & Dickenson and DAKO).

Each patient's blood sample, both treated and untreated, was analyzed using the majority of the above panel in order to account for the immunophenotypic changes that accompanied different types of treatments and these were carried out separately on different aliquots of the same blood sample. Untreated samples and other control treatments were stained and analyzed simultaneously.

Flow Cytometry

Whole blood sample was stained and lysed according to the manufacturer instructions. Flow cytomery analysis was performed on a FACScan@ with either simultest or PAINT A GATE software (BDIS) which included negative controls back tracking. 10,000 to 20,000 events were acquired and stored in list mode files.

Morphology

Morphology was analyzed using microscopy and Wright's stain.

Preparing Stem Cells from Enriched or Purified B-CLL (or Normal) Lymphocytes:

Aseptic techniques should be used throughout the following procedures:

(A) Mononuclear Cell Separation:

(i) Obtain mononuclear cells from peripheral blood samples by centrifugation on Histopaque, Lymphoprep, or any Lymphocyte separation medium (sp. grav 1.077) for 30 mins at 400 g.

(ii) Collect mononuclear cells in a 50 ml conical tube and wash with 30 mls of Hank's balanced salt solution ($Ca^{2+}$ and $Mg^+$ free, Sigma) containing 2% FCS and 2 mM EDTA or 0.6% citrate.

(iii) After washing, count cells and assess viability using trypan blue and haemocytometer.

(iv) If B-cell count is high, above 70% ($20 \times 10^9$/L, WBC), proceed straight to B (vi).

(v) If B-cell count is low, below 70% ($20 \times 10^9$/L, WBC). Perform negative selection using Macs microbeads or Facs-Vantage purification technique, as described below in Section 1. C.

(vi) Resuspend cell pellet at a concentration of $3 \times 10^6$/ml in IMDM medium (100 μg/ml streptomycin), containing 10% FCS (heat inactivated) and 10% HS (heat inactivated). Note: If no FCS and HS available, use 20% to 50% autologous plasma.

(B) Cell Treatment Using Pure CR3/43 (Dako) Monoclonal Antibody:

After mononuclear cell separation has been achieved in A (vi), proceed with the following:

(i) Use a culture tray with six wells, add 2 mls of cell suspension [from A (vi) above] to each well of this multi-well culture tray.

(ii) Treat five wells each with 7.5 μl/ml of CR3/43-(pure monoclonal antibody, Dako) and leave one well untreated (negative control.

(iii) Incubate the culture tray in 5% $CO_2$ at 37 C.°.

(C) Purification of Cells:

Negative Selection of B cells using MACS microbeads (Miltenyi Biotec, here it is best to follow manufacturer instructions):

(i) Obtain mononuclear cells as in Section A above.

(ii) Pellet and resuspend cells in a final volume of 300 μl per $10^8$ total cells in HBSS (consisting of 2% FCS and 2 mM EDTA or 0.6% citrate).

(iii) Add 100 μl per $10^8$ total cells of pure monoclonal antibody to CD2 (IgG1, DAKO).

(iv) To the same cell suspension add 50 μl per $10^8$ per total cells of pure monoclonal antibody to CD33 (IgG1, DAKO).

(v) Leave the mixture to incubate for 10 minutes at room temperature.

(vi) Wash cells with HBSS (containing 2% FCS and 2 mM EDTA) and resuspend at a final concentration of 400 μl per $10^8$ total cells, with the same buffer.

(vii) Add 100 μl of rabbit anti-mouse IgG1 labelled microbeads per $10^8$ total cells (or follow manufacturer instructions).

(viii) Thoroughly mix cells and incubate at 6° C. to 12° C. (fridge) for 15 minutes.

(ix) Again wash cells with HBSS (containing 2% FCS and 2 mM EDTA) and resuspend at a final concentration of 500 μl per $10^8$ total cells, with the same buffer.

(x) Assemble MS+/RS+ column in the magnetic field of the MACS separator.

(xi) Wash column with 3 mls of HBSS (containing 2% FCS and 2 mM EDTA).

(xii) Pass cells through column and then wash with 4×500 µl with HBSS (containing 2% FCS and 2 mM EDTA).

(xiii) Elute and collect cells in a conical tube, then pellet and resuspended in IMDM as in Section A (vi).

D) FACSVantage Purified B Cells:

(i) Obtain mononuclear cells from peripheral blood samples of B-CLL patients, as described in Section A, above.

(ii) Stain these cells with a combination of CD19-PE and CD20-FITC conjugated monoclonal antibodies to identify the B cells.

(iii) On the basis of CD19/CD20 fluorescence, sort approximately $10^7$ cells using a Beckton Dickenson FACS Vantage and argon laser emitting at 488 nm.

(iv) Wash purified cells with Hanks balanced salt solution containing 50% FCS and then allow to recover overnight at 37° C. in a humidified incubator at 5% $CO_2$.

(v) Pellet and resuspend cells as described in Section A (vi) above and then treat with CR3/43 as described in Section B above.

Preparing Stem Cells in Whole Blood Cells

Treatment of cells with pure CR3/43 (Dako) monoclonal antibody in whole blood:

(i) Select patients with WBC counts of 30–200×$10^9$/L (ranging from 73–95% B lymphocytes).

(ii) Collect blood by venipuncture into citrate, EDTA- or preservative free heparin containing tubes.

(iii) Add CR3/43 Antibody directly to whole blood, at a final concentration of 0.08–0.16 µg/$10^6$ cells (e.g. if WBC count was 50×$10^9$/L then 50 µl of CR3/43 monoclonal antibody, mouse IgG concentration of 159 µg/ml, should be added per ml of blood).

(iv) Mix blood thoroughly and leave overnight at room temperature in an incubator.

(v) Analyse blood cells 0 hr, 2 hr, 6 hr and 24 hr after the addition of mAbs.

Note: Due to the homotypic aggregation of B cells and the formation of adherent cells in the bottom of the test tube, induced by mAb CR3/43, thoroughly mix and sample cells using wide-bore pipette tips or 21-G needle before analysis.

In order to obtain a uniform population of cells throughout the analysis, divide blood sample into separate aliquots prior CR3/43 treatment.

Preparation for Analysis of Stem Cells Produced by Treating Cultured B Cells with CR3/43 Monoclonal Antibody.

Stem cells produced using the methods of the invention can be assessed at a number of times points, for example every 2 hr, 7 hr, 24 hr, daily, 7 days or longer periods (months, following weekly feeding of cells with long term culture medium). In order to analyse all cells in the well including adherent and non-adherent layer, together or separately, one well has to be sacrificed.

(i) Gently remove non-adherent layer using a wide bore pipette and disrupt cell clumps by repeated aspiration through 21-G needle to obtain single cell suspension.

(ii) Using a cell scraper scrape adherent layer and disrupt gently cell clumps to obtain single cell suspension by repeated aspiration through a 21-G needle.

(iii) Alternatively, trypsinize adherent layer by first rinsing with HBSS and then adding 2 ml of 0.25% trypsin per well and incubate at 37° C. for 10 minutes.

(iv) Gently disturb cell clumps by repeated pipetting.

(v) After 10 mins incubate with 20% of FCS to a final concentration to inactivate the trypsin.

(vi) Wash cells twice with IMDM and 2% FCS by centrifugation at 800 g for 10 mins.

(vii) Count cells and assess viability.

Analysis of Stem Cells:

The following methods can be used for the assessment of stem cells.

(A) Immunophenotype:

For Immunophenotypic analysis (using Flow Cytometry).

(i) For whole blood samples, immunostain (according to manufacturer instructions), lyse the erythrocytes and wash the cells after the incubation period and treat with mAb. Lysing and wash solutions from Becton Dickinson may typically be used.

(ii) Leukocytes (in whole blood, mononuclear fraction, MACS microbeads negatively selected B cells or sorted B-CLL) should be either doubly or singly labelled with mAbs conjugated directly to fluorescein isothiocyanate (FITC) or phycoerythrin (PE).

(iii) Perform double labelling using IMK+ kit (Becton Dickinson): consisting of the following monoclonal antibody pairs:

CD45-FITC and CD14-PE;
CD19-PE and CD3-FITC;
CD8-PE and CD4-FITC;
HLA-DR-PE and CD3-FITC; and
CD56, CD16-PE and CD3-FITC.

Also isotype match negative controls for $IgG_1$-FITC and $IgG_{2a}$-PE are included.

(iv) The following additional antibodies can also be used which are manufactured by Dako and Becton Dickinson:

PE-conjugated: anti-CD8, anti-CD33, anti-13, anti-CD34, anti-CD19, anti-CD2, anti-CD14, anti-CD33 and anti-CD5;

FITC-conjugated: anti-CD3, anti-CD7, anti-IgM, anti-CD22 anti-CD20, anti-CD10, anti-CD7, anti-CD16, anti-TCRαβ.

(v) The following can also be used.

Also affinity purified $IgG_3$ mAb specific for CD34 (Dako) can be used and is detect with FITC- or PE-labelled goat anti-mouse immunoglobulin F(ab)'$_2$ fragment as secondary antibody (DAKO).

Quantum Red (PE-Cy5)-conjugated anti-CD34 (Dako) was also used.

(vi) Analyse cells using FACScan or FACS Vantage (Becton Dickinson).

(vii) Analyse data using Proprietary Paint-a-Gate, Lysis II, Consort 30 and CellQuest software.

(B) Morphology:

For morphological analysis:

Light Microscopy (i) Resuspend cells thoroughly using wide-bore pipette tips or 21-G needle.

(ii) Examine under a Leitz microscope using Wright's or Giemsa stains.

(iii) Morphological analysis of B-CLL lymphocytes can be performed in blood films or cytocentrifuged preparations, respectively.

Confocal Microscopy (i) Obtain B cells as described above (B-CLL or healthy B cells obtained from buffy coat of healthy blood donors)

(ii) Treat B cells with CR3/43 monoclonal antibody as described above.

(iii) Add 2 ml of cell suspension to an organ culture dish (The bottom of this dish is engineered to have a cover-slip).

(iv) Add 15 μl of monoclonal antibody to CD19 FITC-conjugate and 15 μl of monoclonal antibody to CD34 PE/Cy 5-conjugate (Quantum Red).

(v) Use Propidium Iodide to assess viability and Hoechst to stain the nuclei.

(C) PCR Analysis of VDJ Gene Rearrangement

The VDJ region of the IgH gene was analyzed by PCR (Perkin elmer thermal cycler) using template DNA from B-CLL peripheral blood samples before and after (2 hr, 6 hr and 24 hr) antibody treatment. The β-actin gene was used as a control. For the VDJ region, $V_H1$, $V_H2$, $V_H3$, $V_H4$, $V_H5$ and $V_H6$ family-specific sense primers were used with J antisense primers (Deane and Norton, 1990). All primers were synthesized by the Molecular Biology Unit, Randall Institute, King's College, London.

(D) Southern Analysis of VDJ Gene Rearrangement (i) Digest the Genomic DNA from treated and untreated peripheral blood samples or purified B cells (from B-CLL patients), using BamHI/HindII—typically cells from a number of wells are required to give a sufficient amount of DNA to conduct the analysis.

(ii) The digests were resolved on 0.8% agarose gels and transferred to GeneScreeng® nylon membranes (Dupont) according to manufacturer's instructions (Southern, 1975).

(iii) The rearrangement of the IgH gene can be characterised by analysing the J region of the IgH locus, using $^{32}$P-labeled human $J_H$ DNA probe isolated from placental genomic DNA (Calbiochem, Oncogene Science).

(iv) Autoradiographs should be kept at −70° C. for several days prior to developing.

(E) Long Term Culture:

Cell cultures prepared as described above can be maintained for longer periods (long term culture) by weekly feeding using long term culture medium (IMDM, 10% FCS, 10% HS, 1% hydrocortisone $5\times10^{-7}$M stock solution).

(i) First, following 24 hr from the initiation of CR3/43 treatment dilute cells in each well by adding 2 mls of long term culture medium.

(ii) Feed wells weekly following removal of half of the growth medium.

(iii) Inspect wells using phase-contrast microscopy.

(F) Colony Forming Assays:

(i) After, 24 hr following initiation (or longer incubation period with pure monoclonal antibody CR3/43) of treatment, obtain 300 μl in culture medium of the non-adherent cells as described above.

(ii) Add to the cell suspension in the culture medium above, 3 mls of methocult GFH4434 (StemCell Technologies, consisting of methylcellulose in Iscove's MDM, FCS, BSA, L-glutamine, rh stem cell factor, rh GM-CSF, rh IL-3 and rh erythropoietin).

(iii) Take 1.1 ml of cell mixture and plate in triplicate.

(iv) Incubate the plates at 37° C. in a humidified petri dish with 5% $CO_2$ and 5% O2 for 14 days.

(v) Inspect the wells before and after treatment with CR3/43 monoclonal antibody using phase-contrast microscopy.

B. Results

CD19 and CD3 Panel

Treatment of blood samples with monoclonal antibody to the homologous region of the β-chain of the HLA-DR antigen always decreased the relative number of $CD19^+$ cells. This marker is a pan B-cell antigen (see Tables). This antigen is present on all human B lymphocytes at all stages of maturation but is lost on terminally differentiated plasma cells. Hence, this is an indication that B cells were retrodifferentiating into undifferentiated cells.

The same treatment caused the relative number of $CD3^+$ cells to increase dramatically especially in blood of patients with B-CLL, which was always accompanied by an increase in the relative number in $CD3^-CD19^-$ cells. CD3 is present on all mature T-lymphocytes and on 65%–85% of thymocytes. This marker is always found in association with α-/β- or gamma/delta T-cell receptors (TCR) and together these complexes are important in transducing signals to the cell interior. Hence, this is an indication that B cells were retrodifferentiating into undifferentiated cells and then being committed to new differentiated cells, namely T cells.

A novel clone of cells appeared in treated blood of B-CLL patients co-expressing the CD19 and CD3 markers—i.e. $CD19^+$ and $CD3^+$ cells (see Chart 1, patient 2, 3 & 4 at 2 hr, 6 hr & 24 hr of starting treatment). Other patients with different conditions showed an increase in the relative number of these clones of cells. These cells were exceptionally large and heavily granulated and extremely high levels of CD19 were expressed on their cell membrane. The CD3 marker seems to be expressed on these cells at similar levels to those expressed on normal mature lymphocytes.

In Table 2, patient numbers 2, 3 and 4 are actually numbers representing the same patient and their delineation was merely to show the effect of treatment on blood with time (See Table 1 for experimental and clinical condition of this patient).

The $CD19^+CD3^+$ clones in treated samples seem to decrease with time, reaching original levels to those determined in untreated sample at 2 hrs, 6 hrs and 24 hrs.

Another type of cell of the same size and granularity was detected in treated samples and these cells had high levels of CD19 expressed on their surface but were negative for the CD3 marker and rich in FC receptors. However, the relative number of these cells appeared to decrease in time. Of interest, at 24 hours treatment of blood sample (2, 3 and 4) there was a decrease in the relative number of $CD19^-CD3^-$ cells in a group of cells that were initially observed to increase after 2 and 6 hrs treatment of blood samples. However, Coulter counts of WBC populations were reduced on treatment of blood with monoclonal antibody to the homologous region of the β-chain of the HLA-DR antigen. This finding suggests that this type of treatment gives rise to atypical cells that cannot be detected by Coulter (Table 1) but can be accounted for when measured by flow cytometry which counts cells on the basis of surface markers, size and granularity. Furthermore, these atypical cells were accounted for by analysing morphology using Wright's stain under a microscope. Flow cytometric charts of these phenomena are represented in Charts (1, 2, 3 & 4) and the immunophenotypic changes obtained on treatment of blood samples seems to suggest that $CD19^+$ and $CD3^+$ lymphocytes are an interconnected group of cells but remain distinct on the basis of CD19 and CD3 relative expression compared to stem cells.

In Table 2, patient numbers 5 and 6 represent the same patient but analysis of treated and untreated blood samples were monitored with time and at the same time (see Table 1).

Patients' blood with no B-cell malignancy showed similar trends of immunophenotypic changes when compared to blood of B-CLL patients but the changes were not to the same extent. However, the relative and absolute number of B-lymphocytes and MHC class II positive cells in the blood of these patients are extremely low compared to those found in the blood of B-CLL patients.

Two brothers both with X-linked infantile hypogammaglobulinemia who were B cell deficient showed different immunophenotypic changes in the relative number of CD3+ cells on treatment of their blood. The younger brother who was 2 months old and not ill, on treatment of his blood, showed a slight increase in the relative number of CD3+ cells which was accompanied by a decrease in the relative number of CD3−CD19− cells. On the other hand, the other brother who was 2 years old and was extremely sick and with a relatively high number of activated T cells expressing the DR antigens showed a decrease in the number of CD3+ cells on treatment of his blood. No other markers were used to measure other immunophentypic changes that might have occurred because the blood samples obtained from these two patients were extremely small (Table 2, ID-43/BD and 04/BD).

Patient 91 in Table 2 shows a decrease in the relative number of CD3+ cells following treatment of blood which was accompanied by an increase in the relative number of CD3−CD19− cells. However, on analysis of other surface markers such as CD4 and CD8 (see Table 3) the patient was observed to have a high relative number of CD4+CD8+ cells in his blood and this was noted prior to treatment of blood samples with monoclonal antibody to the β-chain of the DR antigen and these double positive cells decreased appreciably following treatment of blood. Furthermore, when further markers were analyzed the relative number of CD3+ cells were seen to have elevated (See Table 4).

An enriched preparation of B-lymphocytes obtained from healthy blood donors when treated with monoclonal antibody to the β-chain of DR antigens showed a dramatic increase in the relative number of CD3+ cells which were always accompanied by a decrease in the relative number of CD19+ cells and by an increase in the relative number of CD19−CD3− cells. Further analysis using markers such as CD4 and CD8 show a concomitant increase in the relative number of these markers. However, an enriched preparation of T lymphocytes of the same blood donors when treated with the same monoclonal antibody did not show the same changes.

CD4 and CD8 Panel

The CD4 antigen is the receptor for the human immunodificiency virus. The CD4 molecule binds MHC class II antigen in the B2 domain, a region which is similar to the CD8 binding sites on class I antigens. Binding of CD4 to class II antigen enhances T cell responsiveness to antigens and so does the binding of CD8 to class I antigens. The CD8 antigens are present on the human supressor/cytotoxic T-lymphocytes subset as well as on a subset of natural killer (NK) lymphocytes and a majority of normal thymocytes. The CD4 and CD8 antigens are coexpressed on thymocytes and these cells lose either markers as they mature into T-lymphocytes.

On analysis of the CD4 and CD8 markers—see below— and from a majority of blood samples presented in Table 2, a pattern of staining emerges which supports the presence of a retrodifferentiation process of B-lymphocytes into undifferentiated cells and the subsequent differentiation into T-lymphocytes.

CD4+CD8+ cells, which are double positive cells, always appeared following treatment of blood samples with monoclonal antibody to the homologous region of the β-chain and these types of cells were markedly increased in the blood of treated samples of patients with B-CLL and which were absent altogether in untreated samples (See Table 3 and Charts 1, 2, 3 & 4). In the same specimens the relative number of single positive cells such as CD8+ and CD4+ cells was also noted to increase simultaneously. Furthermore, a decrease in the relative number of CD4−CD8− cells which, at least in the case of B-CLL correspond to B cells was noted to fall dramatically in treated samples when compared to untreated specimens which remained at the same level when measured with time. However, measurement of the relative number of CD4+CD8+ cells with time in treated samples showed that there was a concomitant increase in the number of single positive cells with a decrease in the relative number of double positive cells. This type of immunophenotypic change is characteristic of thymic development of progenitor cells of the T-lymphocyte lineage in the thymus (Patient number 2,3 and 4). The CD4 antigen is present on the helper/inducer T-lymphocyte subsets (CD4+CD3+) and a majority of normal thymocytes. However, this antigen is present in low density on the cell surface of monocytes and in the cytoplasm of monocytes and macrophages (CD3−CD4+).

The relative number of CD4+ low cells was affected differently in different blood samples following treatment. The relative number of this type of cells seems unaffected in blood samples of patients with B-CLL following treatment when compared to untreated samples. Such low levels of CD4 expression is found on monocytes and very early thymocytes.

Patient HIV+25 on treatment showed a substantial increase in the number of double positive cells expressing CD4 and CD8 simultaneously. On the other hand, patient 91 on treatment showed a decrease in this subtype of cells and the observation of such phenomenon is time dependent. The relative number of CD8+ cells was observed to increase in untreated blood samples of patients with B-CLL when measured with time whereas the relative number of CD4+ and CD4+ low cells was observed to decrease at the same times (Table 3 patient 2, 3 and 4).

DR and CD3 Panel

The DR markers are present on monocytes, dendritic cells, B-cells and activated T-lymphocytes.

Treated and untreated samples analysed with this panel showed similar immunophenotypic changes to those obtained when blood samples were analysed with the CD19 and CD3 markers (see Table 2) and these antigens as mentioned earlier are pan B and T-cell markers respectively.

Treatment of blood with monoclonal antibodies seems to affect the relative number of DR+ B-lymphocytes so that the level of DR+ cells decrease. In contrast, the relative number of CD3+ (T-cells) cells increase significantly (see Table 4 and Chart). Furthermore, the relative number of activated T cells increased in the majority of treated blood samples of patients with B-CLL and these types of cells were affected variably in treated samples of patients with other conditions. Furthermore, the relative number of DR high positive cells appeared in significant numbers in treated samples of patients with B-CLL and a 6 day old baby with increased DR+CD34+ blasts in his blood. However, it should be noted that the blasts which were present in this patients blood were negative for T and B-cell markers before and after treatment but became more positive for myeloid lineage antigens following treatment. The relative number of CD3−DR− cells increased in the majority of treated blood samples and was proportional to increases in the relative number of CD3+ cells (T-cells) and was inversely proportional to decreases in the relative number of DR+ cells (B-cells).

CD56&16 and CD3 Panel

The CD56&CD16 markers are found on a heterogeneous group of cells, a subset of lymphocytes known generally as large granular lymphocytes and natural killer (NK) lymphocytes. The CD16 antigen is expressed on virtually all resting NK lymphocytes and is weakly expressed on some $CD3^+$ T lymphocytes from certain individuals. This antigen is found on granulocytes in lower amount and is associated with lymphocytes containing large azurophilic granules. The CD16 antigen is the lgG FC receptor III.

A variable number of $CD16^+$ lymphocytes coexpress either the CD57 antigen or low-density CD8 antigen or both. In most individuals, there is virtually no overlap with other T-lymphocyte antigens such as the CD5, CD4, or CD3 antigens. The CD56 antigen is present on essentially all resting and activated $CD16^+$ NK lymphocytes and these subsets of cells carry out non-major histocompatibility complex restricted cytotoxicity.

Immunophenotyping of treated and untreated blood samples of B-CLL and some other patients with other conditions showed an increase in the relative number of cells coexpressing the CD56&CD16 antigens which were heavily granulated and of medium size (see Table 5 and Charts 1, 2, 3 & 4). These observations were also accompanied by a marked increase in the relative number of cells expressing the CD3 antigen only (without the expression of CD56 and CD16 markers) and cells coexpressing the CD56&CD16 and CD3 markers together.

In Table 5, patient numbers 2, 3, and 4 represent the same blood sample but being analysed at 2 hours, 6 hours and 24 hours respectively (before and after treatment). This sample shows that treatment of blood with monoclonal antibody to the homologous region of the β-chain of DR antigen seems to cause spontaneous production of $CD56^+$ and $CD16^+$ cells, $CD3^+$ cells and $CD56^+$ and $CD16^+$ $CD3^+$ cells and these observations were always accompanied by the disappearance of B-cell markers (CD19, DR, CD56, $CD16^-CD3^-$).

Onward analysis of this blood sample before and after treatment showed the levels of $CD56^+$ and $CD16^+$ cells to decrease with time and the level of $CD3^+$ cells to increase with time.

Blood samples of patient 7 with B-CLL, did not show any changes in the number of cells expressing the CD56, CD16 and CD3 antigens when compared to immunophenotypic changes observed in treated and untreated samples and this is because the amount of monoclonal antibody added was extremely low relative to the number of B lymphocytes. However, treatment of this patient's blood sample on a separate occasion with an appropriate amount of monoclonal antibody showed significant increases in the relative number of $CD3^+$, $CD56^+$ & $CD16^+$ and $CD56^+$ and $CD16^+$ $CD3^+$ cells.

Blood samples of other patients with other conditions showed variable changes in the level of these cells and this seems to be dependent on the number of B-lymphocytes present in blood before treatment, duration of treatment and probably the clinical condition of patients.

CD45 and CD14 Panel

The CD45 antigen is present on all human leukocytes, including lymphocytes, monocytes, polymorphonuclear cells, eosinophils, and basophils in peripheral blood, thymus, spleen, and tonsil, and leukocyte progenitors in bone marrow.

The CD14 is present on 70% to 93% of normal peripheral blood monocytes, 77% to 90% of pleural or peritoneal fluid phagocytes. This antigen is weakly expressed on granulocytes and does not exist on unstimulated lymphocytes, mitogen-activated T lymphocytes, erythrocytes, or platelets.

The CD45 antigen represents a family of protein tyrosine phosphatases and this molecule interacts with external stimuli (antigens) and effects signal transduction via the Scr-family members leading to the regulation of cell growth and differentiation.

Figure 5:
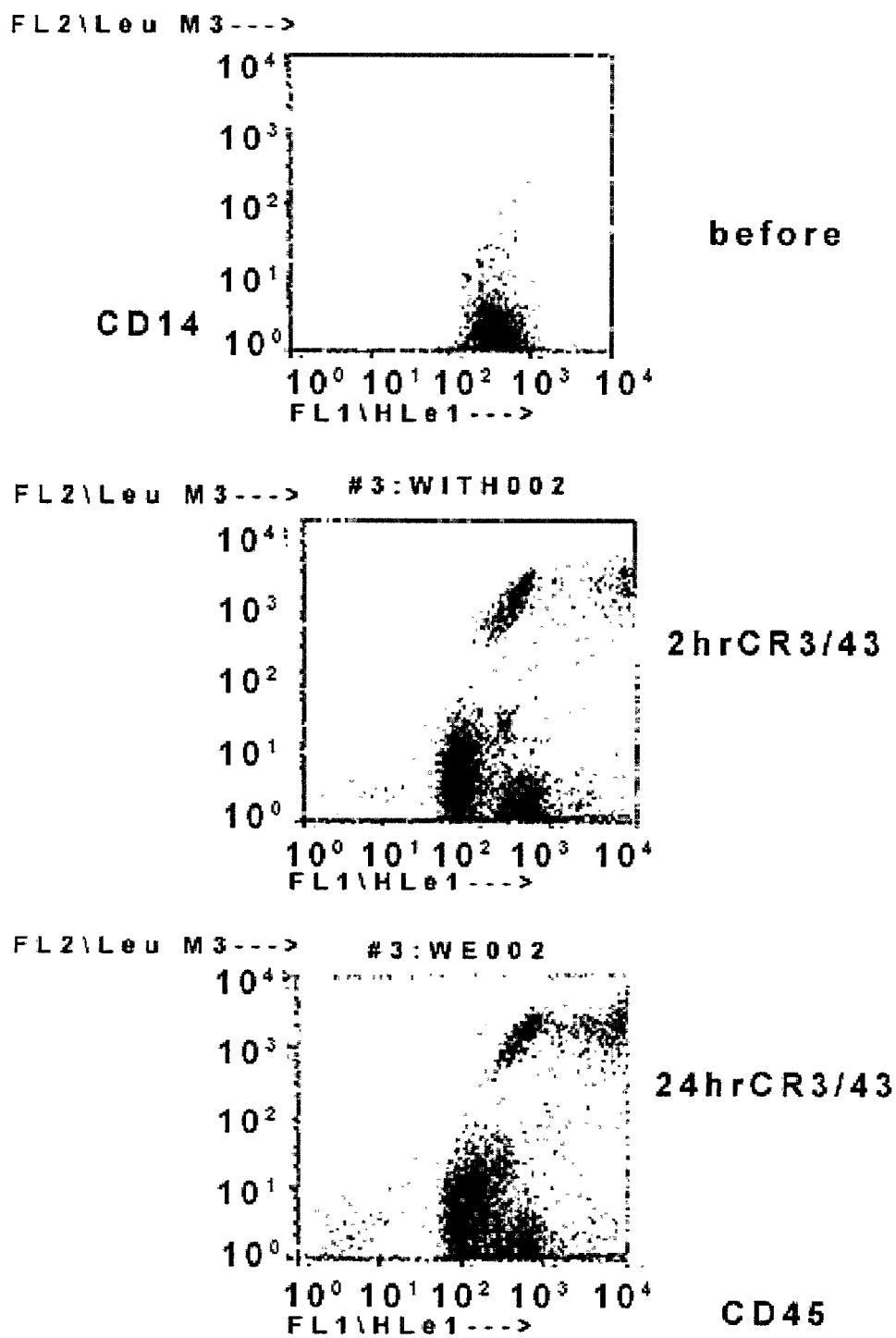
FIG. 5 is a scatter graph showing flow cytometry results.

Engagement of the β-chain of the DR antigens in treated blood samples especially those obtained from patients with B-CLL suggests that such a treatment affects the level of CD45 antigens on B-lymphocytes. The overall immunophenotypic changes that took place on stimulation of the β-chain of the DR antigen seem to give rise to different types of cells that can be segregated on the basis of the level of CD45 and CD14 expression as well as morphology as determined by forward scatter and side scatter (size and granularity respectively) and these results are presented in Table 6 and Charts (1, 2, 3 & 4). See also FIG. 5 which demonstrates the appearance of $CD45^-CD14^-$ cells after treatment with the CR3/43 antibody. These cells are not haempoietic cells.

On treatment the relative number of CD45 low cells (when compared to untreated samples) increased significantly and so did the relative number of cells co-expressing the CD45 and CD14 antigens. This type of immunophenotypic changes coincided with a decrease in the relative number of CD45 high cells (compared to untreated samples). However, this latter population of cells can be further divided on the basis of morphology and the degree of CD45 expression. One type was extremely large and had extremely high levels of CD45 antigen when compared to the rest of cells present in the charts (see charts 1, 2, 3 and 4). On analysis of this panel following treatment with time (see Table 6 patient 2, 3 and 4 and chart 1) the relative number of $CD45^+$ cells initially fell drastically with time to give rise to CD45 low cells. However, analysis of blood 24 hours later showed the opposite situation.

Samples 5 and 7 reveal opposite immunophenotypic changes to those obtained with other samples obtained from other B-CLL patients and this is because the samples were analysed at a much earlier incubation time with the monoclonal antibody. In fact the sequential analysis of blood samples after treatment seems to suggest that the immunophenotypic changes undertaken by B lymphocytes is time dependent because it represents a stage of development and the immunophenotypic changes measured at time X is not going to be the same at time X plus (its not fixed once induced). However, these types of changes must be occurring in a more stringent manner in the body otherwise immunopathology would ensue. The effect of treatment of blood samples from other patients with no B-cell malignancy show variable changes in immunophenotypes of cells and this because B-lymphocytes are present in lower amount. However, treatment of enriched fractions of B-lymphocytes obtained from healthy blood donors show similar immunophenotypic changes to those obtained with B-CLL with high B lymphocyte counts.

CD8 and CD3 Panel

The CD8 antigenic determinant interacts with class I MHC molecules, resulting in increased adhesion between the CD8+ T lymphocytes and the target cells. This type of interaction enhances the activation of resting lymphocytes. The CD8 antigen is coupled to a protein tyrosine kinase (p56ick) and in turn the CD8/p56ick complex may play a role in T-lymphocyte activation.

Treatment of blood samples obtained from patients with B-CLL with monoclonal antibody to the B chain causes a significant increase in the relative number of CD3CD8 and CD3 (highly likely to be CD4CD3) positive cells thus indicating more clearly that double positive cells generated initially are undergoing development into mature T-lymphocytes. This is a process that can be measured directly by CD19 and by DR and indirectly by CD8$^-$CD3$^-$ antigens. Serial assessment of treated blood samples of the same patient with time seems to agree with a process which is identical to thymocyte development (Table 7, patient 2, 3 and 4 and Chart 1).

The relative number of CD8$^+$ cells increased with time in treated and untreated samples but to a higher extent in untreated samples. On the other hand, the relative number of CD8$^+$CD3$^+$ cells decreased with time in untreated samples. However, the relative number of CD3$^+$ cells increased in treated blood samples when measured with time and these types of cells highly correspond to CD4$^+$CD3$^+$ single positive cells; a maturer form of thymocytes. In addition, since these samples were also immunophenotyped with other panels (mentioned above in Tables 3, 4, 5 and 6) the overall changes extremely incriminate B cells in the generation of T lymphocyte progenitors and progenies.

Blood samples from a patient with B-CLL (number 2, 3 and 4 Tables 1, 2, 3, 4, 5, 6, 7) in separate aliquots were treated with nothing, PE conjugated monoclonal antibody to the homologous region of the β-chain of DR antigen and unconjugated form of the same monoclonal antibody. On comparison of PE conjugated treatment clearly indicates no change in the relative number of CD3 positive cells and associated markers such as CD4 which have been observed in significant levels when the same blood sample was treated with unconjugated form of the antibody. However, an increase in the number of CD45 positive cells with no DR antigen being expressed on their surface was noted when measured with time (see Table 8). A finding that was similar to that noted in untreated samples when immunophenotyped with time (Table 6). Furthermore, the relative number of cells expressing CD45 low decreased in time, a phenomenon which was also noted in the untreated samples (when measured with time) of the same patient (see chart 1A).

C. Comparison of the Effect of Other Monoclonal Antibodies with Different Specificity on T-Lymphophoiesis CD19 and CD3 Panel Treatment of blood samples with monoclonal antibody to the homologous region of the α-chain of the DR antigen and the homologous region of MHC Class I antigens decreased the number of CD3$^+$ cells and increased the number of CD19$^+$ cells. Treatment of the same blood with monoclonal antibody to the homologous region of the β-chain of the DR antigen decreased the number of CD19$^+$ cells and increased the number of CD3$^+$ cells. Treatment with the latter monoclonal antibody with cyclophosphoamide revealed the same effect (Table 14 patient 5/6 with B-CLL at 2 hr treatment).

Onward analysis of CD19$^+$ and CD3$^+$ cells in the same samples revealed further increases in the relative number of CD3$^+$ cells only in blood treated with monoclonal antibody to the homologous region of the β-chain of DR antigen (Table 14 patient 5/6 at 24 hours following treatment). However, onward analysis (24 hours later patient 5/6 Table 14) of blood samples treated with cyclophosphamide plus monoclonal antibody to the β-chain of DR antigen show reversal in the relative number of CD19$^+$ and CD3$^+$ cells when compared to that observed at 2 hour incubation time under exactly the same condition.

In general, treatment of blood samples of the same patient with monoclonal antibody to the homologous region of the α chain of the DR antigen or monoclonal antibody to the homologous of the α-chain of the class I antigen shows an increase in the relative number of CD19$^+$ cells (pan B marker) when compared to untreated sample. The relative number of CD19$^-$CD3$^-$ cells decreased slightly in blood samples treated with monoclonal antibody to the α-chain of DR antigen or treated with monoclonal antibody to class I antigens (see Table 14 & Charts 2, 3 & 4). Treatment of blood samples of patient 09 with monoclonal antibody to class I antigens increased the relative number of CD3$^+$ cells and decreased slightly the relative number of CD19$^+$ and CD19$^-$CD3$^-$ cells. However, treatment of an enriched preparation of B-lymphocytes obtained from healthy blood donors with monoclonal antibody to the β-chain or α-chain of DR antigen showed similar immunophenotypic changes to those obtained with patient with B-CLL.

Treatment of HIV$^+$ and IgA deficient patients with monoclonal antibody to the β-chain of the DR antigen increased the relative number of CD3$^+$ cells and decreased the relative number of CD19$^+$ cells. However, treatment of the same blood sample with monoclonal antibody to the homologous region of class I antigen did not produce the same effect. Treatment of blood samples obtained from patients (34/BD and 04/BD) with B-cell deficiency showed variable immunophenotypic changes when treated with monoclonal antibodies to the β-chain of the DR antigen, class I antigens and CD4 antigen.

CD4 and CD8 Panel

Blood samples analysed using the CD19 and CD3 panel (Table 14) were also immunophenotyped with the CD4 and CD8 panel (Table 15). Both panels seem to agree and confirm each other. Incubation for 2 hours of blood samples of patients with B-CLL (Table 15, patients 5/6 and 10, Charts 2, 3 & 4) with monoclonal antibody to the homologous region of the β-chain of the DR antigen or with this monoclonal antibody plus cyclophosphoamide increased the relative number of CD8$^+$ and CD4$^+$ cells and cells coexpressing both markers. On the other hand, treatment of the same samples with monoclonal antibodies to the homologous region of the α-chain of the DR antigen or the homologous region of the α-chain of class I antigen did not produce the same effects.

Comparison of immunophenotypic trends obtained at 2 hours and 24 hours incubation periods with monoclonal antibody to the β-chain of the DR antigen plus cyclophosphoamide revealed reverse changes in the relative number of CD4 and CD8 positive cells (Table 15, patient 5/6 with B-CLL at 2 hours and 24 hours) and such changes were in accordance with those obtained when the same blood sample was analysed with the CD19 and CD3 panel (Table 14 the same patient). The later findings indicate that the subsequent differentiation is reversible as the undifferentiated cells can differentiate into T-lymphocytes or B-lymphocytes.

DR and CD3 Panel

The immunophenotypic changes obtained with DR and CD3 (Table 16) panel confirm the findings obtained with CD19 and CD3 panel and CD4 and CD8 panel (Tables 14 & 15 & Charts 2, 3 & 4) which followed treatment of the same blood samples with monoclonal antibodies to the homologous region of the beta- or alpha- side of the DR antigen or monoclonal antibody to class I antigens or monoclonal antibody to the β-chain of the DR antigen plus cyclophosphoamide at 2 hour analysis.

From the results, it would appear that the monoclonal antibody to the homologous region of the β-chain of the DR antigen is extremely capable of driving the production of CD3 positive cells from DR+ cells.

Furthermore, treatments such as those involving engagement of the α-chain of DR antigens or engagement of the β-side of the molecule in conjunction with cyclophosphoamide (prolonged incubation time) promoted increases in the relative number of CD19+ cells or DR+ cells.

CD56&16 and CD3 Panel

Treatment of blood samples, especially of those of patients with B-CLL with high B-lymphocyte counts with monoclonal antibody to the homologous region of the β-chain of the DR antigen increased the relative number of CD56&16 positive cells.

In these patients the relative number of CD3+ and CD56+ and CD16+CD3+ cells also increased following treatment of blood samples with monoclonal antibody to the β-chain, confirming earlier observations noted with the same treatment when the same blood samples were analysed with CD3 and CD19 and DR and CD3 panels.

CD45 and CD14 Panel

Blood samples treated with monoclonal antibodies to the β- or alpha-chains of the DR antigen or to the β-chain plus cyclophosphoamide or class I antigens were also analysed with the CD45 and CD14 panel (Table 18). The delineation of CD45 low, CD45 high and CD45 medium is arbitrary. Treatment of blood sample 5/6 (at 2 hours) with monoclonal antibodies to the β-chain of the DR antigen or with this monoclonal antibody plus cyclophosphoamide generated CD45+ low cells and increased the relative number of CD45+ medium cells. However, the former treatment increased the relative number of CD45+ high cells and the latter treatment decreased the relative number of CD45+ medium cells and these changes appeared to be time dependent.

Blood samples of patient 5/6 and 10 (B-CLL) on treatment with monoclonal antibody to class I antigens showed a decrease in the relative number of CD45+ medium cells and similar observations were noted in blood samples 09 and HIV+ following the same treatment when compared to untreated samples. Treatment of blood samples of HIV+ and IgA/D patients with monoclonal antibody to class I antigen increased the relative number of CD45+ low cells when compared to untreated samples or samples treated with monoclonal antibody to the β-chain of the DR antigen. However, blood samples of these patients showed a decrease in the relative number of CD45+ medium cells on treatment with monoclonal antibody to the homologous regions of the β-chain of the DR antigen. Medium CD45+ cells increased in blood samples of IgA/D patient following monoclonal antibody to class I antigen treatment. Cells that were extremely large, heavily granular and expressing intense levels of CD45 antigen were noted in treated blood samples with monoclonal antibody to the homologous region of the β-chain of DR antigen of MHC class II antigens (see Charts 1, 2, 3 & 4).

CD8 and CD28 Panel

The CD28 antigen is present on approximately 60% to 80% of peripheral blood T (CD3+) lymphocytes, 50% of CD8+ T lymphocytes and 5% of immature CD3-thymocytes. During thymocyte maturation, CD28 antigen expression increases from low density on most CD4+CD8+ immature thymocytes to a higher density on virtually all mature CD3+, CD4+ or CD8+ thymocytes. Cell activation further augments CD28 antigen density. Expression of the CD28 also divides the CD8+ lymphocytes into two functional groups. CD8+ CD28+ lymphocytes mediate alloantigen-specific cytotoxicity, that is major histocompatibility complex (MHC) class I-restricted. Suppression of cell proliferation is mediated by the CD8+CD28− subset. The CD28 antigen is a cell adhesion molecule and functions as a ligand for the B7/BB-1 antigen which is present on activated B lymphocytes.

Treatment of blood samples of patients (Table 19, patients 5/6 and 8) with B-CLL with monoclonal antibody to the homologous region of β-chain of the DR antigen increased the relative number of CD8+, CD28+ and CD8+CD28+ cells and all other types of treatments did not.

CD34 and CD2 Panel

The CD34 antigen is present on immature haematopoietic precursor cells and all haematopoietic colony-forming cells in bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)+ B- and T-lymphoid precursors in normal bone are CD34+, The CD34 antigen is present on early myeloid cells that express the CD33 antigen but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early haematopoietic progenitor cells and decreases as the cells mature. The antigen is absent on fully differentiated haematopoietic cells.

Uncommitted CD34+ progenitor cells are CD38−, DR− and lack lineage-specific antigens, such as CD71, CD33, CD10, and CD5, while CD34+ cells that are lineage-committed express the CD38 antigen in high density.

Most CD34+ cells reciprocally express either the CD45RO or CD45RA antigens. Approximately 60% of acute B-lymphoid leukaemia's and acute myeloid leukaemia express the CD34 antigen. The antigen is not expressed on chronic lymphoid leukaemia (B or T lineage) or lymphomas. The CD2 antigen is present on T lymphocytes and a subset of natural killer lymphocytes (NK).

The results are shown in Charts 2, 3 and 4.

Analysis of blood samples of a patient with B-CLL (Table 20, patient 5/6 at 2 hours) after treatment with monoclonal antibodies to the β-chain of the DR antigen or the α-chain of the same antigen revealed marked increases in the relative number of CD34+ and CD34+CD2+ cells after treatment with the former antibody. Since the same blood samples were immunophenotyped with the above mentioned panels (see Tables 14 to 19 ) for other markers the increase in the relative number of CD34+ and CD34+CD2+ cells observed here seems to coincide with increases in the relative number of CD4+CD8+, CD8+CD3+ and CD4+CD3+ single positive (SP) cells. Furthermore, these findings which seem exclusive to engagement of the β-chain of the HLA-DR antigen, are in direct support that the process is giving rise to T-lymphopoiesis via B lymphocyte regression.

On analysing the same treatment 24 hours later the CD34+ cells seemed to decrease in levels to give rise to further increase in the relative number of T lymphocytes. The process of retrodifferentiation that initially gave rise to T-lymphopoiesis can be reversed to give rise to B-lymphopoiesis. The former phenomenon was observed at 2 hours incubation time with monoclonal antibody to the β-chain of the HLA-DR antigen plus cylophosphoamide, whereas the latter process was noted at 24 hours incubation time with the same treatment in the same sample (Chart 2).

Treatment of blood samples of HIV+ patient (Table 20 patient HIV+) with monoclonal antibody to the β-chain of the HLA-DR antigen markedly increased the relative number of $CD34^+$ and $CD2^+CD34^+$ cells and so did treatment of the same blood sample with monoclonal antibody to the β-chain of the HLA-DR antigen and monoclonal antibody to the α-chain of the same antigen when added together. However, treatment of this blood sample with monoclonal antibody to the α-chain of the HLA-DR antigen did not affect the level of $CD34^+$ cells. Treatment of blood samples obtained from a 6-day old baby (BB/ST Table 20) who was investigated at that time for leukaemia and who had very high number of atypical cells (blasts) in his blood with monoclonal antibody to the β-chain of the HLA-DR antigen, or monoclonal antibody to the α-chain of the same antigen or both monoclonal antibodies added together resulted in the following immunophenotypic changes.

On analysis of untreated blood samples the relative number of $CD34^+$ and $DR^+$ cells were markedly increased and on treatment with monoclonal antibody to the β-chain the relative number of $CD34^+$ cells further increased but were noted to decrease on treatment with monoclonal antibody to the α-chain of the HLA-DR antigen or treatment with monoclonal antibodies to the α and β-chains of the molecule when added together. However, the latter treatment increased the relative number of $CD34^+CD2^+$ cells and the opposite occurred when the same blood sample was treated with monoclonal antibody to the β-chain of the HLA-DR antigen alone. On analysis of treated and untreated blood aliquots of the same patient 24 hours later the relative number of CD34+ decreased with all above mentioned treatments except it was maintained at a much higher level with monoclonal antibody to the β-chain of the HLA-DR antigen treatment. The latter treatment continued to decrease the relative number of $CD34^+CD2^+$ cells 24 hours later.

These results indicate that engagement of the HLA-DR antigen via the β-chain promotes the production of more $CD34^+$ cells from $CD2^+CD34^-$ pool or from more mature types of cells such as B-lymphocytes of patients with B-CLL and these results indicate that this type of treatment promotes retrodifferentiation. However, immunophenotyping of blood samples 24 hours later suggests that these types of cells seem to exist in another lineage altogether and in this case cells seem to exist or rather commit themselves to the myeloid lineage which was observed on analysis of treated blood sample with the CD7 and CD13&33 panel.

Morphology changes immunophenotypic characteristics of B-lymphocytes of B-CLL and enriched fractions of healthy individuals (using CD19 beads) on treatment with monoclonal antibodies to homologous regions of the β-chain of MHC class II antigens. These were accompanied by a change in the morphology of B-lymphocytes. B-lymphocytes were observed colonising glass slides in untreated blood smears were substituted by granulocytes, monocytes, large numbers of primitive looking cells and nucleated red blood cells. No mitotic figures or significant cell death were observed in treated or untreated blood smears. The results of Table 20 also demonstrate a further important finding in that according to the method of the present invention it is possible to prepare an undifferentiated cell by the retrodifferentiation of a more mature undifferentiated cell.

D. Microscope Pictures

In addition to the antigen testing as mentioned above, the method of the present invention was followed visually using a microscope.

Figure 6:
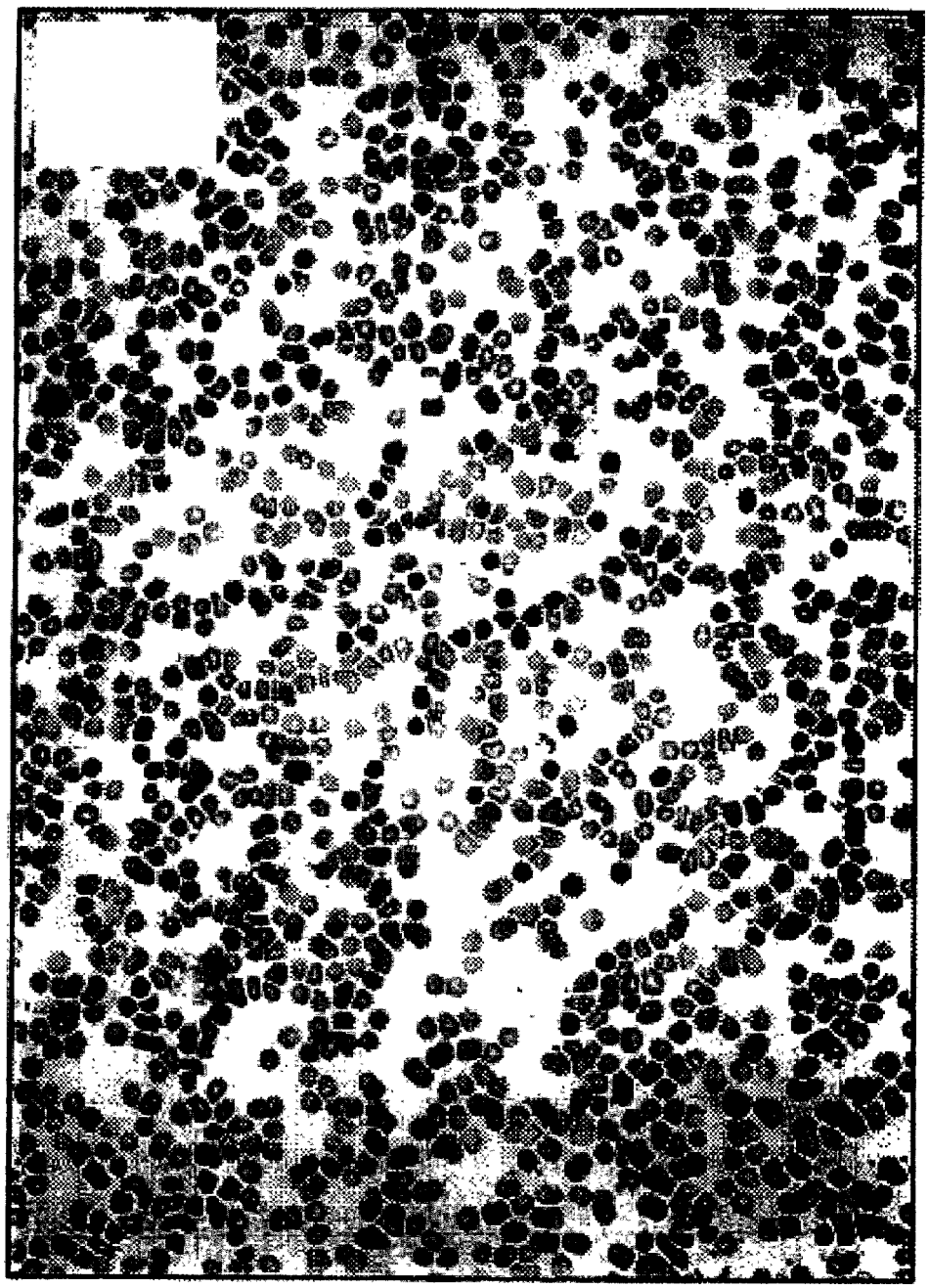
FIG. 6 is a microscope picture of cells before treatment according to the method of the present invention.
Figure 7:
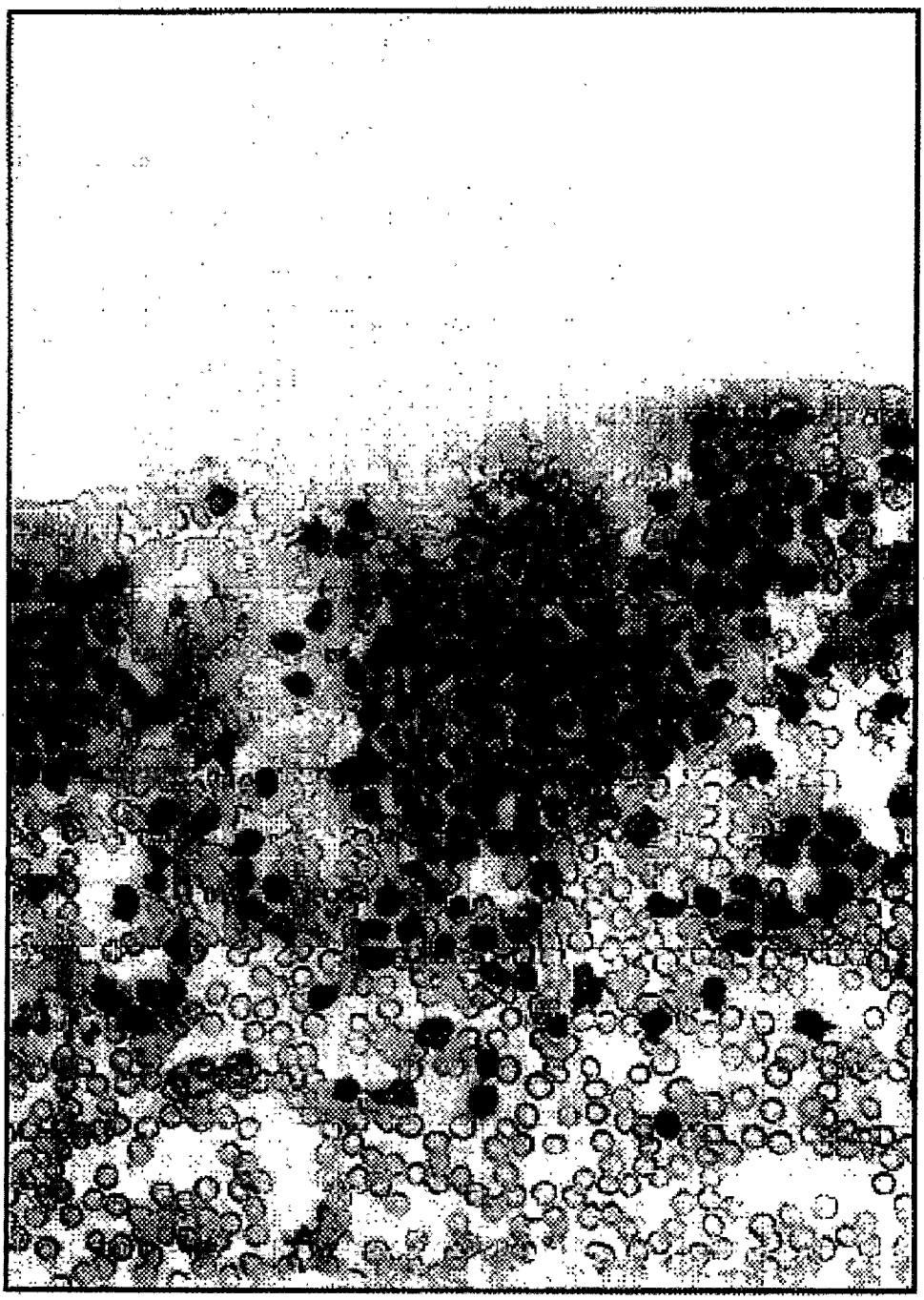
FIG. 7 is a microscope picture of cells prepared by the method of the present invention.
Figure 8:
FIG. 8 is a microscope picture of cells prepared by the method of the present invention but at a lower magnification.

In this regard, FIG. 6 is a microscope picture of differentiated B cells before the method of the present invention. FIG. 7 is a microscope picture of undifferentiated cells formed by the retrodifferentiation of the B cells in accordance with the present invention wherein the agent was a monoclonal antibody to the homologous regions of the β-chain of HLA-DR antigen. The undifferentiated cells are the dark stained clumps of cells. FIG. 8 is a microscope picture of the same undifferentiated cells but at a lower magnification.

FIGS. 6 to 8 therefore visually demonstrate the retrodifferentiation of B cells to undifferentiated stem cells by the method of the present invention.

Figure 9:
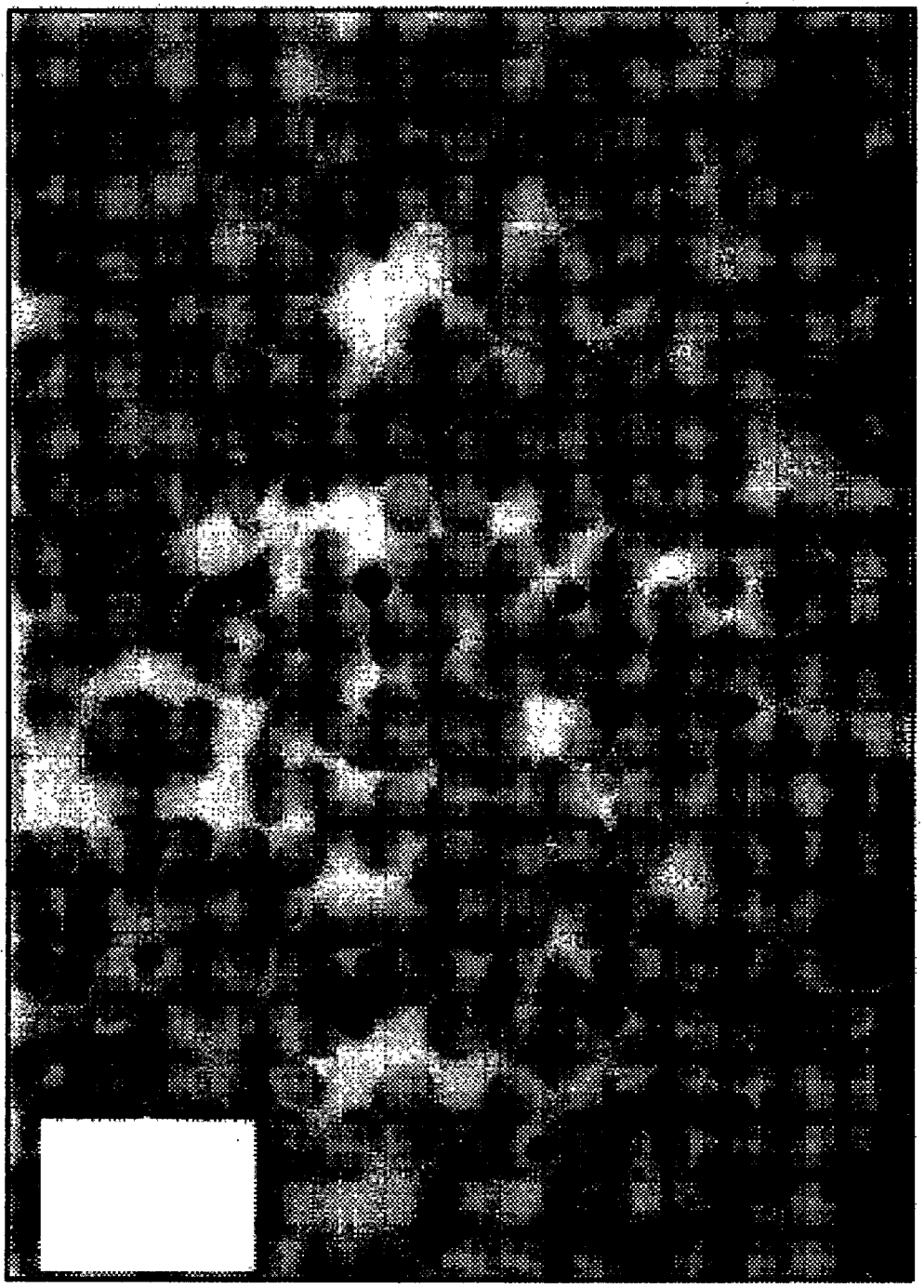
FIG. 9 is a microscope picture of cells before treatment according to the method of the present invention.
Figure 10:
FIG. 10 is a microscope picture of cells prepared by the method of the present invention.
Figure 11:
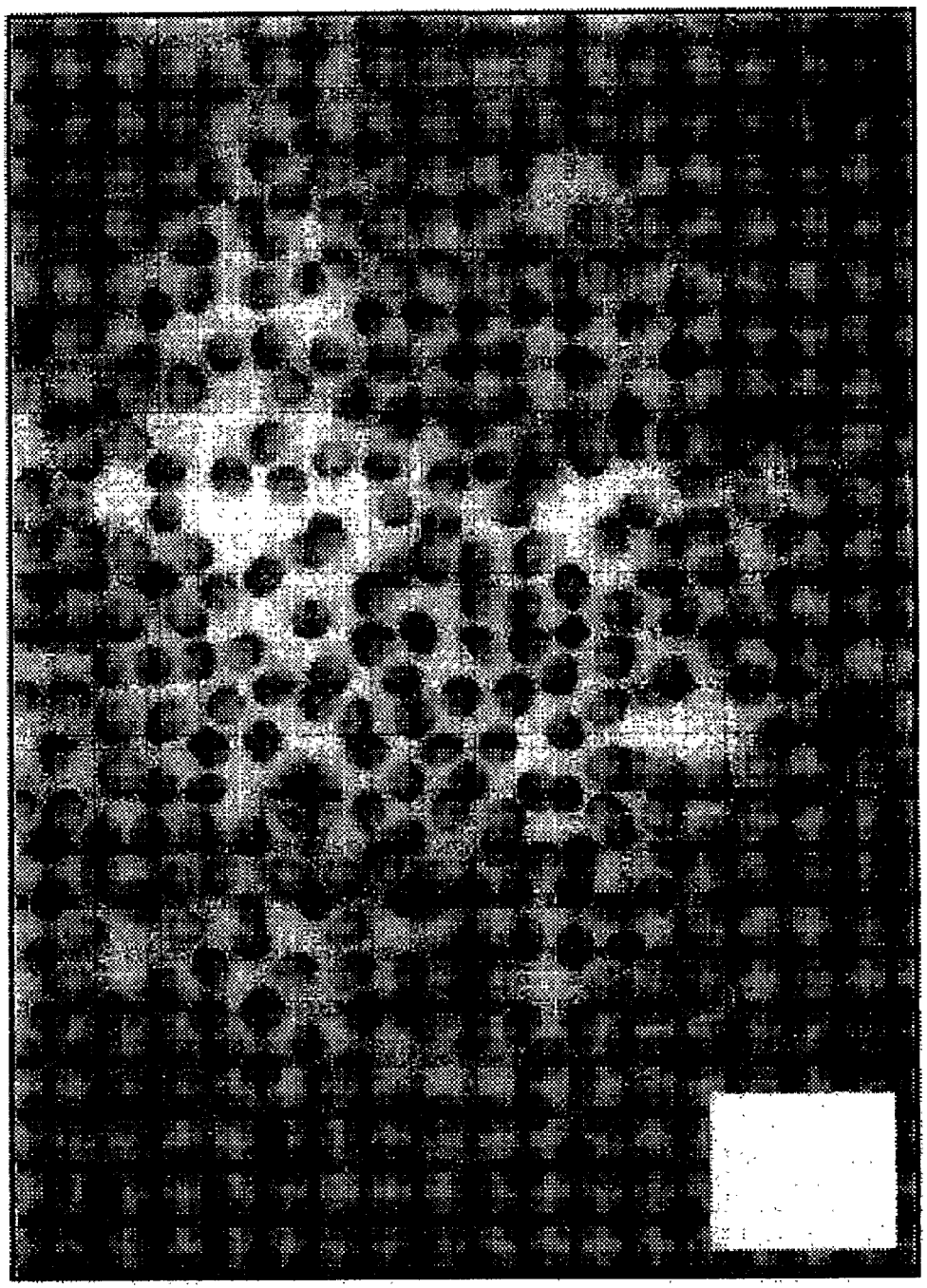
FIG. 11 is a microscope picture of cells prepared by the method of the present invention.

FIG. 9 is a microscope picture of differentiated B cells before the method of the present invention. FIG. 10 is a microscope picture of undifferentiated cells formed by the retrodifferentiation of the B cells in accordance with the present invention wherein the agent used was a monoclonal antibody to the homologous regions of the β-chain of HLA-DR antigen. Again, the undifferentiated cells are the dark stained clumps of cells. FIG. 11 is a microscope picture of the formation of differentiated granulocyte cells from the same undifferentiated cells of FIG. 10.

FIGS. 9 to 11 therefore visually demonstrate the retrodifferentiation of B cells to undifferentiated stem cells by the method of the present invention followed by commitment of the undifferentiated cells to new differentiated cells being of a different lineage as the original differentiated cells.

These microscopy experiments have also been performed with blood from BCLL patients, treated with the CR3/43 monoclonal antibody as described above. As discussed above, blood from BCLL cells is a useful aid in studying the retrodifferentiation process because the blood contains higher than normal numbers of B lymphocytes. The results are shown in detail in FIGS. 12 to 15.

Figure 12A:
FIG. 12 is a photomicrograph of a blood sample from a BCLL patient before treatment according to the method of the present invention. A and B are at different magnifications.
Figure 12B:
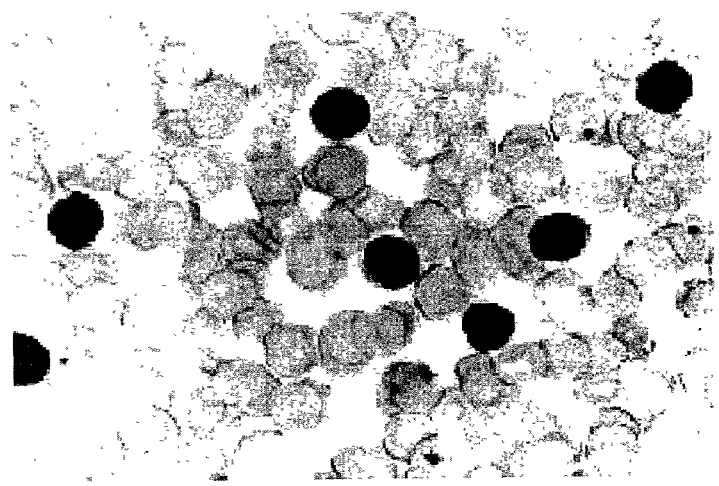

FIG. 12 shows at two different magnifications, an untreated blood sample from a BCLL patient. The untreated B lymphocytes (blue cells) show typical morphology, i.e. condensed chromatin structure and sparse cytoplasm. The remaining cells are erythrocytes (red blood cells).

Figure 13A:
FIG. 13 is a photomicrograph of a blood sample from a BCLL patient during, treatment according to the method of the present invention
Figure 13B:
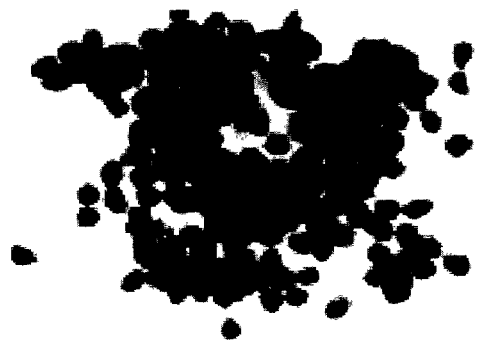
Figure 13C:

Treatment of blood samples with antibody CR3/43 leads initially to clustering of B lymphocytes into aggregates (FIG. 13).

Figure 14A:
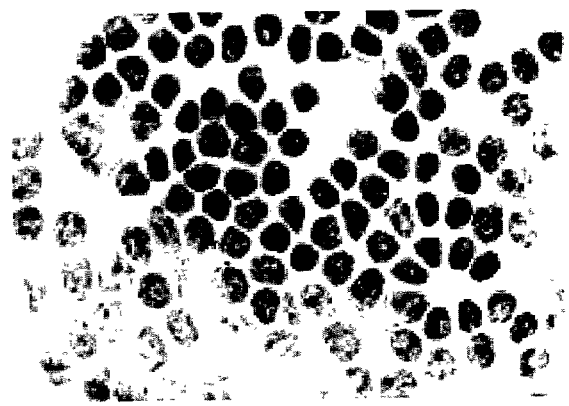
FIG. 14 is a photomicrograph of a blood sample from a BCLL patient during treatment according to the method of the present invention
Figure 14B:
Figure 14C:

The clustered B cells gradually lose their typical morphology, characterised by the formation of cobblestone-like-cell areas, decondensation of chromatin structure, appearance of prominent nucleoli, enlargement of cell volume and cytoplasmic basophilia typical of undifferentiated cells (FIG. 14). Relaxed (decondensed) chromatin structure is an important feature of undifferentiated cells as compared to differentiated cells. This is likely to be due to a need for more extensive access to transcriptional units to determine changes in gene expression required for commitment along a given cell lineage. By contrast, it is well known that more differentiated cell have a more condensed chromatin structure since only a small amount of chromatin needs to be transcriptionally active.

The appearance of undifferentiated cells is always accompanied by the appearance of cells (15A to 15J) with differentiated morphology. Importantly, these cells could not have arisen by proliferation, since (i) the incubation time was too short for one or more complete cell divisions to take place (ii) no mitotic figures are seen and (iii) the absolute number of leucocytes remained the same before and after treatment. Furthermore less differentiated progenitors were seen in association with their more differentiated progenies (see the myeloid precursor in FIG. 15J), indicating that these specialized cells arose by differentiation.

Micrographs FIGS. 15A to 15J show the types of differentiated cells seen following treatment of B-CLL lymphocytes with CR3/43 monoclonal antibodies: Platelets (Pl)—FIG. 15A, Neutrophils (Ne)—FIG. 15B, Eosinophils (Eso)—FIG. 15C, Megakaryocytes (Meg)—FIG. 15D, Basophils (Ba)—FIG. 15G, Lymphocytes (Ly)—FIG. 15H, Monocytes (Mo)—FIG. 15I and Myeloid progenitors (Mp)—FIG. 15J. Also seen were erythroid progenitors and macrophages (data not shown).

Thus, in summary, these microscopy results show changes in B cell morphology in samples from BCLL patients, who have high levels of mature B lymphocytes. The microscopy pictures show changes in the morphology of the B lymphocytes, which initially cluster, followed by the appearance of various cells with a graded range of morphologies from progenitor cells to differentiated cells (neutrophils, basophils, eosinophils, megakaryocytes, platelets, lymphocytes, macrophages, granulocytes, stab granulocytes and stromal-like cells).

Figure 15A:
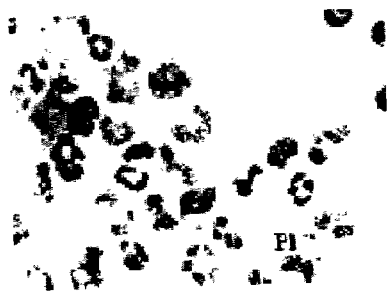
FIG. 15 is a photomicrograph of a blood sample from a BCLL patient after treatment according to the method of the present invention, showing cells prepared by the method of the invention.
Figure 15B:
Figure 15C:
Figure 15D:
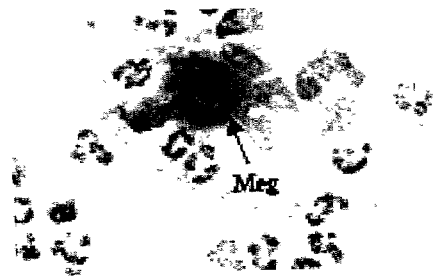
Figure 15E:
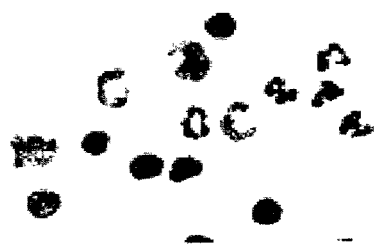
Figure 15F:
Figure 15G:
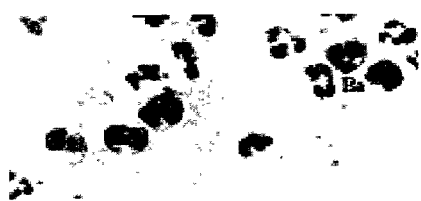
Figure 15H:
Figure 15I:
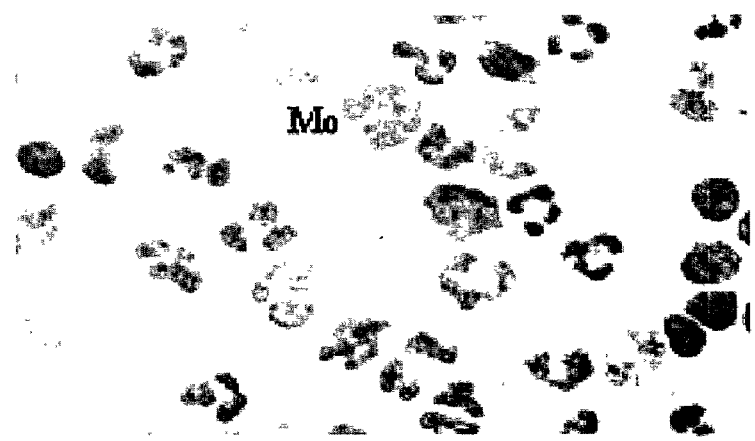
Figure 15J:
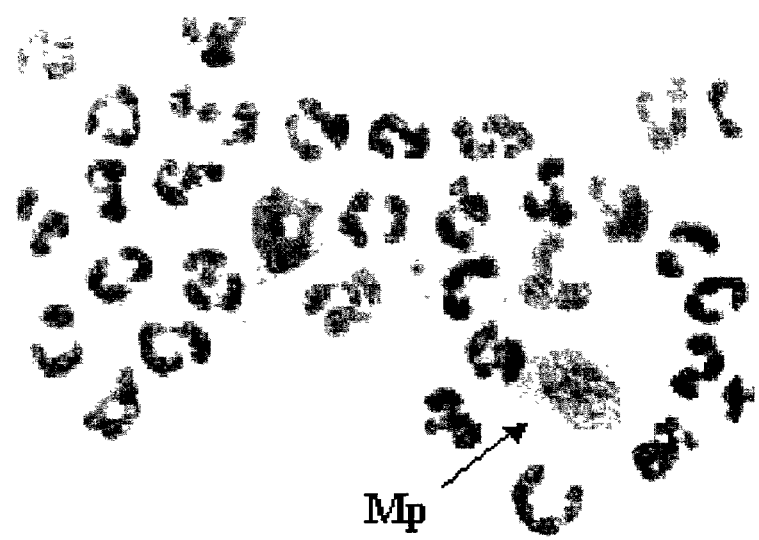

In addition, and very importantly, the presence of erythroid and myeloid progenitors is seen (FIG. 15J—and data not shown). The myeloid progenitor is clearly distinguishable morphologically from the other cells, being larger and with a distinct nuclear morphology as well as containing cytoplasmic granules.

The microscopy data therefore support morphologically what the flow cytometry data indicate in terms of cell surface markers. These data allow one to conclude that treatment of B lymphocytes with an antibody to MHC HLA-DR β chain results in a decrease in the numbers of B lymphocytes and an increase in the number of cells of other haemapoietic lineages including immature precursor cells.

The retrodifferentiation of T cells treated with an antibody to an MHC class II α-chain (monoclonal antibody TAL.1B5) to undifferentiated stem cells by the method of the present invention followed by commitment of the undifferentiated cells to new differentiated cells being of a different lineage as the original differentiated cells was also followed by microscopy (data not shown).

E. Analysis of VDJ Recombination Rearrangements in Retrodifferentiated Lymphocytes By way of background, the differentiated cells used in these experiments (B lymphocytes or cells with certain properties of T lymphocytes) have genes which have already undergone rearrangement to encode a mature Ig or a TCR, respectively. In the process or rearranging, intermediate portions of DNA that are not part of the final, expressed TCR or Ig gene, primarily DNA which is between the variable (V) region encoding segment and the constant (C) region-encoding segment of these receptors, are spliced out of the genome. These excised fragments are retained in the cell in the form of extrachromosomal DNA. For the cells to truly retrodifferentiate, the excised DNA would be reinserted into the genome, placing the cells in a state similar to that preceding their original differentiation. Because of this, a probe complementary to a sequence in the rearranged gene will be expected to hybridize to a larger DNA restriction fragment when the DNA has returned to its unrearranged or germ line state as compared to the rearranged DNA that characterizes the differentiated state.

1. Rearrangement of TCR Genes in Daudi Cells

Figure 16:
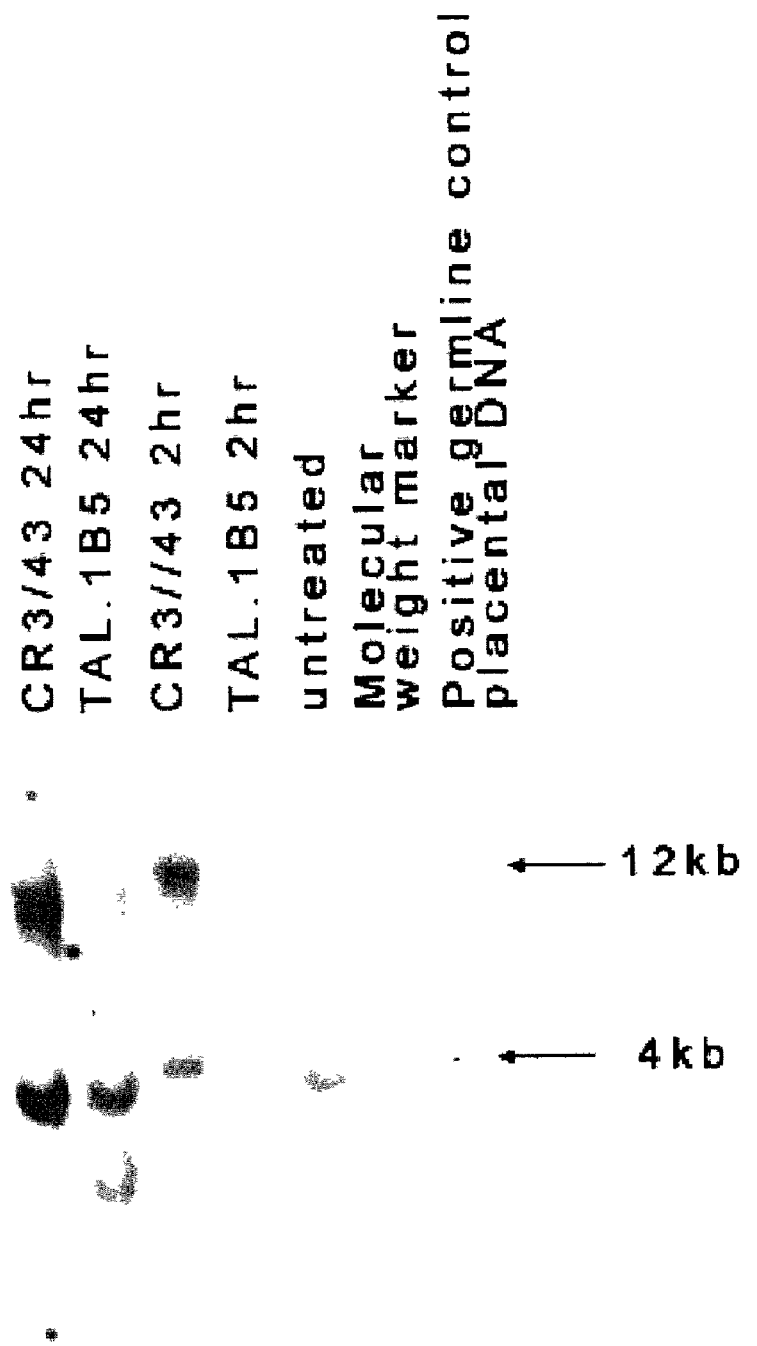
FIG. 16 is a photograph of a Southern blot.

In the experiment resulting in the Southern blot shown in FIG. 16, a well-known cell line, Daudi, a B-cell lymphoma with one rearranged TCR gene (and the other deleted), was used. Genomic DNA was prepared from Daudi cells and digested with EcoRI, subjected to gel electrophoresis and probed with a labeled TCR β-chain DNA probe. Daudi cells were used rather than B lymphocytes purified from human patients because these cells are clonally related and form a homogenous cell population with the same gene rearrangements that can be clearly viewed by Southern blotting of digested genomic DNA. In a normal blood sample, different cells have different rearrangements and so a Southern blot would appear as a smear.

A functional gene encoding the TCR β-chain is assembled in lymphocytes by a series of somatic rearrangements that occur during lymphocyte maturation to bring together a V segment, a D segment and a J segment. A very clear explanation of these rearrangement processes is given in Genes VI, Lewin, Oxford University Press, 1997 (pages 1994–1023)—a standard undergraduate textbook. Particular pages are cited below.

Firstly, a D segment is joined by a recombination process to one of several J segments in a D-J joining reaction. Then, one of the many possible V segments(<60) is joined to the resulting DJ segment (V-D joining) to form a complete TCR β-chain gene. The constant region gene is immediately downstream of the rearranged VDJ segment, although there may be intervening J segments which are spliced out during RNA processing to bring the constant gene exon into proximity with the rearranged VDJ gene segment (Lewin, p998).

In human cells, there are two different TCR β-chain constant region gene segments, denoted Cβ1 and Cβ2, present at two different loci, each of which is preceded by a cluster of six or seven joining region (Jβ) gene segments (Jβ1 and Jβ2) and one D segment (Dβ1 and Dβ2) (see FIG. 1, Toyonaga et al., 1985, Proc. Natl. Acad. Sci. USA 82: 8624–8628 and Lewin, p1017).

The recombination events which lead to the V, D and J-C segments being brought into proximity are catalysed by a multitude of proteins, including RAG-1 and RAG-2 which recognise nonamer and heptamer sequences present at the recombining ends of the V, D and J-C gene sequences. Depending on the orientation of these nonamer/heptamer sequences, recombination results either in an inversion or a deletion. Both types of events will result in a change in the restriction enzyme fragment pattern of the genomic DNA. Furthermore, a deletion event does not necessarily result in complete loss of the excised fragment. Rather, the ends of the excised fragment are rejoined to produce a circle of DNA which remains in the cell (Okazaki et al., 1987, Cell 49: 477–85; Davis et al., 1991, J. Exp. Med. 173: 743–6; Livak and Schatz, 1996, Mol. Cell Biol. 16: 609–18; Harriman et al. 1993, Annu Rev Immunol. 11:361–84). Each gene segment, of course, has two alleles since cells have a diploid chromosome complement.

In the normal germline state, the Cβ1 and Cβ2 genes are arranged as shown in FIG. 1, Toyonaga et al., 1985. A restriction digest of genomic DNA with EcoRI will generate two relevant bands detectable by the probe used in the experiment (the probe is a labelled DNA fragment derived from Cβ1 which also hybridises to Cβ2 due to a high degree of sequence homology): (i) a 12 kb band containing Cβ1 sequence; and (ii) a 4 kb band containing Cβ2 sequence. This germline configuration is seen in undifferentiated immature cells (lane A of FIG. 16) This germline configuration is also perfectly illustrated by lane 3 (2 hours with CR3/43 antibody) of FIG. 16, giving an identical pattern to that of lane A.

In the differentiated state, both alleles of Cβ1 and Cβ2 genes are rearranged such that there is no longer a 12 kb fragment at the Cβ1 locus or a 4 kb fragment at the Cβ2 locus. In fact, no hybridising fragment derived from the Cβ1 locus is present on the gel (this is due to deletion of the hybridising sequence from both Cβ1 alleles as a result of recombination). As for the Cβ2 locus, there are actually now two major bands corresponding to different "alleles" resulting from rearrangements on both chromosomes. The largest band, which is smaller than 4 kb, corresponds to a fragment of one of the two rearranged alleles. The lowest band is a fragment of the other rearranged allele. The intermediate minor band is probably derived from a subclone of Daudi cells with a different rearrangement—hence its presence in a submolar amount to either allele. Nonetheless, the rearranged state is very clearly shown in lane 1 where both major bands are clearly visible.

2 hours with the negative control antibody (TAL.1B5) which binds to the α-chain of MHC-DR actually results in the loss of the upper band, whereas the lowest band has a similar intensity to the untreated cells in lane 1 (see lane 2). A possible explanation for this is that the cells are differentiating, further resulting in a further recombination event at the Cβ2 locus of one allele, which leads to loss of Cβ2 sequences. This is entirely consistent with known phenomena.

24 hours with the negative control antibody appears to restore the three bands seen in the untreated cells (see lane 4). However the bands actually migrate at a lower position than the bands seen in lane 2. It is not quite clear how this has arisen. A possible explanation is that reintegration of deleted sequences has occurred, consistent with the looping-out-excision-reintegration model (Malissen et al., 1986, Nature 319: 28–32). Nonetheless, neither result seen with the TAL.1B5 antibody at 2 hours or 24 hours is indicative of a rearrangement to the germline pattern. Lanes 2 and 4 actually represent a negative control—the antibody to the α-chain does not result in restoration of the germline sequences.

By contrast, the results obtained with a monoclonal antibody (CR3/43) to the β-chain of MHC-DR after two hours show a pattern of bands that correspond to the germline configuration, namely a 12 kb band and a 4 kb band (compare lane 3 with lane A). In other words, these results show that the germline restriction pattern at the Cβ1 and Cβ2 loci has been restored for all alleles.

From these results we conclude that the pattern of bands seen in lane 3 are indicative of a rearrangement of the genomic DNA of the differentiated cells to regenerate the germline configuration.

The importance of this finding should not be understated. Never before has it been demonstrated that a genomic rearrangement, including deletions, can be reversed to restore the genome to the state in which it existed before the differentiation process took place. The most likely explanation is that the inversion caused by the rearrangement of the Cβ2 alleles during differentiation has been reversed, and the deletion of the Cβ1 sequence that caused loss of the 12 kb bands has also been reversed. The source of the missing Cβ1 sequence is likely to be episomal circular DNA present in the nucleus from the original deletion event. The existence of this circular DNA has been catalogued in the prior art (see references cited above). Nonetheless, the precise mechanism by which this restoration of the germline genome has occurred is not important. What is important is that it has occurred.

A continued incubation with the monoclonal antibody (CR3/43) to the β-chain of MHC-DR for 24 hours results in a more complex banding pattern (lane 5). However these bands do not represent the same bands as in the untreated control. In particular, fragments of about 12 kb that hybridize to the probe are still present ("Cβ2 alleles"). Further, it is important to appreciate that the bands marked "Cβ2 alleles" do not correspond to the smaller than 4 kb band seen in the untreated control (lane 1). The most likely explanation for the results seen in lane 5 is that a secondary rearrangement process has occurred since the hybridization pattern resembles that of T-cells in that it is characterized by a rearranged TCR gene (this explanation is consistent with the flow cytometry data showing an increase in cells having cell markers characteristic of T cells). Nonetheless, regardless of the precise molecular explanation, the results seen in lane 5 at 24 hours exposure to the CR3/43 antibody are supportive of the results obtained at 2 hours exposure in lane 3.

2. Rearrangement of Ig Gene in B-CLL Cells

Figure 17:
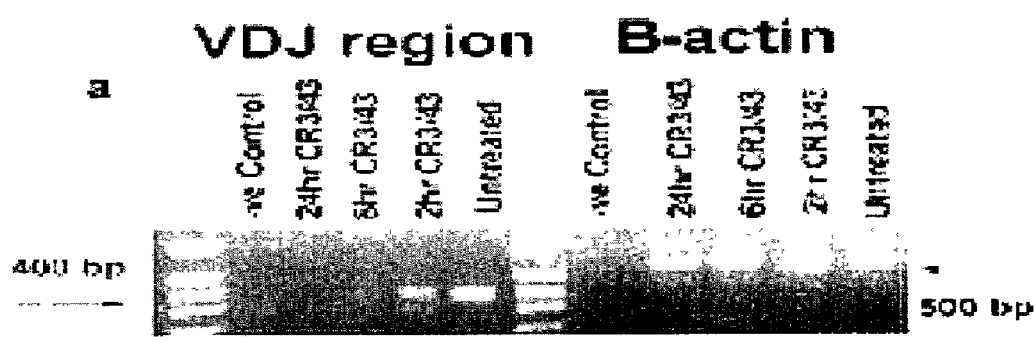
FIG. 17 is (A) a photograph of an agarose gel containing PCR products resolved by electrophoresis and stained with ethidium bromide and (B) a photograph of a Southern blot.
Figure 17:

The Southern blot shown in FIG. 17B was obtained using peripheral blood cells from patients with chronic lymphocytic leukemia (B-CLL). Genomic DNA was prepared from these largely monoclonal B cells and digested with BamHI and HindIII, subjected to gel electrophoresis and probed with a labeled TCR DNA probe. These B-CLL cells were treated for 24 hours with the CR3/43 (anti class II MHC chain of HLA-DR, DP and DQ) which was described above. The blots were probed with a radiolabeled Ig J region probe. The two bands obtained from the untreated cells in lane A, represent the two rearranged Ig alleles (paternal and maternal). These bands did not appear in lane B which shows the pattern 24 hours after antibody treatment of cells. In their place appeared a 5.4 kb band characteristic of the germ line Ig gene.

In another experiment, shown in FIG. 17A, cells were left untreated or treated for the times indicated with the anti-class II MHC β-chain antibody. The Ig VDJ region was amplified by PCR in the differentiated (control) and antibody-treated B-CLL cells (left half of gel). This generated a VDJ amplification product from the untreated cells. However, no such band was observed in the antibody-treated cells because, as a result of insertion of the excised genomic DNA, this "germ line" DNA configuration was not susceptible to PCR amplification using the particular primers for VDJ. A similar experiment (right side of gel) allowed me to visualize the behavior of a control, housekeeping, gene encoding β-actin. There was no difference in the β-actin PCR amplification product, regardless of treatment. Thus, this "control" gene did not appear to be affected by the retrodifferentiation process that caused profound alterations in the Ig gene of the same cells under the same conditions.

The results presented above show that treatment of cells with an agent that engages an appropriate cell surface receptor induces retrodifferentiation of these cells that is proven at the molecular level (and monitored) by observing the retrogression of the rearrangements of chromosomal DNA that characterize the differentiated state. Thus, it is concluded on the basis of the molecular genetic and morphological evidence that cells of the B lymphocyte lineage, treated with an agent (mAb) that engages the class II MHC β-chain, undergo retrodifferentiation. By contrast, the same cells treated with antibodies that engage class II α-chain are not similarly induced to retrodifferentiate. If anything, they appear to differentiate (forward) along the B cell pathway.

F. Further Studies on Retrodifferentiation of B Lymphocytes

FACsVantage puried BCLL cells (95% pure B cells0 from BCLL patients were treated with the CR3/43 antibody as described above and the cells processed by flow cytometry. The results shown below in Table A confirm further the results obtained above. A significant increase in the number of $CD34^+$ cells was obtained together with a large reduction in the number of cells having cell surface markers characteristic of the B lymphocyte lineage (CD19, CD20 and CD22). An important point to note from Table A is that it also shows an increase in the number of cells that are both CD34 negative and lineage negative. These undifferentiated cells are not committed to the haemopoietic lineage and precede $CD34^+$ stem cells in differentiation. Further, examination of samples by light microscopy showed a range of adherent cell types having morphological characteristics of non-haemopoietic cells.

TABLE A

| Marker | 0 hr | 2 hr | 24 hr |
|---|---|---|---|
| CD20 | 73 | 67 | 16 |
| CD14 | 0 | 3 | 23 |
| CD34 | 0 | 1 | 23 |
| CD7 | 0 | 2 | 0 |
| CD16 | 8 | 3 | 2 |
| CD19 | 95 | 71 | 1 |
| CD22 | 5 | 3 | 2 |
| CD33 | 0 | 0 | 0 |
| CD3 | 0 | 0 | 0 |

Figure 21:
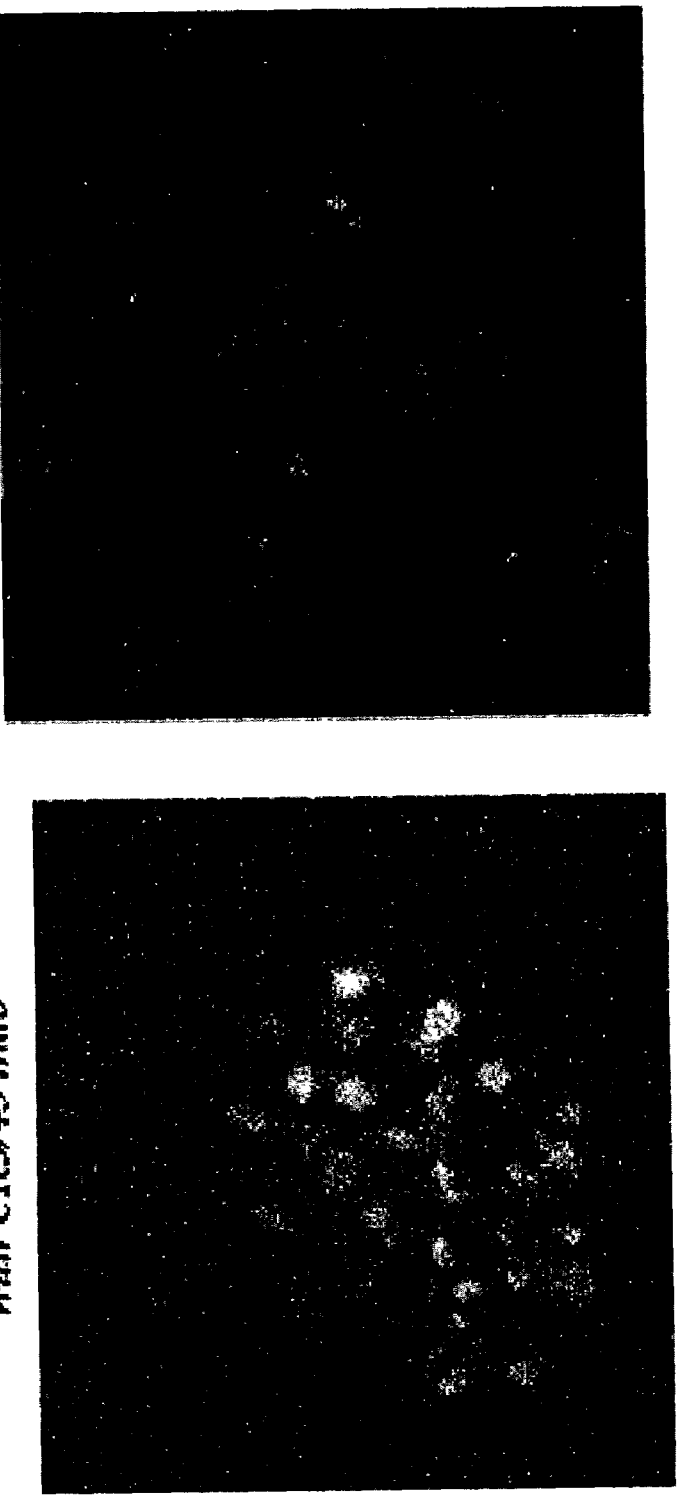
FIG. 21 is a confocal microscopy image of cells before and after treatment according to the methods of the invention.

The loss of CD19 cell surface markers accompanied by the appearing of CD34 cell surface markers on the same cell has also been demonstrated and recorded on video in real time using confocal microscopy. B-lymphocytes before the addition of CR3/43 mab stained green with a FITC conjugated monoclonal antibody to CD19. After the addition of CR3/43 mab, cells lost their green fluorescence and began to stain red with a PE/Cy5 (or quantum red) conjugated monoclonal antibody to CD34 but not green (see FIG. 21 which shows two still images from the timelapse video). The results clearly confirm that during B lymphocyte retrodifferentiation, lineage specific markers such as CD19 are lost whilst a stem cell marker such as CD34 is re-expressed.

Figure 18:
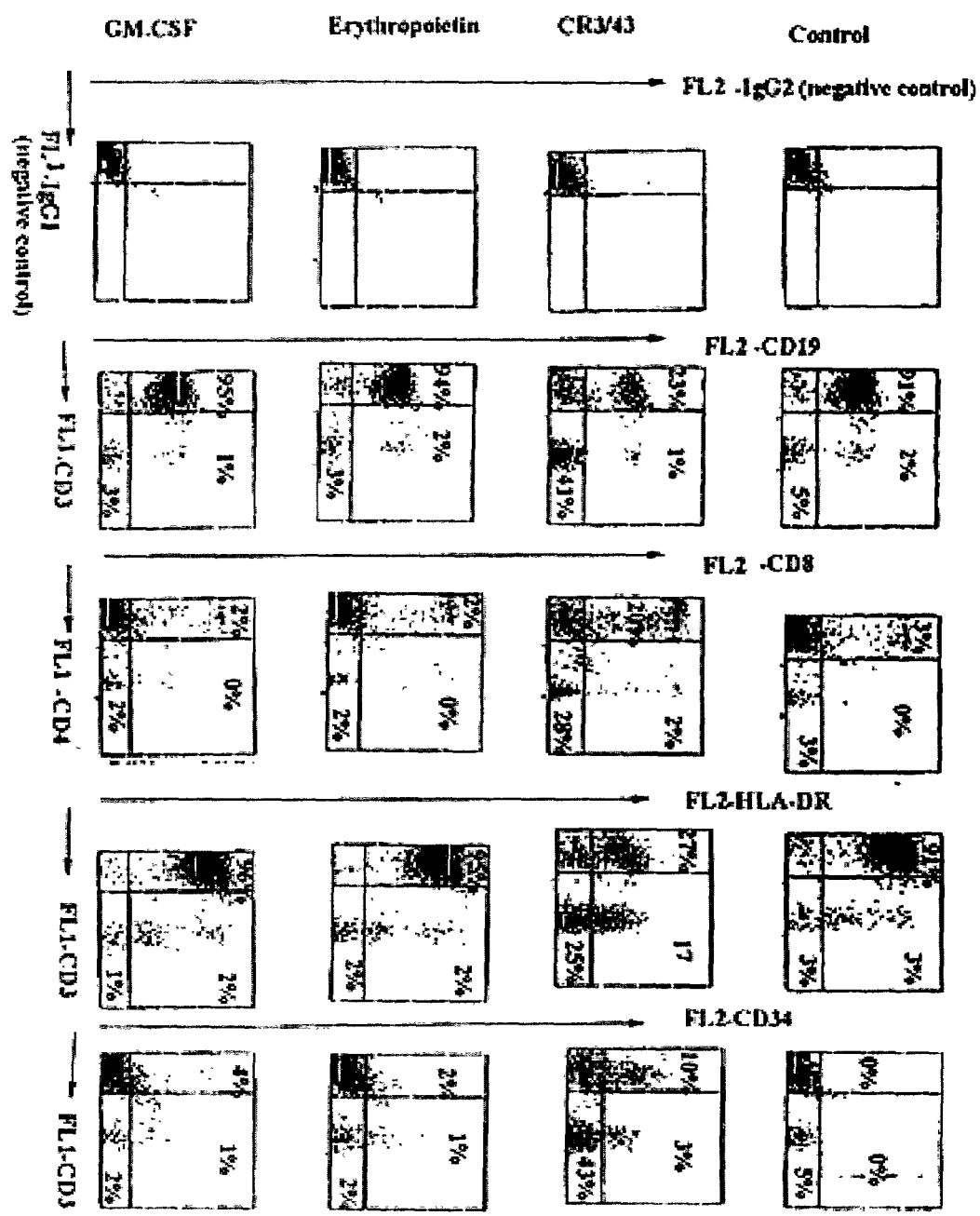
FIG. 18 depicts scatter graphs showing flow cytometry results for healthy cells treated with one of three different agents.

G. Other Agents that Induce Retrodifferentiation of B Lymphocytes to Haemopoietic Stem Cells Initial studies actually identified three agents—granulocyte/monocyte-colony stimulating factor (GM-CSF), erythropoietin and mAb CR3/43. A preparation of enriched, purified, normal B lymphocytes was treated with one of these three agents in a similar manner to that described for CR3/43 and TAL.1B5 above and treated samples examined by flow cytometry as described above. Compared with the negative control, all three samples treated with either GM-CSF, erythropoietin or mAb CR3/43 showed changes consistent with retrodifferentiation. In particular, all three agents increased the relative number of $CD34^+$ cells in the cell population (see FIG. 18). The greatest effect, however, was seen with CR3/43 and consequently, this agent was selected for use in the more detailed studies presented herein.

H. Properties of Haemopoietic Stem Cells Produced by the Retrodifferentiation Process Colony Forming Assays To confirm that the $CD34^+$ cells observed by flow cytometry and the undifferentiated cells identified by microscopy had the properties of undifferentiated haemopoietic cells, blood samples treated with an antibody to the class II MHC β-chain (CR3/43—see above) were subjected to colony forming assays—a standard method known in the art for assessing the capabilities of primitive haemopoietic cells.

In vitro clonal assays for hematopoietic stem cell allows the quantification of primitive progenitor cells that possess the ability to proliferate, differentiate and develop into phenotypically and functionally mature myeloid and/or erythroid cells. For example in the presence of growth factors stem cell when seeded/immobilised in soft-gel matrix in vitro are capable of clonal growth (proliferation) and differentiation.

Figure 19:
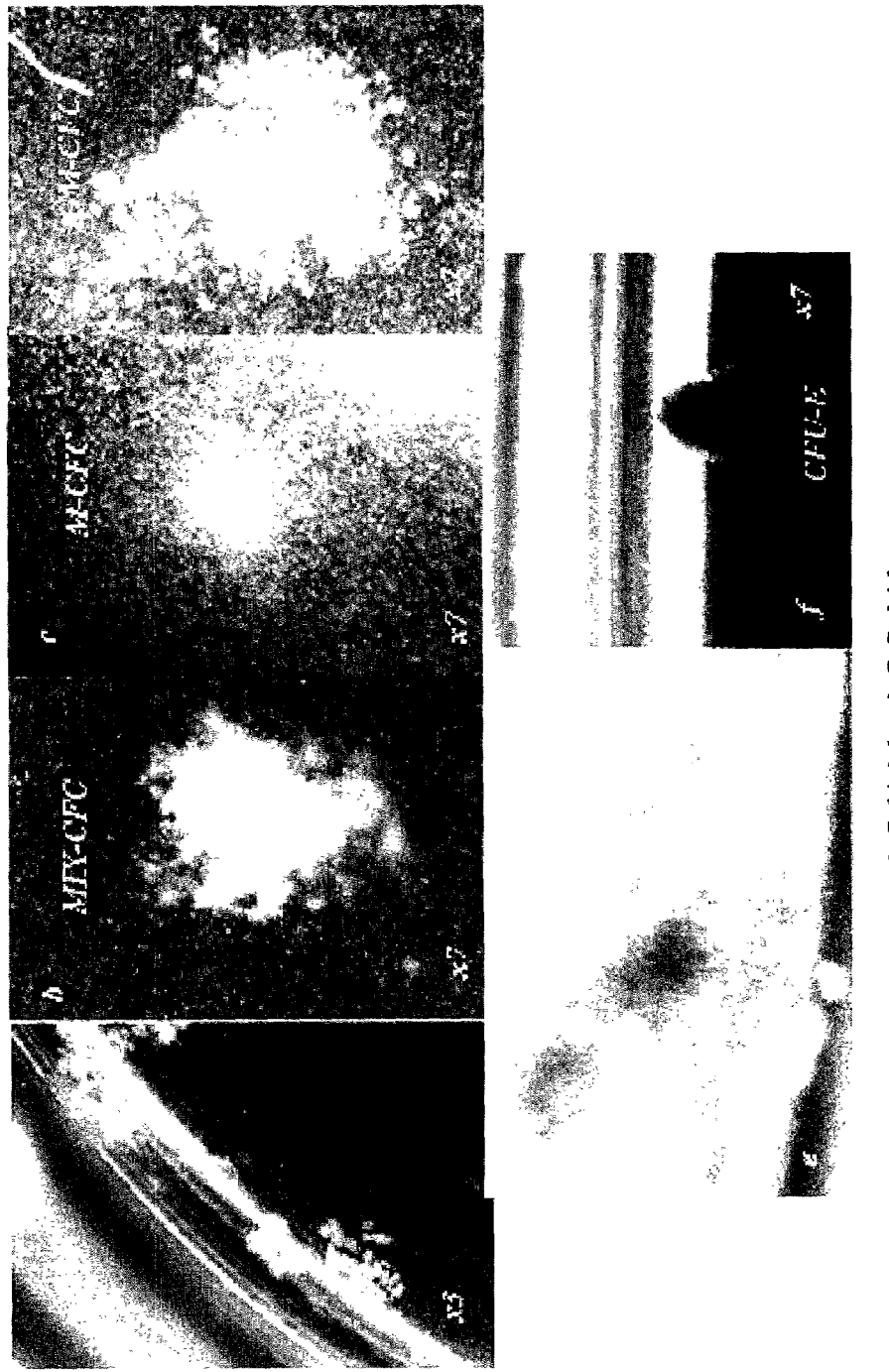
FIG. 19 is a photomicrograph showing the results of a colony forming assay conducted using purified normal B cells treated according to the methods of the invention.

FIG. 19 is a colony assay of stem cells produced according to the methods of the invention, using inverted brightfield microscopy. In this assay B cells obtained from buffy coat of healthy blood donors were treated with CR3/43 mab and then subjected to colony assays as described in the materials and methods section.

Panels (a) to (e) in FIG. 19 show:
a) Bright field microscopy of culture dish viewed at ×3 magnification showing erythroid, myeloid and mixed (consisting of mature myeloid and erythroid cells) colonies which can be seen readily even by the naked eye. Each colony arose from a single haematopoietic stem cell by proliferation and subsequent differentiation.
b) MIX-CFC this colony arose from a single multi-potent haematopoietic stem cell (stem cells capable of giving rise to cells of myeloid and erythroid lineages.
c) M-CFC this colony consists of macrophages.
d) GM-CFC this colony consist of the myeloid lineage including macrophages, granulocyte and megakaryocytes
e) BFU-E this colony consists of cells belonging to the erythroid lineage such as normoblasts and non-nucleated red cells. The red colouration of cells shows that they are well hemogloblinized. The large size of this colony indicates that it arose from an extremely primitive stem cell.

The same results were obtained with B-CLL cells (data not shown). Untreated B cells did not give rise to haematopoietic colonies (data not shown). These results therefore demonstrate the presence of viable haemopoietic stem cells in blood samples treated with monoclonal antibody CR3/43 to the class II MHC β-chain but not in untreated blood samples.

Long Term Culture

The long-term assay examines the self-renewal potential of haemopoietic stem cells. In this culture most components of bone marrow haematopoiesis are reproduced in vitro. The important feature of this culture is sustained haematopoiesis, which occurs in the absence of added growth factors. In this assay the process of hematopoiesis is absolutely dependent upon the establishment of an adherent layer of bone marrow derived stromal cells. Stromal cells (consisting of a variety of non-haemopoietic cells e.g., fibroblast, fat cells and including all cell types belonging to the mesenchymal system) support haematopoiesis by providing the appropriate environment (secretion of growth factors and synthesis of extracellular matrix) to promote the survival, self-renewal, proliferation and differentiation of the stem cells.

In this assay, treatment of B cells obtained from buffy coats of healthy blood donors (the same results were obtained with B-CLL cells) with CR3/43 mab gave rise to the formation of an adherent cell layer within hours of adding the antibody which, also increased with time.

Figure 20:
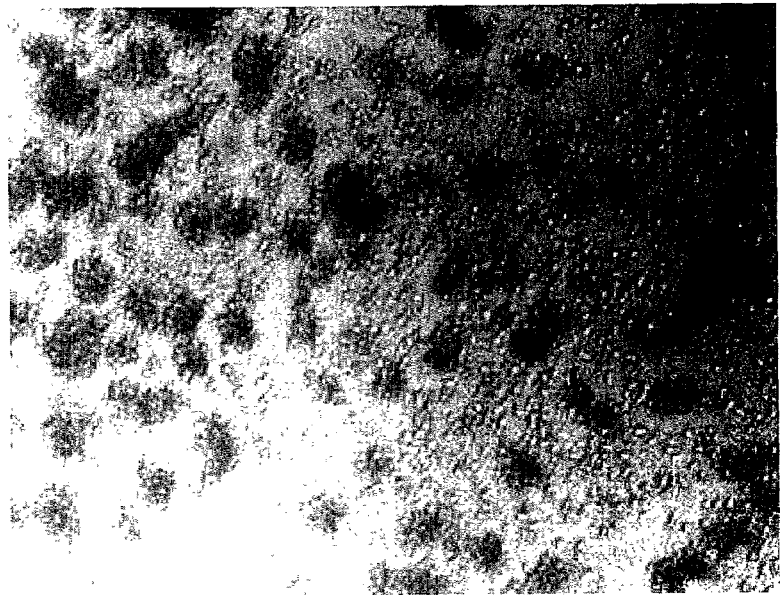
FIG. 20 is a photomicrograph, using inverted bright field microscopy, showing the establishment of a long-term culture of stem cells (undifferentiated) produced according to the present invention (3 days following treatment).
Figure 20:
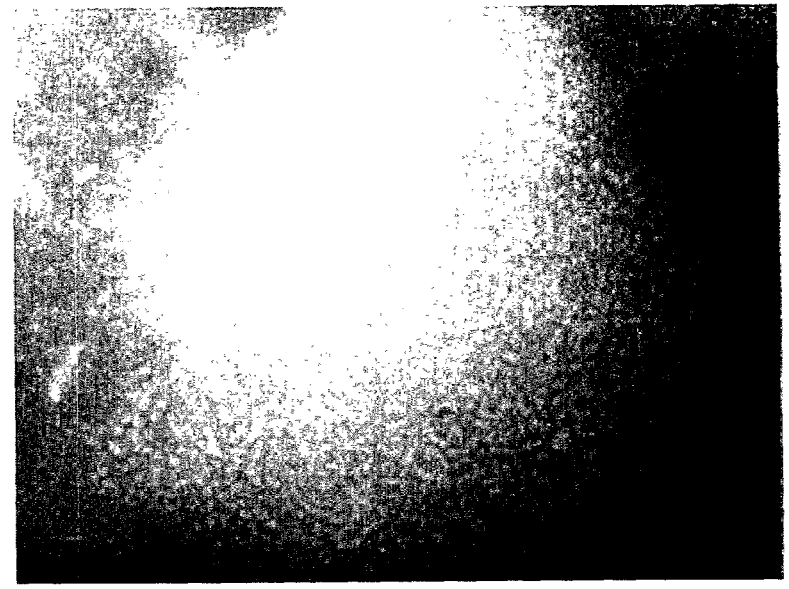

The adherent layer consisted of stromal cells (blanket cells, consisting mainly of fibroblast/mesenchymal-type cells/light refringent large cells when viewed with inverted bright field microscopy—see FIG. 20) which supported the growth and development of haematopoietic cells up to 12 weeks and longer (these cells show intimate contact with haematopoietic cells). Also visible in the adherent layer are groups of primitive haematopoietic cells (also known as cobblestone areas/clusters of dark appearing cells) which are the origin of prolonged production of haematopoietic cells.

The non-adherent layers which are on top of the stromal layer (clusters of bright appearing cells) consisting of small round cells forming clusters of haematopoietic foci. This layer contains stem cells and also more committed progenitors of the haematopoietic system. The non adherent layer was capable of giving rise to MIX-CFC, GM-CFC, M-CFC, BFU-E (as determined using the clonal assay) and CFU-F (colony forming unit-fibroblast) (when sub-cultured with long term culture medium).

I. RT-PCR of Cells Treated with an Antibody to the β-Chain of HLA-DR.

Gene transcription was measured in Ramos (B lymphoma) and K562 (erythroid leukaemia) cells treated with the CR3/43 mab for the CD34, c-kit (ligand of stem cell factor), $\epsilon$-haemoglobin (embryonic form of haemoglobin) and β-actin genes.

Methods mRNA was extracted before and after treatment with CR3/43 mab using RNAZOL (CINA BIOTECH). mRNA were subjected to hexamer priming reverse transcription by incubating at room temperature for 5 mins with 4 µl standard buffer, 2 µl dNTPs, 1 µl RNASIN, 1 µl reverse primer (random hexamer primer) and 1 µl MMLV reverse transcriptase enzyme. This mixture was further incubated for 1 hr at 38° C. Mixtures were then subjected to PCR under standard conditions using primers designed to amplify CD34, c-kit, $\epsilon$-haemoglobin and β-actin sequences. Primers were synthesised at the Randell Institute Kings College according to published data.

Results

The results obtained show that whereas the levels of β-actin mRNA did not change, the levels of CD34, c-kit and $\epsilon$-haemoglobin mRNA all increased significantly following treatment with the CR3/43 mAb. The results for CD34 and c-kit provide further support for the data detailed above that demonstrate the retrodifferentiation of B lymphocytes to produce haemopoetic stem cells.

The results obtained for the $\epsilon$-haemoglobin are even more interesting since $\epsilon$-haemoglobin is normally only expressed in embryonic cells. It is therefore possible that treatment with the CR3/43 mAb not only gives rise to haemopoietic stem cells but also to even more primitive undifferentiated cells such as embryonic stem cells.

J. Summary

In short, the examples describe in vitro experiments that reveal extremely interesting, seminal findings regarding the ontogeny and development of T and B lymphocytes which can be utilised in the generation of stem cells to affect lymphohaematopoiesis in peripheral blood samples in a matter of hours.

Treatment of peripheral blood samples obtained from patients with B-cell chronic lymphocytic leukaemia's (B-CLL) with high B lymphocyte counts, with monoclonal antibody to the homologous region of the β-chain of class-II antigens gave rise to a marked increase in the relative number of single positive (SP) T lymphocytes and their progenitors which were double positive for the thymocyte markers CD4 and CD8 antigens and these were coexpressed simultaneously. However, these phenomena were always accompanied by a significant decrease in the relative number of B-lymphocytes. These observations were not noted when the same blood samples were treated with monoclonal antibodies to the homologous region of the α-chain of class-II antigens or to the homologous region of class-I antigens.

Treatment of whole blood obtained from patients with B-cell chronic lymphocytic leukaemia (CLL) with monoclonal antibody to the homologous region of the B chain of the HLA-DR antigen appeared to give rise to T-lymphopoiesis. This event was marked by the appearance of double positive cells coexpressing the CD4 and CD8 markers, the appearance of cells expressing CD34 and the concomitant increase in the number of single positive $CD4^+$ $CD3^+$ and $CD8^+$ $CD3^+$ lymphocytes. Furthermore, the immunophenotypic changes that took place in the generation of such cells were identical to those cited for thymocyte development, especially when measured with time.

The percentages of double positive cells (DP) generated at 2 hour incubation time of whole blood with monoclonal antibody to the homologous region of the β-chain of the DR antigen, decreased with time and these events were accompanied by increase in the percentages of single positive $CD4^+$ $CD3^+$ and $CD8^+$ $CD3$ cells simultaneously and at later times too. TCR α and β chains were also expressed on these types of cells.

B-lymphocytes were constantly observed to lose markers such as CD19, CD21, CD23, IgM and DR and this coincided with the appearance of $CD34^+$ and $CD34^+$ $CD2^+$ cells, increases in $CD7^+$ cells, increases in $CD8^+$ $CD28^+$ and $CD28^+$ cells, increases in $CD25^+$ cells, the appearance of $CD10^+$ and $CD34^+$ cells and $CD34^+$ and $CD19^+$ cells increases in $CD5^+$ cells, and cells expressing low levels of CD45 antigen. These changes were due to treatment of blood with monoclonal antibody to the homologous region of the β-chain of HLA-DR antigen.

The immunophenotypic changes associated with such treatment is consistent with retrodifferentiation and subsequent commitment (i.e. recommitment) of B lymphocytes, because the majority of white blood cells in blood of patients with B-CLL before treatment were B lymphocytes. Furthermore, B-lymphocytes of patients with B-CLL which were induced to become T-lymphocytes following treatment with cyclophosphamide and monoclonal antibody to the β-chain of HLA-DR antigen, were able to revert back to B lymphocytes following prolonged incubation with this treatment.

On analysis of treated samples with monoclonal antibody to the β-chain of HLA-DR antigen, with CD16&56 and CD3 and CD8 and CD3 panels, the relative number of cells expressing these markers steadily increases in increments consistent with those determined with panels such as CD19 and CD3 and DR and CD3. Investigation of the supernatant of treated and untreated samples of patients with HIV infection using nephlometry and immunoelectrophoresis reveals increased levels of IgG indicating that the B-cells must have passed through the plasma cell stage. The increase in the relative number of all above-mentioned cells was also accompanied by the appearance of medium size heavily granulated cells expressing the CD56&16 antigens in extremely high amounts. Other cells which were extremely large and heavily granulated were observed transiently and these were positive for CD34 and double positive for CD4 CD8 markers. Other transient cells were also observed and these were large and granular and positive for the CD3 and CD19 receptors. CD25 which was present on the majority of B-lymphocytes was lost and became expressed by newly formed T-lymphocytes which were always observed to increase in number.

$CD28^+CD8^+$ and $CD28^+$ cells appeared after treatment of whole blood of patients with B-CLL with monoclonal antibody to the homologous region of the B chain of the DR antigen. These findings were due to treatment of blood with monoclonal antibody to the homologous region of the β-chain of HLA-DR antigen.

T-lymphopoiesis generated in this manner was also observed in peripheral blood of healthy blood donors, cord blood, bone marrow, patients with various infections including $HIV^+$ individuals and AIDS patients, enriched fractions for B lymphocytes obtained from blood samples of healthy blood donors, IgA deficient patients and other patients with various other conditions. Furthermore, analysis of myeloid markers in treated samples of two patients with B-CLL with monoclonal antibody to the homologous region of the β-chain of the HLA-DR antigen showed a significant increase in the relative number of cells expressing the myeloid markers such as CD13 and CD33. These markers were coexpressed with the CD56 & 16 or the CD7 antigens. However, the relative number of $CD7^+$ cells with T-lymphocyte markers and without myeloid antigens was observed on a separate population of cells. These particular observations were not seen in untreated samples or in samples treated with monoclonal antibodies to class I antigens or the homologous region of the α-chain of HLA-DR antigen (see Charts 2 & 3). These final results suggest that B-lymphocytes once triggered via the β-chain of the HLA-DR antigen are not only able to regress into T lymphocyte progenitor cells but are also capable of existing into the myeloid and erythroid lineages.

Thus in summary, the data presented in the present application demonstrate that (i) it is possible to convert healthy cells from one lineage to cells having the cell surface markers and morphological characteristics of cells of several other lineages and (ii) it is possible to obtain cells having the cell surface markers and morphological characteristics of primitive precursor cells (for example stem cells), from differentiated B lymphocytes and T lymphocytes.

It should be noted that a number of experiments have been carried out with BCLL cells. BCLL cells are mature B lymphocytes that are incapable of differentiating to the final terminally differentiated stage of a plasma cell. Instead, due to a chromosome defect, they exhibit high levels of proliferation, hence the large numbers of B lymphocytes in the blood of BCLL patients. By contrast to a number of tumour cells described in the prior art, BCLL cells have not undergone any form of limited reverse differentiation prior to use in the methods of the invention. Furthermore they do not exhibit any characteristics of undifferentiated cells in term of genomic structure, cell markers or cell morphology. They are in all respects mature B lymphocytes.

Thus whereas some malignant cells may have to a limited extent some characteristics of undifferentiated cells, this is not the case for BCLL cells, which are a perfectly acceptable experimental system for studying B lymphocytes. In fact BCLL and Daudi cells are not sufficiently distinguished from normal cells in any aspects relevant to these experiments. Indeed, the suitability of BCLL cells as a model system is confirmed by Martensson et al., 1989, Eur. J. Immunol. 19: 1625–1629 (see page 1625 rhs, $1^{st}$ para).

It should be noted that the stem cells that are produced by the method of the present invention may be stem cells of any tissue and are not necessarily limited to lymphohaematopoietic progenitor cells.

Other modifications of the present invention will be apparent to those skilled in the art.

TABLE 1

CLINICAL DIAGNOSIS OF PATIENTS AND EXPERIMENTAL CONDITIONS OF BLOOD SAMPLES INCLUDING COULTER COUNTS (WBC) FOLLOWING AND PRIOR TREATMENT OF BLOOD SPECIMENS WITH VARIOUS MONOCLONAL ANTIBODIES AND OTHER AGENTS

| PATIENT ID | DIAGNOSIS | EXPT COND | WBC/L X10-9 B | A | % LYMPH B | A | #LYMPH/L 10X-9 B | A | AGENT ML/mL |
|---|---|---|---|---|---|---|---|---|---|
| 1 | B-CLL | 12 HR AT 22 C. | 100 | ND | 86.1 | ND | 86.1 | ND | ANTI-B 50 |
| 2 | B-CLL | 2 HR AT 22 C. | 39.1 | 9.6 | 74.4 | 63.3 | 29.9 | 6.1 | ANTI-B 50 |
|   |   | 2 HR AT 22 C. | 39.1 | 37.7 | 74.4 | 75.1 | 29.9 | 28.3 | ANTI-B PE 50 |
| 3 | B-CLL | 6 HR AT 22 C. | 39.5 | 9.3 | 71.9 | 67.2 | 28.3 | 6.2 | ANTI-B 50 |
|   |   | 6 HR AT 22 C. | 39.5 | 37.7 | 71.9 | 72.5 | 28.3 | 27.4 | ANTI-B PE 50 |
| 4 | B-CLL | 24 HR AT 22 C. | 39 | 9.3 | 73 | 66.5 | 28.4 | 6.2 | ANTI-B 50 |
|   |   | 24 HR AT 22 C. | 39 | 36.2 | 73 | 70.4 | 28.4 | 25.5 | ANTI-B PE 50 |

TABLE 1-continued

CLINICAL DIAGNOSIS OF PATIENTS AND EXPERIMENTAL CONDITIONS OF
BLOOD SAMPLES INCLUDING COULTER COUNTS (WBC) FOLLOWING AND
PRIOR TREATMENT OF BLOOD SPECIMENS WITH VARIOUS MONOCLONAL
ANTIBODIES AND OTHER AGENTS

| PATIENT ID | DIAGNOSIS | EXPT COND | WBC/L X10-9 B | A | % LYMPH B | A | #LYMPH/L 10X-9 B | A | AGENT ML/mL |
|---|---|---|---|---|---|---|---|---|---|
| 5 | B-CLL | 2 HR AT 22 C. | | | | | | | ANTI-B 50 ANTI-A 50 ANTI-I 50 ANTI-B & TOXIC AGENT 25 + 25 |
| 6 | B-CLL | 24 HR AT 22 C. | | | | | | | ANTI-B 50 |
| 7 | B-CLL | 24 HR AT 22 C. | 170 | 128 178 130 | 95.4 | 91.1 94.2 90.4 | 16.9 | 11.6 16.8 11.9 | ANTI-B 10 ANTI-I 10 ANTI-B & TOXIC AGENT 10 + 20 |
| 8 | B-CLL | 24 HR AT 22 C. | 16 | 7 | 81.9 | 51.2 | 14 | 3.0 | ANTI-B 20 |
| 9 | B-CLL | 12 HR AT 22 C. | +++ | 89.5 +++ +++ 95.4 | 87 | 85.1 85.4 89.4 84.9 | +++ | 76.2 +++ +++ | ANTI-B 30 ANTI-I 30 ANTI-4 30 ANTI-I + II + 4 10 + 10 + 10 |
| 10 | B-CLL | 2 HR AT 22 C. | 19.3 | ND | 86 | ND | 16.7 | ND | ANTI-B 30 ANTI-I 30 |
| 92 | OUT PATIENT | 2 HR AT 22 C. | 5.4 | ND | 74.5 | ND | | ND | ANTI-B 20 |
| 87 | OUT PATIENT | 2 HR AT 22 C. | 4.8 | ND | 59.3 | ND | | ND | ANTI-B 20 |
| 91 | OUT PATIENT | 2 HR AT 22 C. | 4.2 | ND | 54.0 | ND | | ND | ANTI-B 20 |
| 21 | OUT PATIENT | 2 HR AT 22 C. | 3.9 | ND | 47.4 | ND | | ND | ANTI-B 20 |
| 34 | OUT PATIENT | 2 HR AT 22 C. | 7.2 | ND | 20.0 | ND | | ND | ANTI-B 20 |
| 36 | CMV INFANT | 4 HR AT 22 C. | 13.4 | ND | 7.3 | ND | | ND | ANTI-B 20 |
| 93 | HIV+ INFANT | 4 HR AT 22 C. | 5.6 | ND | 43.4 | ND | | ND | ANTI-B 20 |
| BB/ST | 40% BLAST IN BLOOD 6 DAYS OLD | 2 HR AT 22 C. 24 HR AT 22 C. | 60.5 | ND | 20.2 | ND | 12.2 | ND | ANTI-B 50 ANTI-A 50 ANTI-AB 25 + 25 |
| HIV25 | AIDS | 2 HR AT 22 C. | 7.5 | ND | 34.8 | ND | 2.6 | ND | ANTI-B 50 ANTI-A 50 ANTI-AB 25 + 25 |
| 43/BD | B CELL DEFICIENT | 4 HR AT 22 C. | | | | | | | ANTI-B 20 ANTI-I 20 ANTI-4 20 |
| OB/BD | B CELL DEFICIENT | 4 HR AT 22 C. | | | | | | | ANTI-B 20 ANTI-I |

TABLE 1-continued

CLINICAL DIAGNOSIS OF PATIENTS AND EXPERIMENTAL CONDITIONS OF BLOOD SAMPLES INCLUDING COULTER COUNTS (WBC) FOLLOWING AND PRIOR TREATMENT OF BLOOD SPECIMENS WITH VARIOUS MONOCLONAL ANTIBODIES AND OTHER AGENTS

| PATIENT ID | DIAGNOSIS | EXPT COND | WBC/L X10-9 B | WBC/L X10-9 A | % LYMPH B | % LYMPH A | #LYMPH/L 10X-9 B | #LYMPH/L 10X-9 A | AGENT ML/mL |
|---|---|---|---|---|---|---|---|---|---|
| HIV+ | AIDS | 6 HR AT 22 C. | | | | | | | 20 ANTI-4 20 ANTI-B 20 ANTI-I |
| IgA-D | IgA DEFICIENT | 6 HR AT 22 C. | | | | | | | 20 ANTI-B 20 ANTI-I 20 |

EXPT COND: EXPERIMENTAL CONDITIONS
B: BEFORE
A: AFTER
ANTI-B: monoclonal antibody to the homologous region of the β-chain of HLA-DR anigen
ANTI-A: monoclonal antibody to the homologous region of the α-chain of HLA-DR antigen
ANTI-I: monoclonal antibody to the homologous region of Class I antigens
ANTI-AB: both ANTI-B and ANTI-A added togather
ANTI-4: monoclonal antibody to the CD4 antigen
ANTI-I + II + 4: ANTI-I and ANTI-B and ANTI-4 added togather
Cytoxic agent: Cyclophophamide
ML/ml: micro litre per ml
L: litre

TABLE 2

IMMUNOPHENOTYPING OF PATIENTS WITH B-CLL AND OTHER CONDITIONS BEFORE AND AFTER TREATMENT OF BLOOD SAMPLES WITH MONOCLONAL ANTIBODY TO THE HOMOLOGOUS REGION OF THE B CHAIN OF THE HLA-DR WITH CD19 AND CD3 MONOCLONAL ANTIBODIES.

| PATIENT | % CD19+ B | % CD19+ A | % CD3+ B | % CD3+ A | % CD19+ CD3+ B | % CD19+ CD3+ A | % CD3− CD19− B | % CD3− CD19− A | % CD19+ HGCD3− FC+ B | % CD19+ HGCD3− FC+ A |
|---|---|---|---|---|---|---|---|---|---|---|
| 1 | 88 | 40 | 5 | 19 | 1 | 2 | 6 | 26 | 0 | 12 |
| 2 | 73 | 15 | 10 | 33 | 2 | 7 | 15 | 41 | 0 | 5 |
| 3 | 73 | 11 | 11 | 33 | 2 | 2 | 14 | 52 | 0 | 2 |
| 4 | 71 | 13 | 11 | 37 | 2 | 2 | 16 | 47 | 0 | 2 |
| 5 | 85 | 40 | 5 | 16 | 1 | 1 | 6 | 26 | 3 | 18 |
| 6 | 85 | 43 | 5 | 18 | 1 | 1 | 6 | 27 | 3 | 10 |
| 7 | 90 | 72 | 2 | 4 | 0 | 2 | 7 | 8 | 0 | 14 |
| 8 | 62 | 25 | 7 | 13 | 0 | 1 | 29 | 55 | 2 | 6 |
| 9 | 90 | 85 | 2 | 3 | 0 | 0 | 2 | 1 | 1 | 4 |
| 10 | 78 | 50 | 7 | 14 | 0 | 0 | 14 | 26 | 0 | 8 |
| 92 | 12 | 10 | 38 | 49 | 0 | 1 | 49 | 40 | 0 | 0 |
| 91 | 7 | 3 | 35 | 29 | 0 | 1 | 59 | 67 | 0 | 0 |
| 87 | 5 | 3 | 32 | 38 | 1 | 1 | 63 | 58 | 0 | 0 |
| 21 | 1 | 1 | 27 | 29 | 1 | 0 | 71 | 70 | 0 | 0 |
| 34 | 1 | 1 | 13 | 13 | 0 | 2 | 86 | 84 | 0 | 0 |
| 39 | 10 | 6 | 23 | 25 | 0 | 0 | 67 | 69 | 0 | 0 |
| 93 | 6 | 3 | 26 | 27 | 1 | 1 | 68 | 70 | 0 | 0 |
| BB/ST | 1 | 1 | 12 | 13 | 0 | 0 | 87 | 86 | 0 | 0 |
| HIV25 | 7 | 2 | 26 | 27 | 0 | 0 | 68 | 67 | 0 | 0 |
| 43/BD | 0 | 0 | 40 | 42 | 0 | 1 | 58 | 54 | 0 | 0 |
| 04/BD | 0 | 0 | 49 | 41 | 0 | 3 | 43 | 41 | 0 | 0 |
| HIV+ | 1 | 1 | 10 | 14 | 0 | 0 | 89 | 87 | 0 | 0 |
| IgA/D | 10 | 1 | 21 | 25 | 2 | 3 | 67 | 71 | 0 | 0 |

B: before treatment
A: after treatment

TABLE 3

IMMUNOPHENOTYPING OF PATIENTS WITH B-CLL AND OTHER CONDITIONS BEFORE AND AFTER TREATMENT OF BLOOD SAMPLES WITH MONOCLONAL ANTIBODY TO THE B CHAIN OF THE HOMOLOGOUS REGION OF THE HLA-DR WITH MONOCLONAL ANTIBODIES TO CD4 AND CD8.

| | % CD8+ | | % CD4+ | | % CD4 + CD8+ | | % CD4 − CD8− | | CD4 + LOW | |
|---|---|---|---|---|---|---|---|---|---|---|
| PATIENT | B | A | B | A | B | A | B | A | B | A |
| 1 | 2.8 | 16 | 2.9 | 11.4 | 0 | 3.2 | 93.1 | 67.6 | 0 | 0 |
| 2 | 6.2 | 13.2 | 9.1 | 24.3 | 0 | 9.4 | 78.7 | 46 | 5.8 | 6.3 |
| 3 | 7.2 | 13.1 | 7.4 | 23.9 | 0 | 8.2 | 78.8 | 48.1 | 6.3 | 6.6 |
| 4 | 10.1 | 24.2 | 7.6 | 24.9 | 0.3 | 2.8 | 77.5 | 42 | 4.6 | 5 |
| 5 | 2.9 | 16.2 | 1.8 | 7.6 | 0 | 2 | 95 | 62.3 | 0 | 0 |
| 6 | ND | 12 | ND | 8.1 | ND | 1.7 | ND | 75.7 | ND | 0 |
| 7 | 1.9 | 2.6 | 1.9 | 2.8 | 0 | 0 | 95.8 | 94.3 | 0 | 0 |
| 8 | 3.2 | 7 | 3.9 | 6.9 | 0.1 | 2 | 87.3 | 79.8 | 4.3 | 6 |
| 9 | 2.8 | 2.9 | 3 | 3 | 0 | 0 | 94 | 94.1 | 0 | 0 |
| 10 | 5.7 | 9.4 | 4.7 | 9.1 | 0.6 | 0.8 | 88.7 | 79.2 | 0 | 0 |
| 92 | 21 | 19 | 21.6 | 21 | 0.8 | 1.9 | 50.5 | 52.5 | 5.3 | 4.8 |
| 91 | 15.4 | 18.1 | 13.6 | 17.9 | 6.2 | 2.6 | 57 | 57.3 | 7.3 | 3.5 |
| 87 | 16.8 | 21.8 | 13.4 | 20.4 | 2.9 | 2.6 | 59.5 | 48.9 | 7 | 5.6 |
| 21 | 16 | 24.1 | 9.1 | 15.2 | 1 | 2.6 | 69.6 | 53.2 | 3.7 | 4.2 |
| 34 | 9.4 | 11.9 | 5.7 | 4.9 | 2 | 3.3 | 67.6 | 65.3 | 14.4 | 14.5 |
| 39 | 12.1 | 12.6 | 13.1 | 14.6 | 0.4 | 1.3 | 62.3 | 66.7 | 11.9 | 4.3 |
| 93 | 18.9 | 20.3 | 9.7 | 10.3 | 1.8 | 1.4 | 65.5 | 65.9 | 3.4 | 1.8 |
| BB/ST | 6.3 | 13 | 5.7 | 7.3 | 2.2 | 1.1 | 34.7 | 70.3 | 50.3 | 7.6 |
| HIV25 | 24.1 | 24.9 | 0.8 | 1.1 | 1.3 | 5 | 70.2 | 69.3 | 2.9 | 3.8 |

TABLE 4

IMMUNOPHENOTYPING OF PATIENTS WITH B-CLL AND OTHER CONDITIONS BEFORE AND AFTER TREATMENT OF SAMPLES WITH MONOCLONAL ANTIBODY TO THE B CHAIN OF THE HLA-DR WITH MONOCLONAL ANTIBODIES TO CD3 AND DR

| | DR+ | | CD+ | | CD + DR+ | | DR − CD3− | | DR + HCD3− | |
|---|---|---|---|---|---|---|---|---|---|---|
| PATIENT | B | A | B | A | B | A | B | A | B | A |
| 1 | 87 | 45.5 | 3.5 | 20.8 | 2.5 | 4.2 | 6.9 | 21.6 | 0 | 7.6 |
| 2 | 76.2 | 19.4 | 9.6 | 29.2 | 3.9 | 8.7 | 10.3 | 36.8 | 0 | 5.5 |
| 3 | 77.7 | 18.3 | 8.4 | 29.4 | 4.1 | 8.8 | 9.6 | 38.1 | 0 | 4.7 |
| 4 | 76.8 | 19.2 | 7.6 | 29.5 | 6.2 | 10.5 | 9.1 | 37.2 | 0 | 3.3 |
| 5 | ND | 47.1 | ND | 11.5 | ND | 9.9 | ND | 22.4 | ND | 7.3 |
| 6 | ND | | | | | | | | | |
| 7 | 91.4 | 85.8 | 2.4 | 2.5 | 0.7 | 0.7 | 5.1 | 4.2 | 0 | 6.3 |
| 8 | 61.8 | 28.9 | 6.5 | 11.2 | 2 | 3.3 | 28.6 | 54.6 | 0 | 1.5 |
| 9 | ND | | | | | | | | | |
| 10 | 82.6 | 44.7 | 4.3 | 9.8 | 3.3 | 5 | 9.8 | 22.2 | 0 | 17.9 |
| 92 | 23.8 | 14.1 | 39.3 | 41.9 | 4.5 | 3.5 | 32.4 | 40.5 | 0 | 0 |
| 91 | 13.3 | 7.9 | 29.6 | 32.5 | 3.4 | 2.9 | 53.4 | 56.5 | 0 | 0 |
| 87 | 14.8 | 12.2 | 28.4 | 34.1 | 5.5 | 6.6 | 51.1 | 46.5 | 0 | 0 |
| 21 | ND | | | | | | | | | |
| 34 | 11.9 | 12.9 | 10.4 | 13.7 | 0.8 | 0.6 | 76.7 | 72.8 | 0 | 0 |
| 39 | 25.6 | 13.7 | 24.6 | 25.2 | 3 | 2.8 | 46.5 | 25.2 | 0 | 0 |
| 93 | 13.3 | 8.9 | 18.4 | 18.9 | 9.9 | 10.1 | 58.2 | 61.7 | 0 | 0 |
| BB/ST | 44.2 | 32.5 | 11.7 | 12.2 | 0.8 | 0.8 | 43 | 49.4 | 0 | 4.6 |

TABLE 5

IMMUNOPHENOTYPING OF PATIENTS WITH B-CLL AND OTHER CONDITIONS BEFORE AND AFTER TREATMENT OF BLOOD SAMPLES WITH MONOCLONAL ANTIBODY TO THE HOMOLOGOUS REGION OF THE B CHAIN OF THE HLA-DR WITH MONOCLONAL ANTIBODIES TO CD16 + 56 AND CD3.

| PA-TIENTS | CD56 + &16 | | CD3+ | | CD56 + &16 + CD3+ | | CD56 + &16 − CD3− | |
|---|---|---|---|---|---|---|---|---|
| | B | A | 8 | A | B | A | B | A |
| 1 | 2 | 4.3 | 5.7 | 19.7 | 0.7 | 1.7 | 91.3 | 73 |
| 2 | 11.5 | 38.9 | 12.4 | 32.6 | 1 | 6.6 | 74.5 | 21 |
| 3 | 12 | 36.2 | 12.1 | 34.5 | 0.7 | 6 | 75.5 | 23 |
| 4 | 12.2 | 32.6 | 12.4 | 39.6 | 0.5 | 5 | 74.7 | 22.2 |

TABLE 5-continued

IMMUNOPHENOTYPING OF PATIENTS WITH B-CLL AND OTHER CONDITIONS BEFORE AND AFTER TREATMENT OF BLOOD SAMPLES WITH MONOCLONAL ANTIBODY TO THE HOMOLOGOUS REGION OF THE B CHAIN OF THE HLA-DR WITH MONOCLONAL ANTIBODIES TO CD16 + 56 AND CD3.

| PA-TIENTS | CD56 + &16 B | CD56 + &16 A | CD3+ B | CD3+ A | CD56 + &16 + CD3+ B | CD56 + &16 + CD3+ A | CD56 + &16 − CD3− B | CD56 + &16 − CD3− A |
|---|---|---|---|---|---|---|---|---|
| 5 | ND | 13.1 | ND | 9.4 | ND | 2.6 | ND | 73.5 |
| 6 | ND | | | | | | | |
| 7 | 0.8 | 0.8 | 2.8 | 2.4 | 0.3 | 0.2 | 96.2 | 96.4 |
| 8 | 24.8 | 52 | 5.4 | 12.4 | 0.9 | 4.1 | 68.3 | 31.1 |
| 9 | ND | | | | | | | |
| 10 | 1.1 | 1.3 | 6.1 | 13.7 | 2.1 | 2.5 | 90.5 | 82.4 |
| 92 | 23.8 | 34.5 | 44.3 | 44.8 | 2 | 1.5 | 29.2 | 18.6 |
| 91 | 4.6 | 3.9 | 28.8 | 29.4 | 3 | 3.2 | 63.3 | 63.3 |
| 87 | 47.9 | 46.4 | 28.8 | 36.5 | 5.8 | 3.7 | 16.9 | 13 |
| 21 | 9.4 | 9.4 | 19.7 | 23.6 | 4.2 | 6.7 | 66 | 59.5 |
| 34 | 21.5 | 12.8 | 11.4 | 13.7 | 1.8 | 0.6 | 64.6 | 72.8 |
| 39 | 7 | 2.7 | 23.4 | 26.1 | 1.1 | 0.1 | 68.2 | 71 |
| 93 | 55.8 | 54.9 | 26.2 | 26.3 | 1.7 | 2 | 16.1 | 16.8 |
| BB/ST | 28.8 | 29.9 | 12 | 14.3 | 0.8 | 1.8 | 49.4 | 53.6 |

TABLE 6

IMMUNOPHENTYPING OF PATIENTS WITH B-CLL AND OTHER CONDITIONS BEFORE AND AFTER OF TREATMENT OF BLOOD WITH MONOCLONAL ANTIBODY TO THE HOMOLOGOUS REGION OF THE B CHAIN OF THE HLA-DR WITH MONOCLONAL ANTIBODIES TO CD45 AND CD14.

| PATIENTS | CD45 + H B | CD45 + H A | CD45 + L B | CD45 + L A | CD45 + CD14+ B | CD45 + CD14+ A |
|---|---|---|---|---|---|---|
| 1 | 90.5 | 70.1 | 7.5 | 21.9 | 0.8 | 3.3 |
| 2 | 85.8 | 52.2 | 8.8 | 38.3 | 5.3 | 9.5 |
| 3 | 84.3 | 52.2 | 9.9 | 33.8 | 5.1 | 13.2 |
| 4 | 91.5 | 79.2 | 2.1 | 7 | 5.7 | 10.8 |
| 5 | 63.1 | 84.6 | 34.9 | 9.4 | 0.5 | 3.6 |
| 6 | ND | | | | | |
| 7 | 52.8 | 85.2 | 45.6 | 13.9 | 0.5 | 0.6 |
| 8 | 71.1 | 55 | 71.1 | 34.5 | 5.3 | 8.7 |
| 9 | SEE | | | | | |
| 10 | 79.7 | 47.3 | 16.3 | 48 | 2.1 | 1.9 |
| 92 | 61.7 | 64.7 | 27.4 | 26.6 | 5.9 | 3.6 |
| 91 | 49.4 | 49.2 | 40.4 | 44.3 | 6.5 | 3.2 |
| 87 | 52.4 | 61.5 | 36.1 | 28.7 | 7 | 6.5 |
| 21 | 45.8 | 43.3 | 44.3 | 47.6 | 6.2 | 3.3 |
| 34 | 24.4 | 24.6 | 54.8 | 59.6 | 13.3 | 9.7 |
| 39 | 48.7 | 46.3 | 30.5 | 42.1 | 14.5 | 8.8 |
| 93 | SEE | | | | | |
| HIV+ | 22.6 | 26.9 | 66.8 | 63.5 | 6.8 | 6.7 |
| IgA/D | 47.4 | 59.8 | 41.9 | 33.3 | 5.9 | 4.1 |

TABLE 7

IMMUNOPHENOTYPING OF PATIENT WITH B-CLL AND OTHER CONDITIONS BEFORE AND AFTER TREATMENT OF BLOOD WITH MONOCLONAL ANTIBODIES TO THE HOMOLOGOUS REGION OF THE B-CHAIN OF THE HLA-DR WITH MONOCLONAL ANTIBODIES TO CD8 AND CD3.

| PATIENTS | CD8+ B | CD8+ A | CD3+ B | CD3+ A | CD8 + CD3+ B | CD8 + CD3+ A | CD8 − CD3− B | CD8 − CD3− A |
|---|---|---|---|---|---|---|---|---|
| 2 | 0.6 | 1.3 | 7.5 | 19.3 | 4.2 | 19.3 | 87.7 | 63.8 |
| 3 | 1.1 | 1.4 | 8.3 | 20.3 | 5.6 | 18.4 | 84.8 | 59.8 |
| 4 | 3.5 | 2.9 | 8.3 | 27 | 3.9 | 18.6 | 84.2 | 53.1 |
| 92 | 3.5 | 1.9 | 27.6 | 25.2 | 18.4 | 19 | 50.3 | 52.8 |
| 91 | 4 | 3.1 | 18.2 | 19 | 14.1 | 12.6 | 63.6 | 65.3 |
| 87 | 5.7 | 3.9 | 19.9 | 23.6 | 15.4 | 17.4 | 58.8 | 55 |
| 21 | 4.8 | 7.4 | 16.3 | 17.3 | 13.7 | 13 | 65.2 | 62 |
| 34 | 3 | 3.6 | 5.2 | 6.7 | 7.6 | 7.5 | 84.1 | 82.3 |

TABLE 8

IMMUNOPHENOTYPING OF A PATIENT WITH B-CLL WITH TIME AFTER TREATMENT OF BLOOD WITH PE CONJUGATED MONOCLONAL ANTIBODY TO THE HOMOLOGOUS REGION OF THE B-CHAIN OF THE HLA-DR MEASURE WITH MONOCLONAL ANTIBODIES TO CD45 AND CD14.

| TIME | DR + CD45 + CD14 + r | CD45 + L | CD45 + H |
|---|---|---|---|
| 2 HR | 81.7 | 8.2 | 8.2 |
| 6 HR | 80.7 | 8.1 | 10.6 |
| 24 HR | 79 | 1.1 | 18.4 |

TABLE 9

IMMUNOPHENOTYPING OF A PATIENT WITH B-CLL WITH TIME AFTER TREATMENT OF BLOOD WITH PE CONJUGATED MONOCLONAL ANTIBODY TO THE HOMOLOGOUS REGION OF THE B-CHAIN OF THE HLA-DR MEASURED WITH MONOCLONAL ANTIBODIES TO CD19 AND CD3.

| TIME | CD19 + DR + r | CD3+ | CD3 + DR+ | CD19 − CD3 − DR− |
|---|---|---|---|---|
| 2 HR | 87.4 | 10.1 | 1.8 | 10.7 |
| 6 HR | 75.5 | 10.4 | 31 | 10.7 |
| 24 HR | 74 | 11.7 | 2.9 | 11 |

TABLE 10

IMMUNOPHENOTYPING OF A PATIENT WITH B-CLL WITH TIME AFTER TREATMENT OF BLOOD WITH PE CONJUGATED MONOCLONAL ANTIBODY TO THE HOMOLOGOUS REGION OF THE B-CHAIN OF THE HLA-DR MEASURED WITH MONOCLONAL ANTIBODIES TO CD4 AND CD8.

| TIME | CD8 + & DR + r | CD4+ | CD4 + &CD8 + &DR + r | CD4 + DR+ | CD4 − CD8 − DR− |
|---|---|---|---|---|---|
| 2 HR | 77.6 | 6.8 | 5.4 | 1.3 | 8.8 |
| 6 HR | 75.8 | 6.7 | 6.4 | 1.8 | 9.3 |
| 24 HR | 77 | 6.4 | 4.8 | 1.9 | 11 |

TABLE 11

IMMUNOPHENOTYPING OF A PATIENT WITH B-CLL WITH TIME AFTER TREATMENT OF BLOOD WITH PE CONJUGATED MONOCLONAL ANTIBODY TO THE HOMOLOGOUS REGION OF THE B-CHAIN OF THE HLA-DR MEASURED WITH MONOCLONAL ANTIBODIES TO CD3 AND DR.

| TIME | DR+ | CD3+ | CD3 + DR+ | CD3 + DR− |
|---|---|---|---|---|
| 2 HR | 75 | 9.5 | 4.2 | 10.9 |
| 6 HR | 74.8 | 8.8 | 4.8 | 10.9 |
| 24 HR | ND | ND | ND | ND |

TABLE 12

IMMUNOPHENOTYPING OF A PATIENT WITH B-CLL WITH TIME AFTER TREATMENT OF BLOOD WITH PE CONJUGATED MONOCLONAL ANTIBODY TO THE HOMOLOGOUS REGION OF THE B-CHAIN OF THE HLA-DR MEASURED WITH MONOCLONAL ANTIBODIES TO CD16&56 AND CD3.

| TIME | CD56 + &16 + DR + r | CD3+ | CD56 + CD16 + &CD3 + DR + r | CD56 − CD16 − &CD16 − DR− |
|---|---|---|---|---|
| 2 HR | 82.5 | 9.5 | 4.1 | 3.5 |
| 6 HR | 84.3 | 7.5 | 4.1 | 3.3 |
| 24 HR | ND | ND | ND | ND |

TABLE 13

IMMUNOPHENOTYPING OF A PATIENT WITH B-CLL WITH TIME AFTER TREATMENT OF BLOOD WITH PE CONJUGATED MONOCLONAL ANTIBODY TO THE HOMOLOGOUS REGION OF THE B-CHAIN OF THE HLA-DR MEASURED WITH MONOCLONAL ANTIBODIES TO CD8 AND CD3.

| TIME | CD8 + DR+ | CD3+ | CD8 + CD + 3&DR + r | CD8 − CD3 − DR− |
|---|---|---|---|---|
| 2 HR | 76.2 | 6.6 | 6.7 | 10.6 |
| 6 HR | 76.5 | 6.2 | 6.2 | 10.3 |

TABLE 14

IMMUNOPHENOTYPING OF PATIENTS WITH B-CLL BEFORE AND AFTER TREATMENT OF BLOOD WITH MONOCLONAL ANTIBODIES TO THE HOMOLOGOUS REGION OF THE A-CHAIN OF THE HLA-DR, THE HOMOLOGOUS REGION OF THE B-CHAIN OF THE HLA-DR, THE TWO MONOCLONAL TOGETHER, MONOCLONAL TO THE HOMOLOGOUS REGION OF THE B-CHAIN PLUS CYCLOPHOSPHOAMIDE AND THE HOMOLOGOUS REGION OF CLASS I ANTIGENS MEASURED WITH TIME.

| | CD19+ | | | | | CD3+ | | | | | CD19 + CD3+ | | | | | CD19 − CD3− | | | | |
|---|---|---|---|---|---|---|---|---|---|---|---|---|---|---|---|---|---|---|---|---|
| ID | B | AA | AB | ABC | AI | B | AA | AB | ABC | AI | B | AA | AB | ABC | AI | B | AA | AB | ABC | AI |
| 5/6 | | | | | | | | | | | | | | | | | | | | |
| 2 H 24 | 86 | 91 | 54 | 40 | 89 | 5 | 4 | 16 | 23 | 5 | 1 | 1 | 3 | 2 | 1 | 6 | 4 | 27 | 33 | 5 |
| 10 | N | 88 | 51 | 60 | 86 | N | 4 | 18 | 10 | 4 | N | 2 | 1 | 2 | 3 | N | 4 | 29 | 28 | 7 |
| 2 H 09 | 77 | N | 59 | N | 80 | 7 | N | 13 | N | 7 | 1 | N | 1 | N | 0 | 14 | N | 26 | N | 12 |
| 24 43/BD | 8 | N | N | N | 6 | 32 | N | N | N | 38 | 1 | N | N | N | 1 | 59 | N | N | N | 56 |
| 6 H 04/BD | 0 | N | 0 | 0 | 0 | 40 | N | 42 | 43 | 49 | 0 | N | 1 | 0 | 1 | 58 | N | 54 | 54 | 47 |
| 6 H HIV+ | 0 | N | 0 | 0 | 0 | 49 | N | 41 | 45 | 46 | 0 | N | 3 | 1 | 3 | 43 | N | 42 | 44 | 41 |
| 6 H IgA/D | 1 | N | 0 | N | 1 | 10 | N | 14 | N | 12 | 0 | N | 0 | N | 0 | 89 | N | 86 | N | 87 |
| 6 H | 10 | N | 1 | N | 12 | 21 | N | 25 | N | 20 | 2 | N | 1 | N | 3 | 67 | N | 71 | N | 68 |

B = Before;
A = After;
AB = after addition to antibody to beta chain;
AA = after addition of antibody to alpha chain;
ABC = after addition of antibody to either alpha or beta chain and cycloposphoamide;
AI = after addition of antibody to Class I.

TABLE 15

CD8 AND CD4

| | CD8+ | | | | | CD4+ | | | | | CD4 + CD8+ | | | | | CD4 − CD8− | | | | |
|---|---|---|---|---|---|---|---|---|---|---|---|---|---|---|---|---|---|---|---|---|
| ID | B | AA | AB | ABC | AI | B | AA | AB | ABC | AI | B | AA | AB | ABC | AI | B | AA | AB | ABC | AI |
| 5/6 | | | | | | | | | | | | | | | | | | | | |
| 2 H 24 | 3 | 2 | 14 | 10 | 4 | 2 | 2 | 8 | 8 | 3 | 0 | 0 | 3 | 2 | 1 | 95 | 94 | 74 | 79 | 93 |
| 10 | N | 3 | 9 | 4 | 4 | N | 3 | 8 | 4 | 3 | N | 0 | 2 | 2 | 0 | N | 94 | 81 | 90 | 93 |
| 2 H 09 | 3 | N | 7 | N | 4 | 4 | N | 7 | N | 3 | 1 | N | 2 | N | 1 | 91 | N | 83 | N | 92 |
| 24 | 10 | N | N | N | 15 | 21 | N | N | N | 38 | 2 | N | N | N | 2 | 61 | N | N | N | 53 |

TABLE 16

CD3 AND DR

| | DR+ | | | | | CD3+ | | | | | CD3+DR+ | | | | | CD3-DR- | | | | |
|---|---|---|---|---|---|---|---|---|---|---|---|---|---|---|---|---|---|---|---|---|
| ID | B | A | A AB | A BC | Al | B | A | A AB | A BC | Al | B | A | A AB | A BC | Al | B | A | A AB | A BC | Al |
| 5/6 2H | N | 90 | 54 | N | 87 | N | 4 | 12 | N | 4 | N | 2 | 10 | N | 3 | N | 5 | 22 | N | 5 |
| 10 2H | 83 | N | 63 | N | 81 | 4 | N | 8 | N | 4 | 4 | N | 7 | N | 4 | 9 | N | 23 | N | 12 |
| 09 24 | 14 | N | N | N | 13 | 30 | N | N | N | 36 | 3 | N | N | N | 3 | 51 | N | N | N | 47 |

TABLE 17

CD16&56 AND CD3

| | CD56+&16+ | | | | | CD3+ | | | | | CD56+&16+CD3+ | | | | | CD56+&16-CD3- | | | | |
|---|---|---|---|---|---|---|---|---|---|---|---|---|---|---|---|---|---|---|---|---|
| ID | B | A | A AB | A BC | Al | B | A | A AB | A BC | Al | B | A | A AB | A BC | Al | B | A | A AB | A BC | Al |
| 5/6 2H | N | 0 | 13 | N | 4 | N | 5 | 9 | N | 5 | N | 1 | 3 | N | 1 | N | 94 | 74 | N | 90 |
| 10 2H | 0 | N | 1 | N | 1 | 6 | N | 14 | N | 6 | 1 | N | 2 | N | 1 | 92 | N | 65 | N | 92 |
| 09 24 | 42 | N | N | N | 41 | 36 | N | N | N | 38 | 2 | N | N | N | 2 | 20 | N | N | N | 19 |

TABLE 18

CD45 AND CD14

| | CD45+L | | | | | CD45+M | | | | | CD45+H | | | | | CD45+CD14+ | | | | |
|---|---|---|---|---|---|---|---|---|---|---|---|---|---|---|---|---|---|---|---|---|
| ID | B | A | A AB | A BC | Al | B | A | A AB | A BC | Al | B | A | A AB | A BC | Al | B | A | A AB | A BC | Al |
| 5/6 2H | 0 | 0 | 5 | 10 | 0 | 44 | 43 | 50 | 50 | 32 | 55 | 43 | 50 | 31 | 67 | 1 | 1 | 1 | 2 | 0 |
| 10 2H | 0 | N | 0 | N | 0 | 43 | N | 54 | N | 35 | 54 | N | 42 | N | 62 | 1 | N | 1 | N | 0 |
| 09 24 | 2 | N | N | N | 1 | 18 | N | N | N | 16 | 71 | N | N | N | 76 | 7 | N | N | N | 5 |
| HIV+ 6H | 4 | N | 3 | N | 6 | 63 | N | 61 | N | 41 | 23 | N | 27 | N | 40 | 7 | N | 7 | N | 7 |
| IgA/D 6H | 2 | N | 2 | N | 4 | 40 | N | 31 | N | 44 | 47 | N | 60 | N | 44 | 6 | N | 4 | N | 6 |

TABLE 19

CD8 AND CD28

| | CD8+ | | | | | CD28+ | | | | | CD8+CD28+ | | | | | CD8-CD28- | | | | |
|---|---|---|---|---|---|---|---|---|---|---|---|---|---|---|---|---|---|---|---|---|
| ID | B | A | A AB | A BC | Al | B | A | A AB | A BC | Al | B | A | A AB | A BC | Al | B | A | A AB | A BC | Al |
| 5/6 2H | N | 3 | 6 | N | 3 | N | 1 | 4 | N | 2 | N | 1 | 4 | N | 1 | N | 95 | 86 | N | 94 |
| 8 2H | 4 | N | 6 | N | N | 3 | N | 5 | N | N | 1 | N | 3 | N | N | 92 | N | 86 | N | N |

TABLE 20

CD34 AND CD2

| ID | CD34+ | | | | | CD2+ | | | | | CD34+CD2+ | | | | | CD34−CD2− | | | | |
|---|---|---|---|---|---|---|---|---|---|---|---|---|---|---|---|---|---|---|---|---|
| | B | A | AB | A BC | AI | B | A | AB | A BC | AI | B | A | AB | A BC | AI | B | A | AB | A BC | AI |
| 5/6 | | | | | | | | | | | | | | | | | | | | |
| 2H | N | 1 | 34 | N | N | N | 6 | 13 | N | N | N | 3 | 30 | N | N | N | 90 | 21 | N | N |
| 24 | N | 1 | 6 | 9 | N | N | 7 | 23 | 4 | N | N | 3 | 33 | 43 | N | N | 87 | 34 | 34 | N |
| HIV + 2H BB/ST | 2 | 1 | 12 | 13 | N | 20 | 21 | 21 | 12 | N | 4 | 5 | 9 | 14 | N | 73 | 73 | 64 | 60 | N |
| 2H | 26 | 23 | 33 | 14 | N | 15 | 14 | 15 | 15 | N | 31 | 30 | 23 | 36 | N | 27 | 32 | 28 | 35 | N |
| 24 | N | 11 | 29 | 11 | N | N | 13 | 12 | 9 | N | N | 27 | 9 | 18 | N | N | 48 | 49 | 61 | N |

CHART 1

IMMUNOPHENOTYPIC CHANGES OF UNTREATED AND TREATED BLOOD SAMPLE OF PATIENT (2, 3 & 4) WITH MONOCLONAL ANTIBODY TO THE HOMOLOGOUS REGION OF THE β-CHAIN OF HLA-DR ANTIGEN MEASURED WITH TIME.

| WITHOUT | WITH | FL1 | FL2 | TIME |
|---|---|---|---|---|
| NOTHING001 | WITH002 | CD45 | CD14 | 2 HR |
| NO001 | WE002 | CD45 | CD14 | 6 HR |
| 001001 | 002002 | CD45 | CD14 | 24 HR |
| NOTHING003 | WITH004 | CD3 | CD19 | 2 HR |
| NO003 | WE004 | CD3 | CD19 | 6 HR |
| 001003 | 002004 | CD3 | CD19 | 24 HR |
| NOTHING004 | WITH005 | CD4 | CD8 | 2 HR |
| NO004 | WE005 | CD4 | CD8 | 6 HR |
| 001004 | 002005 | CD4 | CD8 | 24 HR |
| NOTHING005 | WITH006 | CD3 | DR | 2 HR |
| NO005 | WE006 | CD3 | DR | 6 HR |
| 001005 | 002006 | CD3 | DR | 24 HR |
| NOTHING006 | WITH007 | CD3 | CD56&16 | 2 HR |
| NO006 | WE007 | CD3 | CD56&16 | 6 HR |
| 001006 | 002007 | CD3 | CD56&16 | 24 HR |
| N003 | W004 | CD3 | CD8 | 2 HR |
| NO007 | WE008 | CD3 | CD8 | 6 HR |
| 001007 | 002008 | CD3 | CD8 | 24 HR |

CHART 1A

IMMUNOPHENOTYPIC CHANGES OF UNTREATED AND TREATED BLOOD SAMPLE OF PATIENT (2, 3, 4) WITH MONOCLONAL ANTIBODY TO THE HOMOLOGOUS REGION OF THE β-CHAIN OF HLA-DR ANTIGEN CONJUGATED TO PE MEASURED WITH TIME.

| ID | FL1 | FL2 | TIME |
|---|---|---|---|
| WL003 | CD45 | CD14 | 2 HR |
| WEL003 | CD45 | CD14 | 6 HR |
| 003003 | CD45 | CD14 | 24 HR |
| WL005 | CD3 | CD19 | 2 HR |
| WEL005 | CD3 | CD19 | 6 HR |
| 003005 | CD3 | CD19 | 24 HR |
| WL006 | CD4 | CD8 | 2 HR |
| WEL006 | CD4 | CD8 | 6 HR |
| 003006 | CD4 | CD8 | 24 HR |
| WL007 | CD3 | DR | 2 HR |
| WEL 007 | CD3 | DR | 6 HR |
| WL008 | CD3 | CD65&16 | 2 HR |
| WEL 008 | CD3 | CD56&16 | 6 HR |
| WL005 | CD3 | CD8 | 2 HR |
| WEL009 | CD3 | CD8 | 6 HR |

CHART 2

IMMUNOPHENOTYPIC CHANGES OF UNTREATED AND TREATED BLOOD OF PATIENT (1) WITH MONOCLONAL ANTIBODY TO THE HOMOLOGOUS REGION OF THE β-CHAIN OF HLA-DR ANTIGEN, THIS ANTIBODY AND CYCLOPHOSPHAMIDE, MONOCLONAL ANTIBODY TO THE HOMOLOGOUS REGION OF THE α-CHAIN OF HLA-DR ANTIGEN AND MONOCLONAL ANTIBODY TO THE HOMOLOGOUS REGION OF CLASS I ANTIGEN MEASURED WITH TIME.

| Error! Bookmark | WITH | WITH-OUT | FL1 | FL2 | TIME |
|---|---|---|---|---|---|
| | | NA001 | CD45 | CD14 | 2 HR |
| | A2B001:AB | | CD45 | CD14 | 2 HR |
| | A2A:AA | | CD45 | CD14 | 2 HR |
| | DNAA001:ABC | | CD45 | CD14 | 2 HR |
| | A1001:AI | | CD45 | CD14 | 2 HR |
| | | NC001 | CD3 | CD19 | 2 HR |
| | C2B001:AB | | CD3 | CD19 | 2 HR |
| | C2A001:AA | | CD3 | CD19 | 2 HR |
| | DNAC001:ABC | | CD3 | CD19 | 2 HR |
| | C1001:AI | | CD3 | CD19 | 2 HR |
| | A124H001:AI | | CD3 | CD19 | 24 HR |
| | A2B24H001:AB | | CD3 | CD19 | 24 HR |
| | A2A24H001:AA | | CD3 | CD19 | 24 HR |
| | A2BX24H001:AB | | CD3 | CD19 | 24 HR |
| | | ND001 | CD4 | CD8 | 2 HR |
| | D2B001:AB | | CD4 | CD8 | 2 HR |
| | D2A001:AA | | CD4 | CD8 | 2 HR |
| | DNAD001:ABC | | CD4 | CD8 | 2 HR |
| | D1001:AI | | CD4 | CD8 | 2 HR |
| | D124H001:AI | | CD4 | CD8 | 24 HR |
| | D2BX24H001:AB | | CD4 | CD8 | 24 HR |
| | D2B001:AB | | CD4 | CD8 | 24 HR |
| | D2A001:AA | | CD4 | CD8 | 24 HR |
| | E1001:AI | | CD3 | DR | 2 HR |
| | E2B001:AB | | CD3 | DR | 2 HR |
| | E2A001:AA | | CD3 | DR | 2 HR |
| | F1001:AI | | CD3 | CD56&16 | 2 HR |
| | F2B001:AB | | CD3 | CD56&16 | 2 HR |
| | F2A001:AA | | CD3 | CD56&16 | 2 HR |
| | G1001:AI | | CD28 | CD8 | 2 HR |
| | G2A001:AA | | CD28 | CD8 | 2 HR |
| | G2B001:AB | | CD28 | CD8 | 2 HR |
| | H1001:AI | | CD7 | CD33&13 | 2 HR |
| | H2A001:AA | | CD7 | CD33&13 | 2 HR |
| | H2B001:AB | | CD7 | CD33&13 | 2 HR |
| | I2A001:AA | | CD21 | CD5 | 2 HR |
| | I2B001:AB | | CD21 | CD5 | 2 HR |
| | J2A001:AA | | CD34 | CD2 | 2 HR |
| | J2B001:AB | | CD34 | CD2 | 2 HR |
| | B2A24H001:AA | | CD34 | CD2 | 24 HR |
| | B2B24H001:AB | | CD34 | CD2 | 24 HR |

CHART 2-continued

IMMUNOPHENOTYPIC CHANGES OF UNTREATED AND TREATED BLOOD OF PATIENT (1) WITH MONOCLONAL ANTIBODY TO THE HOMOLOGOUS REGION OF THE β-CHAIN OF HLA-DR ANTIGEN, THIS ANTIBODY AND CYCLOPHOSPHAMIDE, MONOCLONAL ANTIBODY TO THE HOMOLOGOUS REGION OF THE α-CHAIN OF HLA-DR ANTIGEN AND MONOCLONAL ANTIBODY TO THE HOMOLOGOUS REGION OF CLASS I ANTIGEN MEASURED WITH TIME.

| Error! Bookmark | WITH | WITH-OUT | FL1 | FL2 | TIME |
|---|---|---|---|---|---|
| | B2BX24H001:ABC | | CD34 | CD2 | 24 HR |
| | K2B001:AB | | CD10 | CD25 | 2 HR |
| | K2A001:AA | | CD10 | CD25 | 2 HR |

CHART 3

IMMUNOPHENOTYPIC CHANGES OF UNTREATED AND TREATED BLOOD OF PATIENT (8) WITH MONOCLONAL ANTIBODY TO THE HOMOLOGOUS REGION OF THE β-CHAIN OF HLA-DR ANTIGEN.

| WITH | WITHOUT | FL1 | FL2 | TIME |
|---|---|---|---|---|
| | AN001 | CD45 | CD14 | 2 HR |
| A2001 | | CD45 | CD14 | 2 HR |
| | CN001 | CD3 | CD19 | 2 HR |
| C2001 | | CD3 | CD19 | 2 HR |
| | DN001 | CD4 | CD8 | 2 HR |
| D2001 | | CD4 | CD8 | 2 HR |
| | EN001 | CD3 | DR | 2 HR |
| E2001 | | CD3 | DR | 2 HR |
| | FN001 | CD3 | CD56&16 | 2 HR |
| F2001 | | CD3 | CD56&16 | 2 HR |
| | GN001 | CD28 | CD8 | 2 HR |
| G2001 | | CD28 | CD8 | 2 HR |
| | HN001 | CD7 | CD5 | 2 HR |
| H2001 | | CD7 | CD5 | 2 HR |
| | IN001 | CD13 | CD20 | 2 HR |
| I2001 | | CD13 | CD20 | 2 HR |
| | JN001 | CD45RA | CD25 | 2 HR |
| J2001 | | CD45RA | CD25 | 2 HR |
| | KN001 | CD57 | CD23 | 2 HR |
| K2001 | | CD57 | CD23 | 2 HR |

CHART 4

IIMMUNOPHENOTYPIC CHANGES OF UNTREATED AND TREATED BLOOD SAMPLE OF PATIENT (10) WITH MONOCLONAL ANTIBODY TO THE HOMOLOGOUS REGION OF THE β-CHAIN OF HLA-DR ANTIGEN AND MONOCLONAL ANTIBODY TO THE HOMOLOGOUS REGION OF CLASS 1 ANTIGENS.

| WITH | WITHOUT | FL1 | FL2 | TIME |
|---|---|---|---|---|
| | CLL0001 | CD45 | CD14 | 2 HR |
| CLL1001 | | CD45 | CD14 | 2 HR |
| CLL2001 | | CD45 | CD14 | 2 HR |
| | CLL0003 | CD3 | CD19 | 2 HR |
| | | CD3 | CD19 | 2 HR |
| CLL1003 | | CD3 | CD19 | 2 HR |
| CLL2003 | | CD3 | CD19 | 2 HR |
| | CLL0004 | CD4 | CD8 | 2 HR |
| CLL1004 | | CD4 | CD8 | 2 HR |
| CLL2004 | | CD4 | CD8 | 2 HR |
| | CLL005 | CD3 | DR | 2 HR |
| CLL1005 | | CD3 | DR | 2 HR |
| CLL2005 | | CD3 | DR | 2 HR |

CHART 4-continued

IIMMUNOPHENOTYPIC CHANGES OF UNTREATED AND TREATED BLOOD SAMPLE OF PATIENT (10) WITH MONOCLONAL ANTIBODY TO THE HOMOLOGOUS REGION OF THE β-CHAIN OF HLA-DR ANTIGEN AND MONOCLONAL ANTIBODY TO THE HOMOLOGOUS REGION OF CLASS 1 ANTIGENS.

| WITH | WITHOUT | FL1 | FL2 | TIME |
|---|---|---|---|---|
| | CLL0006 | CD3 | CD56&16 | 2 HR |
| CLL1006 | | CD3 | CD56&16 | 2 HR |
| CLL2006 | | CD3 | CD56&16 | 2 HR |

I claim:

1. A method of increasing the relative number of CD34$^+$ cells in a cell population comprised of hematopoietic cells, including committed cells, which method comprises:
   (i) contacting the cell population with an antibody that operably engages an MHC class I antigen or an MHC class II antigen on said committed cells; and
   (ii) incubating committed cells that are engaged by said antibody such that the relative number of CD34$^+$ cells increases as a result of said engaging.

2. The method of claim 1 wherein the committed cells are hemopoietic cells.

3. A method according to claim 1 wherein said MHC class I antigen is a Human Leukocyte-Associated (HLA)-A receptor, an HLA-B receptor, an HLA-C receptor, an HLA-E receptor, an HLA-F receptor or an HLA-G receptor and said MHC class II antigen is an HLA-DM receptor, an HLA-DP receptor, an HLA-DQ receptor or an HLA-DR receptor.

4. The method according to claim 3 wherein the MHC class I antigen is an HLA-DR receptor.

5. The method according to claim 4 wherein the HLA-DR receptor comprises a β-chain.

6. The method according to claim 5 wherein the β-chain has homologous regions.

7. The method according to claim 6 wherein the HLA-DR receptor comprises at least the homologous region of the β-chain of HLA-DR.

8. A method according to claim 1 wherein the antibody is a monoclonal antibody.

9. A method according to claim 8 wherein the antibody is selected from the group consisting of monoclonal antibody CR3/43 and monoclonal antibody TAL 1B5.

10. A method according to claim 9, wherein the antibody is CR3/43.

11. The method according to claim 1 wherein said incubating is from 2 to 24 hours.

12. The method according to claim 1 wherein the committed cells are non-cancer cells.

13. The method according to claim 1 wherein the committed cells are differentiated cells.

14. The method according to claim 1 wherein the committed cells include at least one cell type selected from the group consisting of T-cell colony-forming cells (CFC-T cells), B-cell colony-forming cells (CFC-B cells), cosinophil colony-forming cells (CFC-Eosin cells), basophil colony-forming cells (CFC-Bas cells), granulocyte/monocyte colony-forming cells (CFC-GM cells), megakaryocyte colony-forming cells (CFC-MEG cells), erythrocyte burst-forming cells (BFC-E cells), erythrocyte colony-forming cells (CFC-E cells), T-cells and B cells.

15. The method according to claim 1 wherein the CD34$^+$ cells are Major Histocompatibility Complex (MHC) class I$^+$ and MHC class II$^+$ cells.

16. A method according to claim 1 wherein the antibody is used in conjunction with a biological response modifier.

17. A method according to claim 16 wherein the biological response modifier is an alkylating agent.

18. A method according to claim 17 wherein the alkylating agent is or comprises cyclophosphoamide.

* * * * *

UNITED STATES PATENT AND TRADEMARK OFFICE
CERTIFICATE OF CORRECTION

PATENT NO. : 7,220,412 B2
APPLICATION NO. : 10/140978
DATED : May 22, 2007
INVENTOR(S) : Ilham Saleh Abuljadayel It is certified that error appears in the above-identified patent and that said Letters Patent is hereby corrected as shown below:

Column 64, Claim 14 line 58; should read

The method according to claim 1 wherein the committed cells include at least one cell type selected from the group consisting of T-cell colony-forming cells (CFC-T cells), B-cell colony-forming cells (CFC-B cells), "cosinophil" --eosinophil-- colony-forming cells (CFC-Bosin cells), basophil colony-forming cells (CFC-Bas cells), granulocyte/monocyte colony- forming cells (CFC-GM cells), megakaryocyte colony-forming cells (CFC-MEG cells), erythrocyte burst-forming cells (BFC-E cells), erythrocyte colony-forming cells (CFC-E cells), T-cells and B cells.

Signed and Sealed this

Thirteenth Day of November, 2007

JON W. DUDAS
*Director of the United States Patent and Trademark Office*